US010354749B2

(12) United States Patent
Yamane et al.

(10) Patent No.: US 10,354,749 B2
(45) Date of Patent: Jul. 16, 2019

(54) CONFERENCE PREPARATION APPARATUS, CONFERENCE PREPARATION METHOD, AND STORAGE MEDIUM

(71) Applicant: CANON KABUSHIKI KAISHA, Tokyo (JP)

(72) Inventors: Toshimizu Yamane, Tokyo (JP); Gakuya Soeda, Isehara (JP); Takahiro Kurosawa, Kunitachi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/786,016

(22) Filed: Mar. 5, 2013

(65) Prior Publication Data

US 2013/0238358 A1 Sep. 12, 2013

(30) Foreign Application Priority Data

Mar. 7, 2012 (JP) ................................ 2012-050685
Mar. 7, 2012 (JP) ................................ 2012-050686
Mar. 7, 2012 (JP) ................................ 2012-050687

(51) Int. Cl.
*G06Q 50/22* (2018.01)
*G06F 3/048* (2013.01)
(Continued)

(52) U.S. Cl.
CPC ........... *G16H 10/60* (2018.01); *G06F 19/324* (2013.01)

(58) Field of Classification Search
CPC .................... G06Q 50/22; G06Q 50/24; G06T 2207/10116; G06T 7/0012; G06F 15/16
(Continued)

(56) References Cited

U.S. PATENT DOCUMENTS 5,845,253 A 12/1998 Rensimer et al.
6,006,191 A * 12/1999 DiRienzo ............. G06F 19/321 705/2

(Continued)

FOREIGN PATENT DOCUMENTS

CN 1855831 A 11/2006
CN 101968865 A 2/2011

(Continued)

OTHER PUBLICATIONS

Google patents search, Aug. 30, 2016.*

(Continued)

*Primary Examiner* — Dilek B Cobanoglu
(74) *Attorney, Agent, or Firm* — Canon U.S.A., Inc. IP Division

(57) ABSTRACT

A conference preparation apparatus includes a material identification information acquisition unit configured to acquire material identification information specified by an operation performed on a display screen, a material information acquisition unit configured to acquire material information from a server based on the material identification information acquired by the material identification information acquisition unit, a management unit configured to manage on a person-by-person basis the material information acquired by the material information acquisition unit, and an agenda management unit configured to associate the material identification information with conference items.

6 Claims, 75 Drawing Sheets

(51) Int. Cl.
*G16H 10/60* (2018.01)
*G06F 19/00* (2018.01)

(58) Field of Classification Search
USPC .................. 705/2, 3; 382/131, 132; 709/227
See application file for complete search history.

(56) References Cited

U.S. PATENT DOCUMENTS

| | | | | |
|---|---|---|---|---|
| 6,154,726 | A | 11/2000 | Rensimer et al. | |
| 7,424,679 | B1 * | 9/2008 | Lamer et al. | 715/737 |
| 7,547,278 | B2 | 6/2009 | Miyazaki et al. | |
| 7,908,155 | B2 * | 3/2011 | Fuerst | G06F 19/322 705/2 |
| 8,610,966 | B2 * | 12/2013 | Hatzav | G03B 15/00 348/207.1 |
| 2004/0204961 | A1 | 10/2004 | Rensimer et al. | |
| 2005/0228890 | A1 * | 10/2005 | Lawrence | G06F 3/0481 709/227 |
| 2006/0285753 | A1 * | 12/2006 | Yamasaki | G06F 19/321 382/209 |
| 2007/0168231 | A1 * | 7/2007 | Sasai | 705/2 |
| 2007/0288268 | A1 * | 12/2007 | Weeks | G06F 19/322 705/3 |
| 2009/0041329 | A1 * | 2/2009 | Nordell | G06F 19/321 382/134 |
| 2010/0094656 | A1 * | 4/2010 | Conant | G06F 19/327 705/3 |
| 2010/0122220 | A1 * | 5/2010 | Ainsworth | G06F 16/957 715/866 |
| 2010/0262925 | A1 * | 10/2010 | Liu et al. | 715/759 |
| 2011/0054944 | A1 * | 3/2011 | Sandberg et al. | 705/3 |
| 2012/0039520 | A1 * | 2/2012 | Humphreys | A61B 6/145 382/132 |
| 2012/0239420 | A1 * | 9/2012 | Stapelfeldt | G06Q 10/10 705/2 |

FOREIGN PATENT DOCUMENTS

| | | |
|---|---|---|
| JP | 2005-043951 A | 2/2005 |
| JP | 2006-268120 A | 10/2006 |
| JP | 2009-188809 A | 8/2009 |

OTHER PUBLICATIONS

Google patents search, Apr. 25, 2017.*
Understanding and using windows API calls for excel programming, Rob Bovey, Stephen Bullen, John Green, Feb. 11, 2005, Working with windows (The article from the book: Professional excel development) (Year: 2005).*
Google patents search, Apr. 30, 2018 (Year: 2012).*
Google search, Apr. 30, 2018 (Year: 2012).*

* cited by examiner

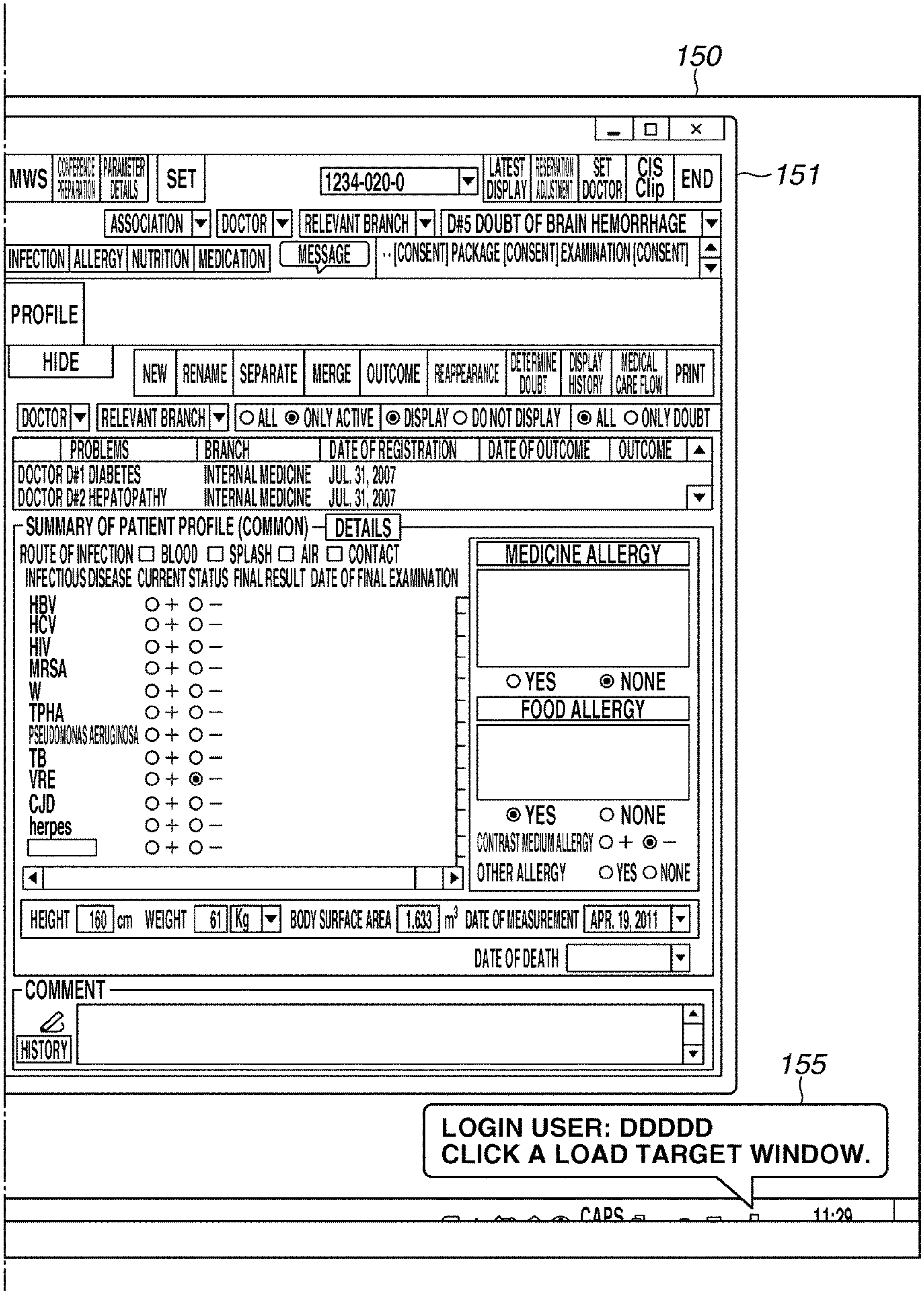

| MWS | CONFERENCE PREPARATION | PARAMETER DETAILS | SET | 1234-020-0 ▼ | LATEST DISPLAY | RESERVATION ADJUSTMENT | SET DOCTOR | CIS Clip | END |

ASSOCIATION ▼ | DOCTOR ▼ | RELEVANT BRANCH ▼ | D#5 DOUBT OF BRAIN HEMORRHAGE ▼

INFECTION | ALLERGY | NUTRITION | MEDICATION | MESSAGE | ··[CONSENT] PACKAGE [CONSENT] EXAMINATION [CONSENT]

PROFILE

HIDE | NEW | RENAME | SEPARATE | MERGE | OUTCOME | REAPPEARANCE | DETERMINE DOUBT | DISPLAY HISTORY | MEDICAL CARE FLOW | PRINT

DOCTOR ▼ | RELEVANT BRANCH ▼ | ○ ALL ⦿ ONLY ACTIVE | ⦿ DISPLAY ○ DO NOT DISPLAY | ⦿ ALL ○ ONLY DOUBT

| PROBLEMS | BRANCH | DATE OF REGISTRATION | DATE OF OUTCOME | OUTCOME |
|---|---|---|---|---|
| DOCTOR D#1 DIABETES | INTERNAL MEDICINE | JUL. 31, 2007 | | |
| DOCTOR D#2 HEPATOPATHY | INTERNAL MEDICINE | JUL. 31, 2007 | | |

─ SUMMARY OF PATIENT PROFILE (COMMON) ─ DETAILS

ROUTE OF INFECTION ☐ BLOOD ☐ SPLASH ☐ AIR ☐ CONTACT

INFECTIOUS DISEASE   CURRENT STATUS   FINAL RESULT   DATE OF FINAL EXAMINATION

| HBV | ○ + ○ − |
| HCV | ○ + ○ − |
| HIV | ○ + ○ − |
| MRSA | ○ + ○ − |
| W | ○ + ○ − |
| TPHA | ○ + ○ − |
| PSEUDOMONAS AERUGINOSA | ○ + ○ − |
| TB | ○ + ○ − |
| VRE | ○ + ⦿ − |
| CJD | ○ + ○ − |
| herpes | ○ + ○ − |
|  | ○ + ○ − |

MEDICINE ALLERGY

○ YES ⦿ NONE

FOOD ALLERGY

⦿ YES ○ NONE

CONTRAST MEDIUM ALLERGY ○ + ⦿ −
OTHER ALLERGY ○ YES ○ NONE

HEIGHT 160 cm | WEIGHT 61 Kg ▼ | BODY SURFACE AREA 1.633 m² | DATE OF MEASUREMENT APR. 19, 2011 ▼

DATE OF DEATH

─ COMMENT ─
HISTORY

*155*

LOGIN USER: DDDDD
CLICK A LOAD TARGET WINDOW.

CAPS    11:29

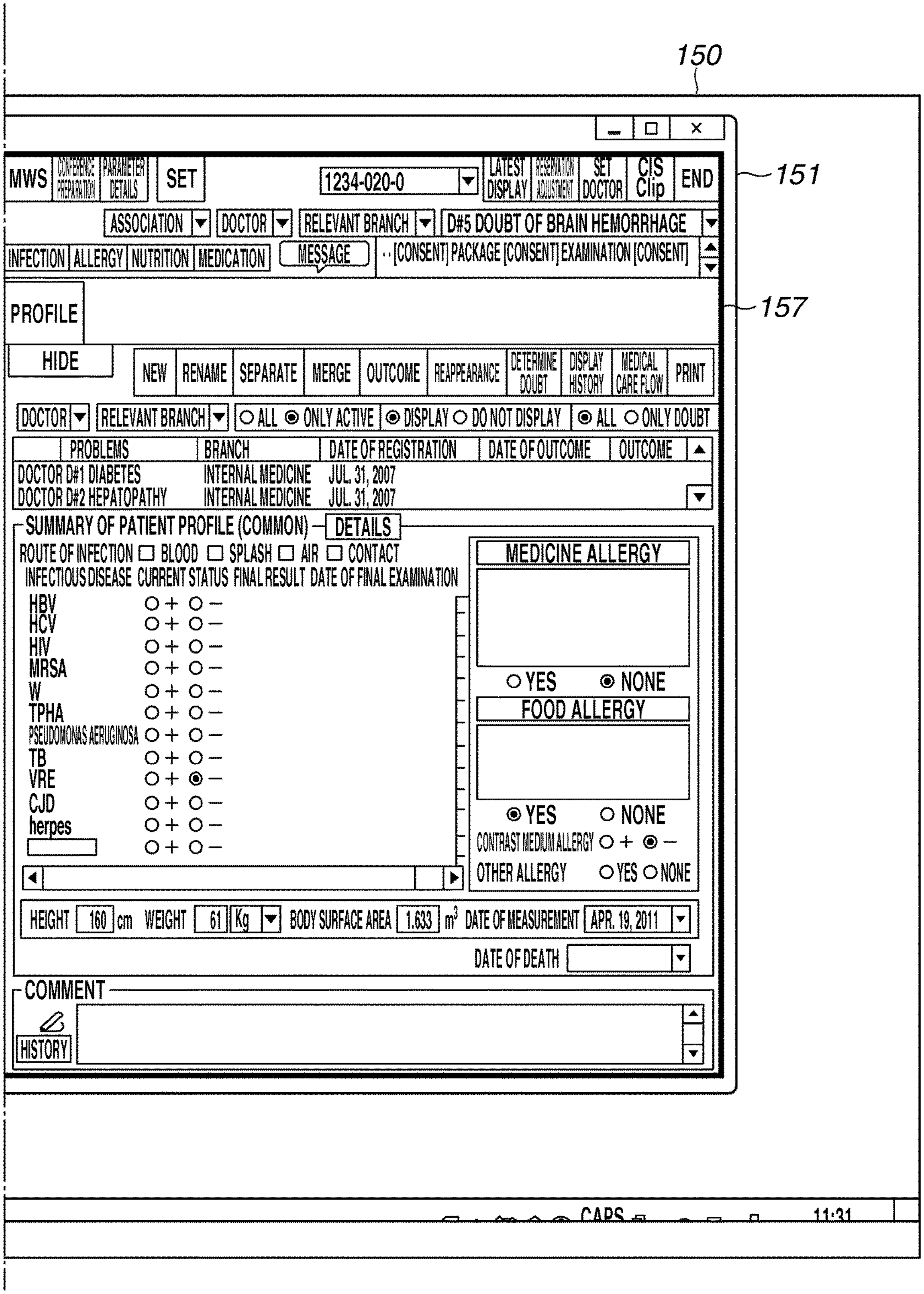

| MWS | CONFERENCE PREPARATION | PARAMETER DETAILS | SET | 1234-020-0 ▼ | LATEST DISPLAY | RESERVATION ADJUSTMENT | SET DOCTOR | CIS Clip | END |

[ ASSOCIATION ▼ ] [ DOCTOR ▼ ] [ RELEVANT BRANCH ▼ ] [ D#5 DOUBT OF BRAIN HEMORRHAGE ▼ ]
| INFECTION | ALLERGY | NUTRITION | MEDICATION | MESSAGE | ··[CONSENT] PACKAGE [CONSENT] EXAMINATION [CONSENT] |

*157*

PROFILE

| HIDE | | NEW | RENAME | SEPARATE | MERGE | OUTCOME | REAPPEARANCE | DETERMINE DOUBT | DISPLAY HISTORY | MEDICAL CARE FLOW | PRINT |

[ DOCTOR ▼ ] [ RELEVANT BRANCH ▼ ] ○ ALL ⦿ ONLY ACTIVE | ⦿ DISPLAY ○ DO NOT DISPLAY | ⦿ ALL ○ ONLY DOUBT

| PROBLEMS | BRANCH | DATE OF REGISTRATION | DATE OF OUTCOME | OUTCOME |
|---|---|---|---|---|
| DOCTOR D#1 DIABETES | INTERNAL MEDICINE | JUL. 31, 2007 | | |
| DOCTOR D#2 HEPATOPATHY | INTERNAL MEDICINE | JUL. 31, 2007 | | |

─ SUMMARY OF PATIENT PROFILE (COMMON) ─ [ DETAILS ]
ROUTE OF INFECTION □ BLOOD □ SPLASH □ AIR □ CONTACT
INFECTIOUS DISEASE   CURRENT STATUS   FINAL RESULT   DATE OF FINAL EXAMINATION

HBV         ○ + ○ −
HCV         ○ + ○ −
HIV         ○ + ○ −
MRSA        ○ + ○ −
W           ○ + ○ −
TPHA        ○ + ○ −
PSEUDOMONAS AERUGINOSA ○ + ○ −
TB          ○ + ○ −
VRE         ○ + ⦿ −
CJD         ○ + ○ −
herpes      ○ + ○ −
            ○ + ○ −

MEDICINE ALLERGY

○ YES   ⦿ NONE

FOOD ALLERGY

⦿ YES   ○ NONE
CONTRAST MEDIUM ALLERGY ○ + ⦿ −
OTHER ALLERGY   ○ YES ○ NONE

HEIGHT [ 160 ] cm   WEIGHT [ 61 ][Kg ▼]   BODY SURFACE AREA [ 1.633 ] m²   DATE OF MEASUREMENT [ APR. 19, 2011 ▼]
DATE OF DEATH [        ▼]

─ COMMENT ─
[HISTORY]

BEFORE ENTRY

AFTER ENTRY

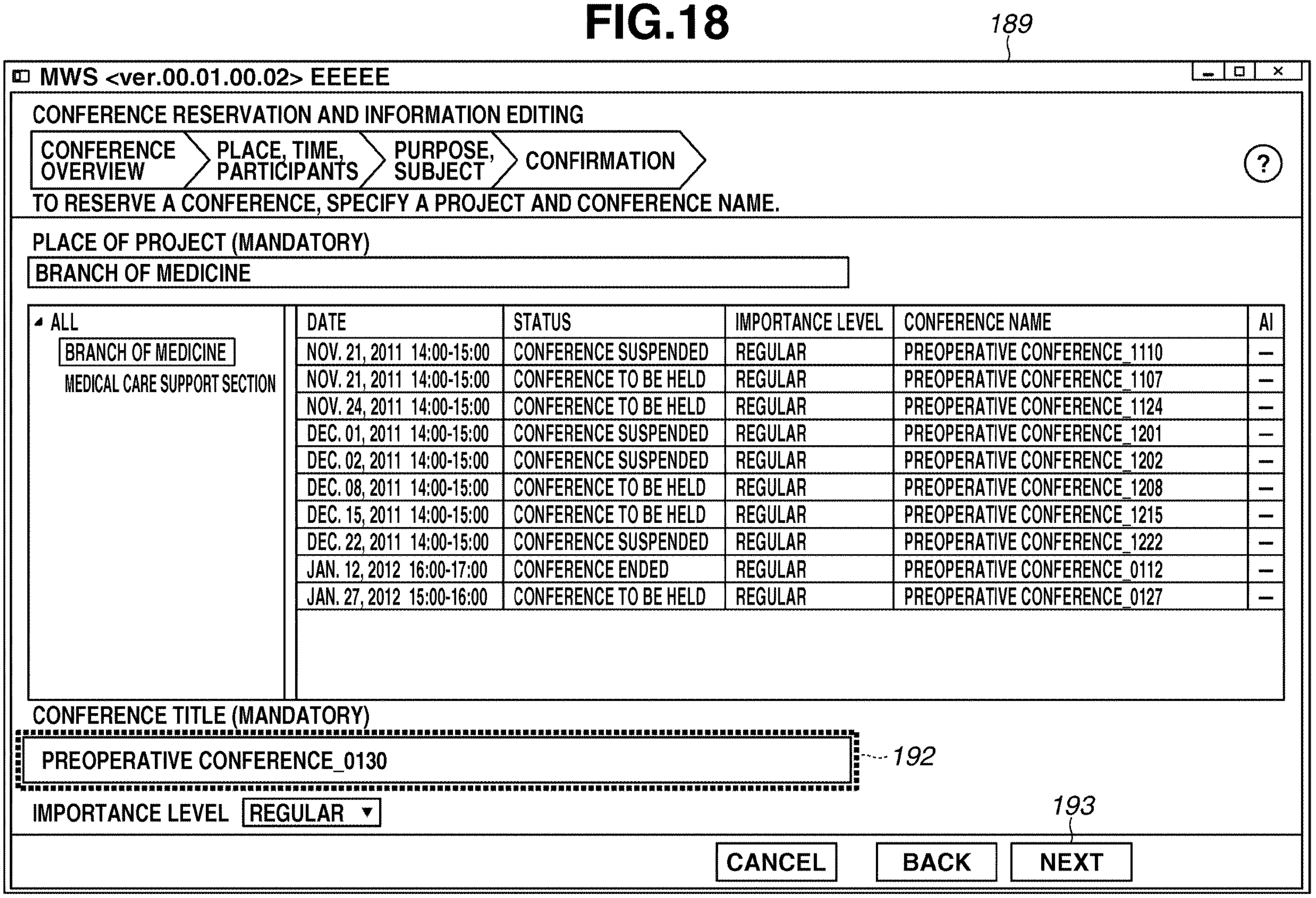

FIG.18

MWS <ver.00.01.00.02> EEEEE — 189

CONFERENCE RESERVATION AND INFORMATION EDITING

CONFERENCE OVERVIEW > PLACE, TIME, PARTICIPANTS > PURPOSE, SUBJECT > CONFIRMATION

TO RESERVE A CONFERENCE, SPECIFY A PROJECT AND CONFERENCE NAME.

PLACE OF PROJECT (MANDATORY)
BRANCH OF MEDICINE

| ▲ ALL | DATE | STATUS | IMPORTANCE LEVEL | CONFERENCE NAME | AI |
|---|---|---|---|---|---|
| BRANCH OF MEDICINE | NOV. 21, 2011 14:00-15:00 | CONFERENCE SUSPENDED | REGULAR | PREOPERATIVE CONFERENCE_1110 | — |
| MEDICAL CARE SUPPORT SECTION | NOV. 21, 2011 14:00-15:00 | CONFERENCE TO BE HELD | REGULAR | PREOPERATIVE CONFERENCE_1107 | — |
| | NOV. 24, 2011 14:00-15:00 | CONFERENCE TO BE HELD | REGULAR | PREOPERATIVE CONFERENCE_1124 | — |
| | DEC. 01, 2011 14:00-15:00 | CONFERENCE SUSPENDED | REGULAR | PREOPERATIVE CONFERENCE_1201 | — |
| | DEC. 02, 2011 14:00-15:00 | CONFERENCE SUSPENDED | REGULAR | PREOPERATIVE CONFERENCE_1202 | — |
| | DEC. 08, 2011 14:00-15:00 | CONFERENCE TO BE HELD | REGULAR | PREOPERATIVE CONFERENCE_1208 | — |
| | DEC. 15, 2011 14:00-15:00 | CONFERENCE SUSPENDED | REGULAR | PREOPERATIVE CONFERENCE_1215 | — |
| | DEC. 22, 2011 14:00-15:00 | CONFERENCE SUSPENDED | REGULAR | PREOPERATIVE CONFERENCE_1222 | — |
| | JAN. 12, 2012 16:00-17:00 | CONFERENCE ENDED | REGULAR | PREOPERATIVE CONFERENCE_0112 | — |
| | JAN. 27, 2012 15:00-16:00 | CONFERENCE TO BE HELD | REGULAR | PREOPERATIVE CONFERENCE_0127 | — |

CONFERENCE TITLE (MANDATORY)
PREOPERATIVE CONFERENCE_0130    — 192

IMPORTANCE LEVEL [REGULAR ▼]

[CANCEL]    [BACK]    [NEXT]    — 193

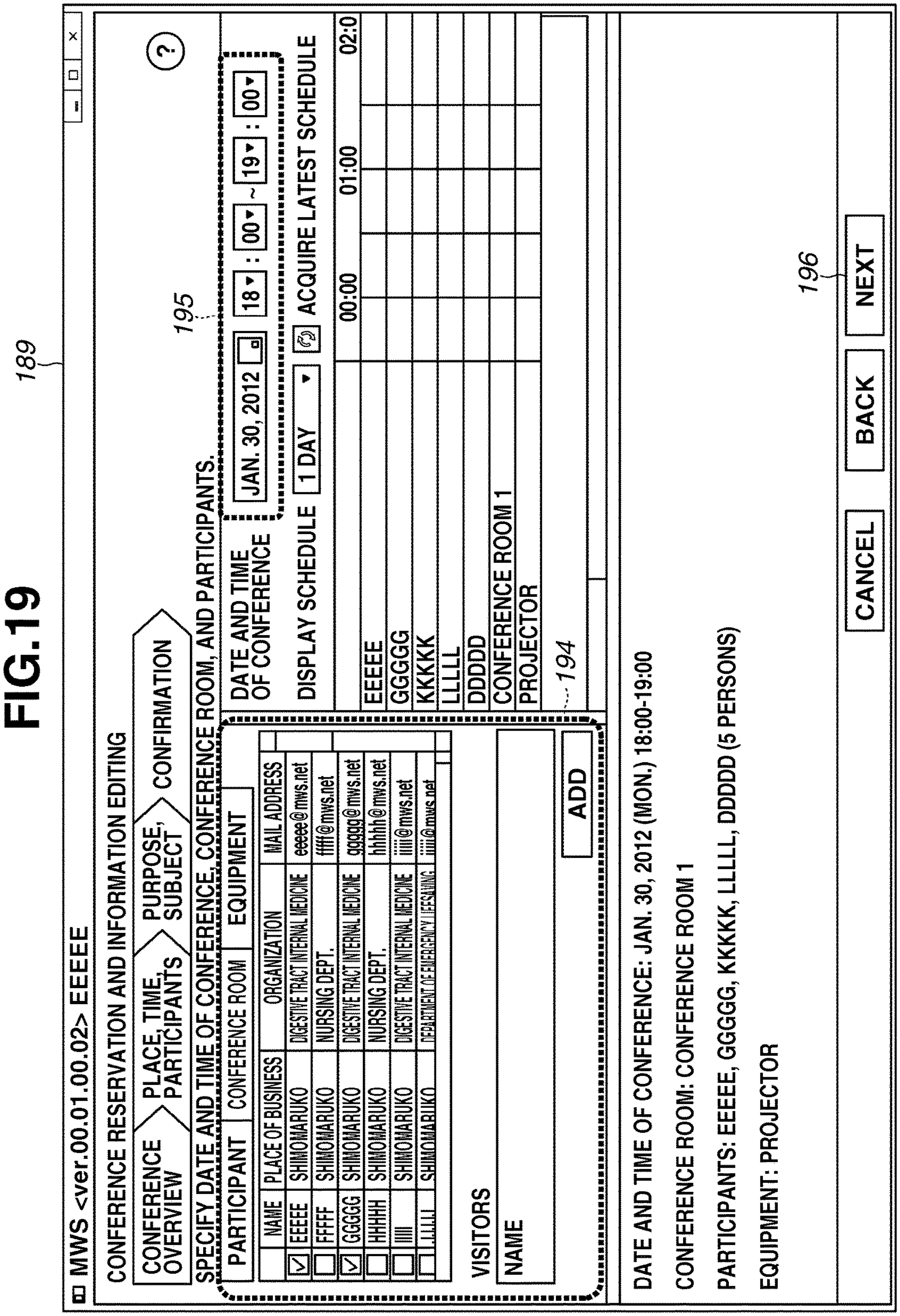

FIG.19

MWS <ver.00.01.00.02> EEEEE

CONFERENCE RESERVATION AND INFORMATION EDITING

CONFERENCE OVERVIEW > PLACE, TIME, PARTICIPANTS > PURPOSE, SUBJECT > CONFIRMATION

SPECIFY DATE AND TIME OF CONFERENCE, CONFERENCE ROOM, AND PARTICIPANTS.

PARTICIPANT | CONFERENCE ROOM | EQUIPMENT

| | NAME | PLACE OF BUSINESS | ORGANIZATION | MAIL ADDRESS |
|---|---|---|---|---|
| ☑ | EEEEE | SHIMOMARUKO | DIGESTIVE TRACT INTERNAL MEDICINE | eeeee@mws.net |
| ☐ | FFFFF | SHIMOMARUKO | NURSING DEPT. | fffff@mws.net |
| ☑ | GGGGG | SHIMOMARUKO | DIGESTIVE TRACT INTERNAL MEDICINE | ggggg@mws.net |
| ☐ | HHHHH | SHIMOMARUKO | NURSING DEPT. | hhhhh@mws.net |
| ☐ | IIIII | SHIMOMARUKO | DIGESTIVE TRACT INTERNAL MEDICINE | iiiii@mws.net |
| ☐ | JJJJJ | SHIMOMABUKO | DEPARTMENT OF EMERGENCY LIFESAVING | jjjjj@mws.net |

VISITORS
NAME

[ ADD ]

DATE AND TIME OF CONFERENCE: [JAN. 30, 2012] DISPLAY SCHEDULE [1 DAY ▼] [18▼]:[00▼] ~ [19▼]:[00▼]

ACQUIRE LATEST SCHEDULE

| | 00:00 | 01:00 | 02:0 |
|---|---|---|---|
| EEEEE | | | |
| GGGGG | | | |
| KKKKK | | | |
| LLLLL | | | |
| DDDDD | | | |
| CONFERENCE ROOM 1 | | | |
| PROJECTOR | | | |

DATE AND TIME OF CONFERENCE: JAN. 30, 2012 (MON.) 18:00-19:00
CONFERENCE ROOM: CONFERENCE ROOM 1
PARTICIPANTS: EEEEE, GGGGG, KKKKK, LLLLL, DDDDD (5 PERSONS)
EQUIPMENT: PROJECTOR

[ CANCEL ] [ BACK ] [ NEXT ]

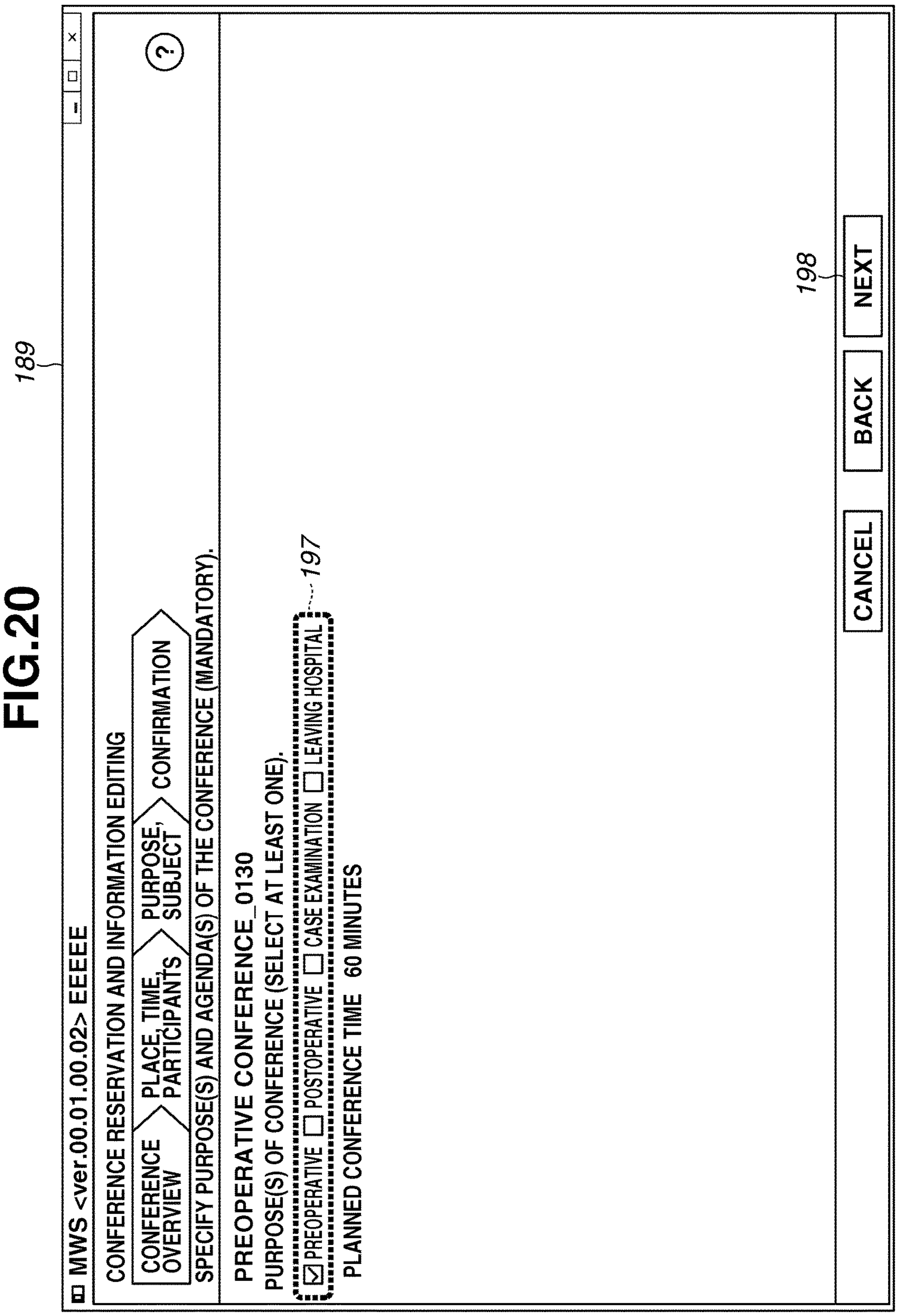

FIG.20

□ MWS <ver.00.01.00.02> EEEEE

CONFERENCE RESERVATION AND INFORMATION EDITING

| CONFERENCE OVERVIEW 〉 PLACE, TIME, PARTICIPANTS 〉 PURPOSE, SUBJECT 〉 CONFIRMATION

SPECIFY PURPOSE(S) AND AGENDA(S) OF THE CONFERENCE (MANDATORY).

PREOPERATIVE CONFERENCE_0130
PURPOSE(S) OF CONFERENCE (SELECT AT LEAST ONE).
☑ PREOPERATIVE ☐ POSTOPERATIVE ☐ CASE EXAMINATION ☐ LEAVING HOSPITAL ---197
PLANNED CONFERENCE TIME  60 MINUTES

CANCEL  BACK  NEXT —198

189

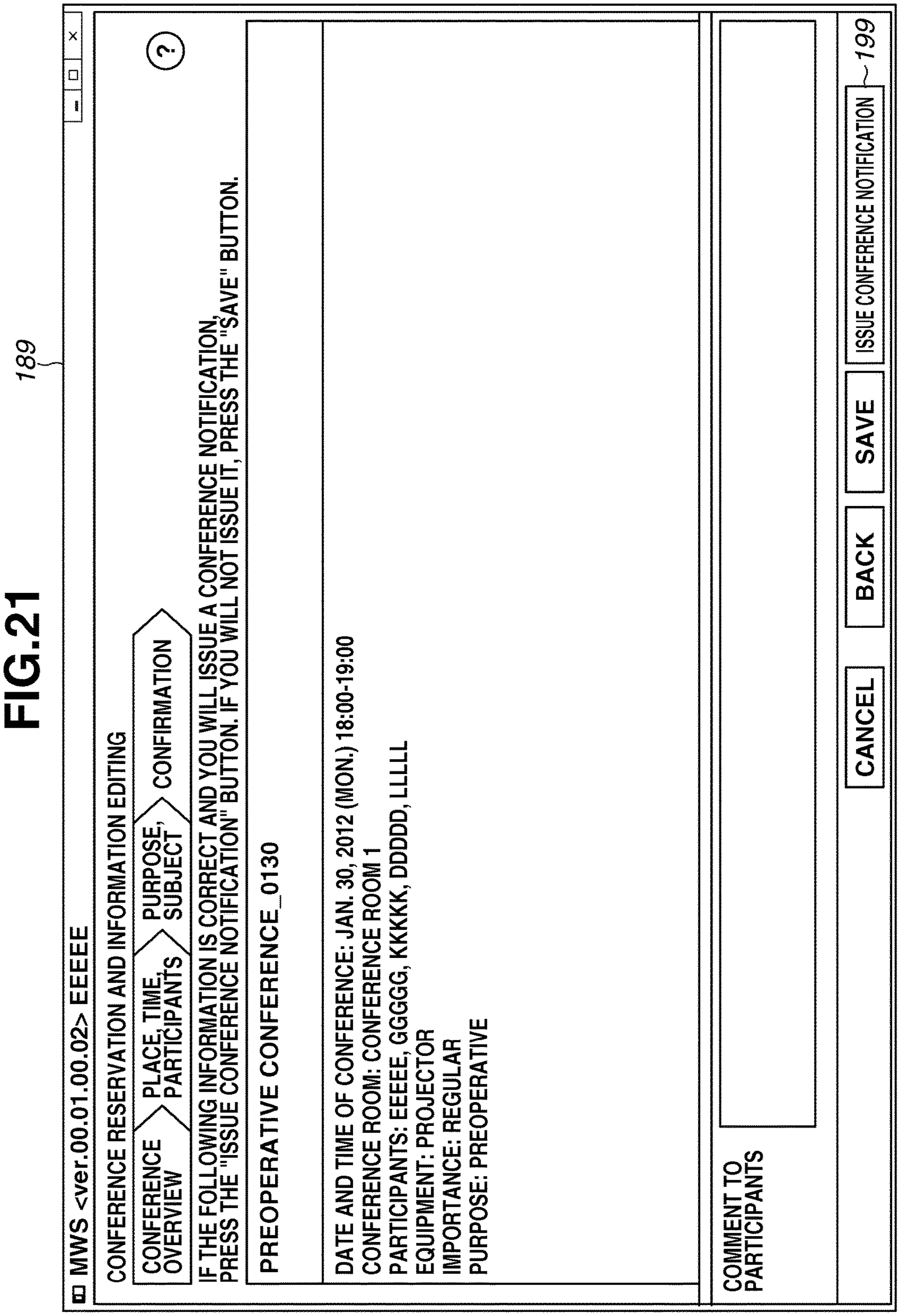

FIG.21

MWS <ver.00.01.00.02> EEEEE

CONFERENCE RESERVATION AND INFORMATION EDITING

| CONFERENCE OVERVIEW | PLACE, TIME, PARTICIPANTS | PURPOSE, SUBJECT | CONFIRMATION |

IF THE FOLLOWING INFORMATION IS CORRECT AND YOU WILL ISSUE A CONFERENCE NOTIFICATION, PRESS THE "ISSUE CONFERENCE NOTIFICATION" BUTTON. IF YOU WILL NOT ISSUE IT, PRESS THE "SAVE" BUTTON.

PREOPERATIVE CONFERENCE_0130

DATE AND TIME OF CONFERENCE: JAN. 30, 2012 (MON.) 18:00-19:00
CONFERENCE ROOM: CONFERENCE ROOM 1
PARTICIPANTS: EEEEE, GGGGG, KKKKK, DDDDD, LLLLL
EQUIPMENT: PROJECTOR
IMPORTANCE: REGULAR
PURPOSE: PREOPERATIVE

COMMENT TO PARTICIPANTS

CANCEL    BACK    SAVE    ISSUE CONFERENCE NOTIFICATION — 199

189

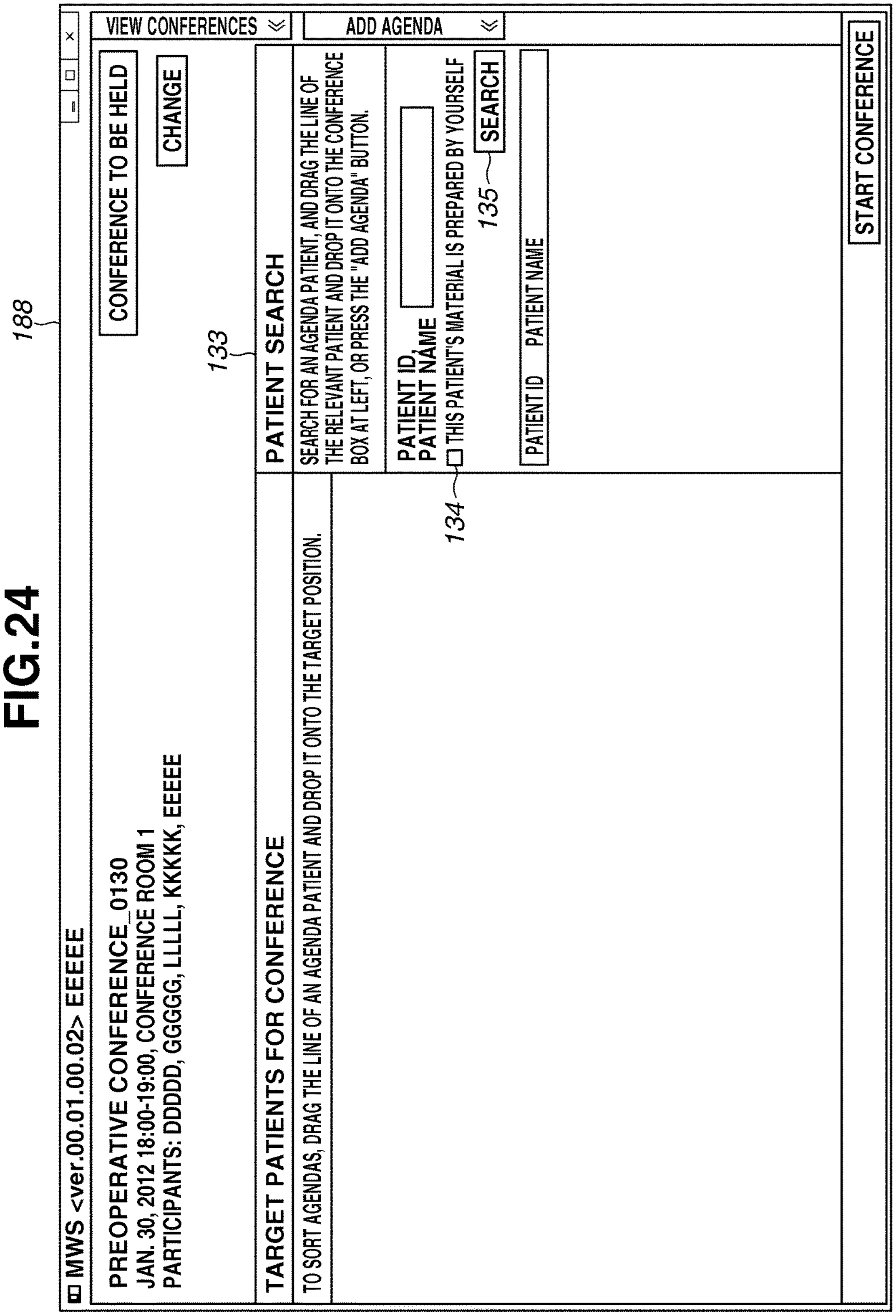

□ MWS <ver.00.01.00.02> EEEEE

PREOPERATIVE CONFERENCE_0130
JAN. 30, 2012 18:00-19:00, CONFERENCE ROOM 1
PARTICIPANTS: DDDDD, GGGGG, LLLLL, KKKKK, EEEEE

| VIEW CONFERENCES ≫ | ADD AGENDA ≫ |

CONFERENCE TO BE HELD  CHANGE

133

TARGET PATIENTS FOR CONFERENCE

TO SORT AGENDAS, DRAG THE LINE OF AN AGENDA PATIENT AND DROP IT ONTO THE TARGET POSITION.

PATIENT SEARCH

SEARCH FOR AN AGENDA PATIENT, AND DRAG THE LINE OF THE RELEVANT PATIENT AND DROP IT ONTO THE CONFERENCE BOX AT LEFT, OR PRESS THE "ADD AGENDA" BUTTON.

PATIENT ID
PATIENT NAME
☐ THIS PATIENT'S MATERIAL IS PREPARED BY YOURSELF

135 — SEARCH

134

| PATIENT ID | PATIENT NAME |

START CONFERENCE

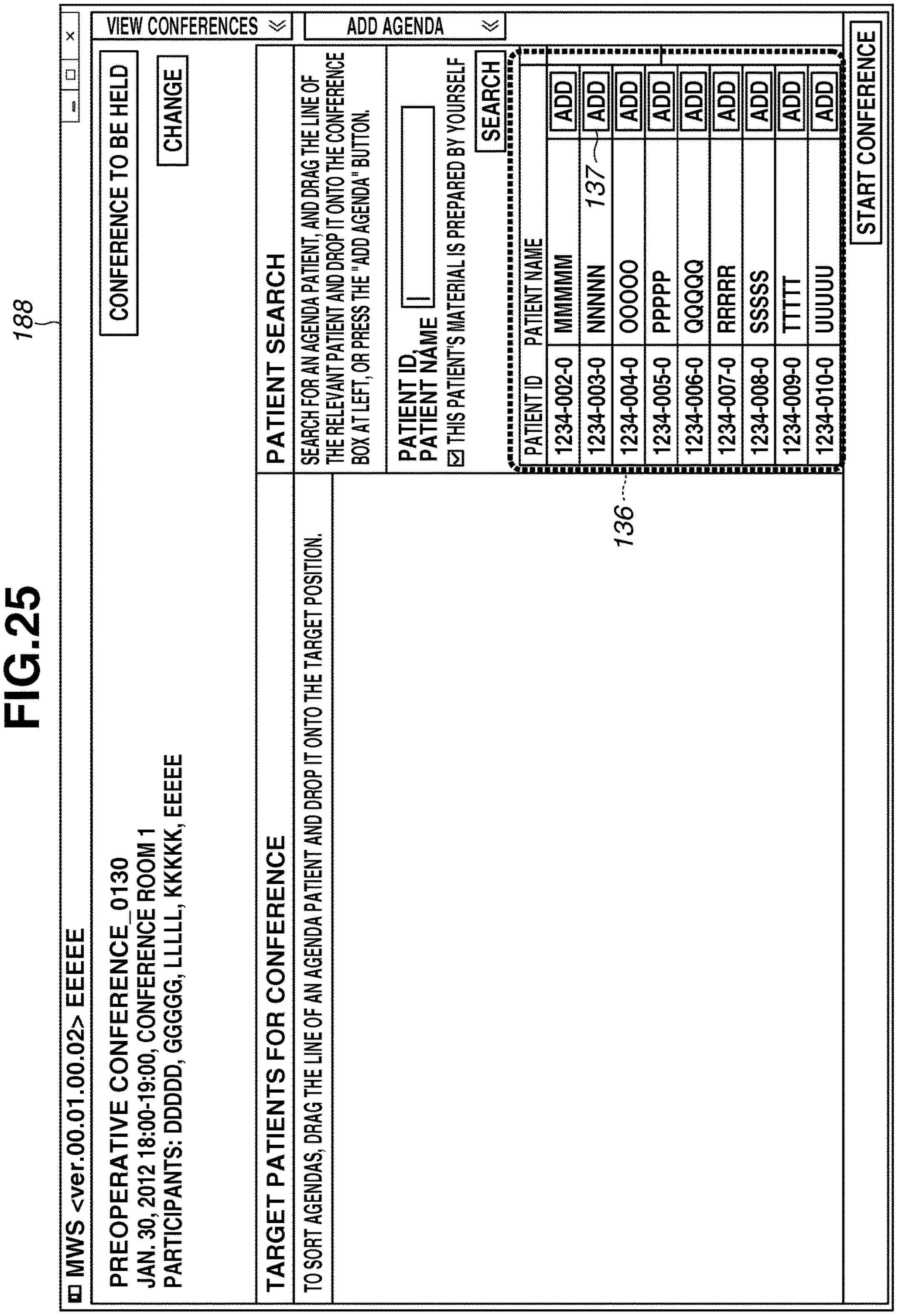

FIG.25

☐ MWS <ver.00.01.00.02> EEEEE

PREOPERATIVE CONFERENCE_0130
JAN. 30, 2012 18:00-19:00, CONFERENCE ROOM 1
PARTICIPANTS: DDDDD, GGGGG, LLLLL, KKKKK, EEEEE

188

CONFERENCE TO BE HELD | CHANGE

| VIEW CONFERENCES ≫ | ADD AGENDA ≫ |

TARGET PATIENTS FOR CONFERENCE
TO SORT AGENDAS, DRAG THE LINE OF AN AGENDA PATIENT AND DROP IT ONTO THE TARGET POSITION.

PATIENT SEARCH
SEARCH FOR AN AGENDA PATIENT, AND DRAG THE LINE OF THE RELEVANT PATIENT AND DROP IT ONTO THE CONFERENCE BOX AT LEFT, OR PRESS THE "ADD AGENDA" BUTTON.

PATIENT ID,
PATIENT NAME [    ] SEARCH

☑ THIS PATIENT'S MATERIAL IS PREPARED BY YOURSELF

| PATIENT ID | PATIENT NAME | |
|---|---|---|
| 1234-002-0 | MMMMM | ADD |
| 1234-003-0 | NNNNN | ADD  137 |
| 1234-004-0 | OOOOO | ADD |
| 1234-005-0 | PPPPP | ADD |
| 1234-006-0 | QQQQQ | ADD |
| 1234-007-0 | RRRRR | ADD |
| 1234-008-0 | SSSSS | ADD |
| 1234-009-0 | TTTTT | ADD |
| 1234-010-0 | UUUUU | ADD |

136

START CONFERENCE

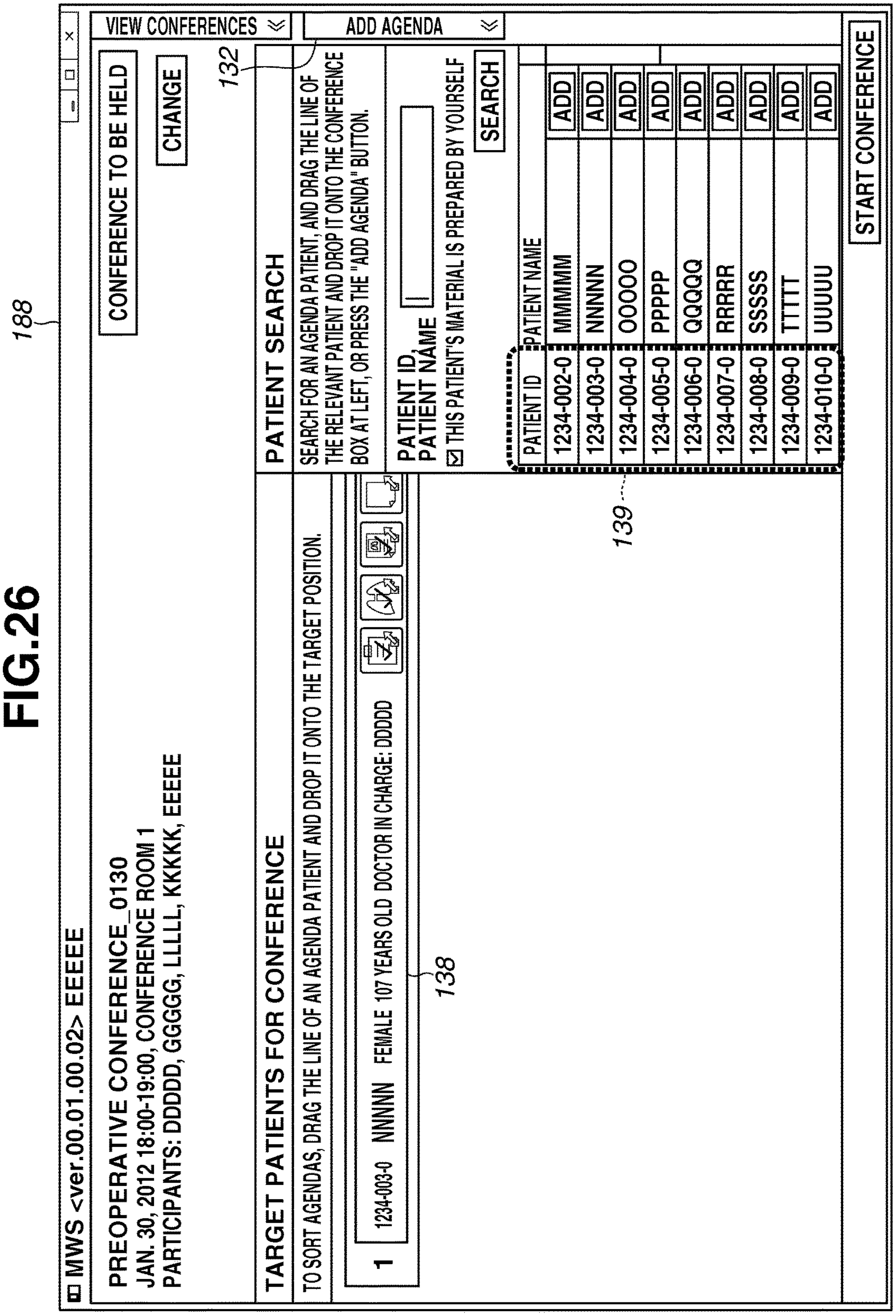

FIG.26

■ MWS <ver.00.01.00.02> EEEEE

PREOPERATIVE CONFERENCE_0130
JAN. 30, 2012 18:00-19:00, CONFERENCE ROOM 1
PARTICIPANTS: DDDDD, GGGGG, LLLLL, KKKKK, EEEEE

188

CONFERENCE TO BE HELD    [CHANGE]

132

TARGET PATIENTS FOR CONFERENCE

TO SORT AGENDAS, DRAG THE LINE OF AN AGENDA PATIENT AND DROP IT ONTO THE TARGET POSITION.

| 1 | 1234-003-0 | NNNNN | FEMALE 107 YEARS OLD DOCTOR IN CHARGE: DDDDD |

138

PATIENT SEARCH

SEARCH FOR AN AGENDA PATIENT, AND DRAG THE LINE OF
THE RELEVANT PATIENT AND DROP IT ONTO THE CONFERENCE
BOX AT LEFT, OR PRESS THE "ADD AGENDA" BUTTON.

PATIENT ID,
PATIENT NAME [      ]  [SEARCH]

☑ THIS PATIENT'S MATERIAL IS PREPARED BY YOURSELF

| PATIENT ID | PATIENT NAME | |
|---|---|---|
| 1234-002-0 | MMMMM | ADD |
| 1234-003-0 | NNNNN | ADD |
| 1234-004-0 | OOOOO | ADD |
| 1234-005-0 | PPPPP | ADD |
| 1234-006-0 | QQQQQ | ADD |
| 1234-007-0 | RRRRR | ADD |
| 1234-008-0 | SSSSS | ADD |
| 1234-009-0 | TTTTT | ADD |
| 1234-010-0 | UUUUU | ADD |

139

[VIEW CONFERENCES]    [ADD AGENDA]

[START CONFERENCE]

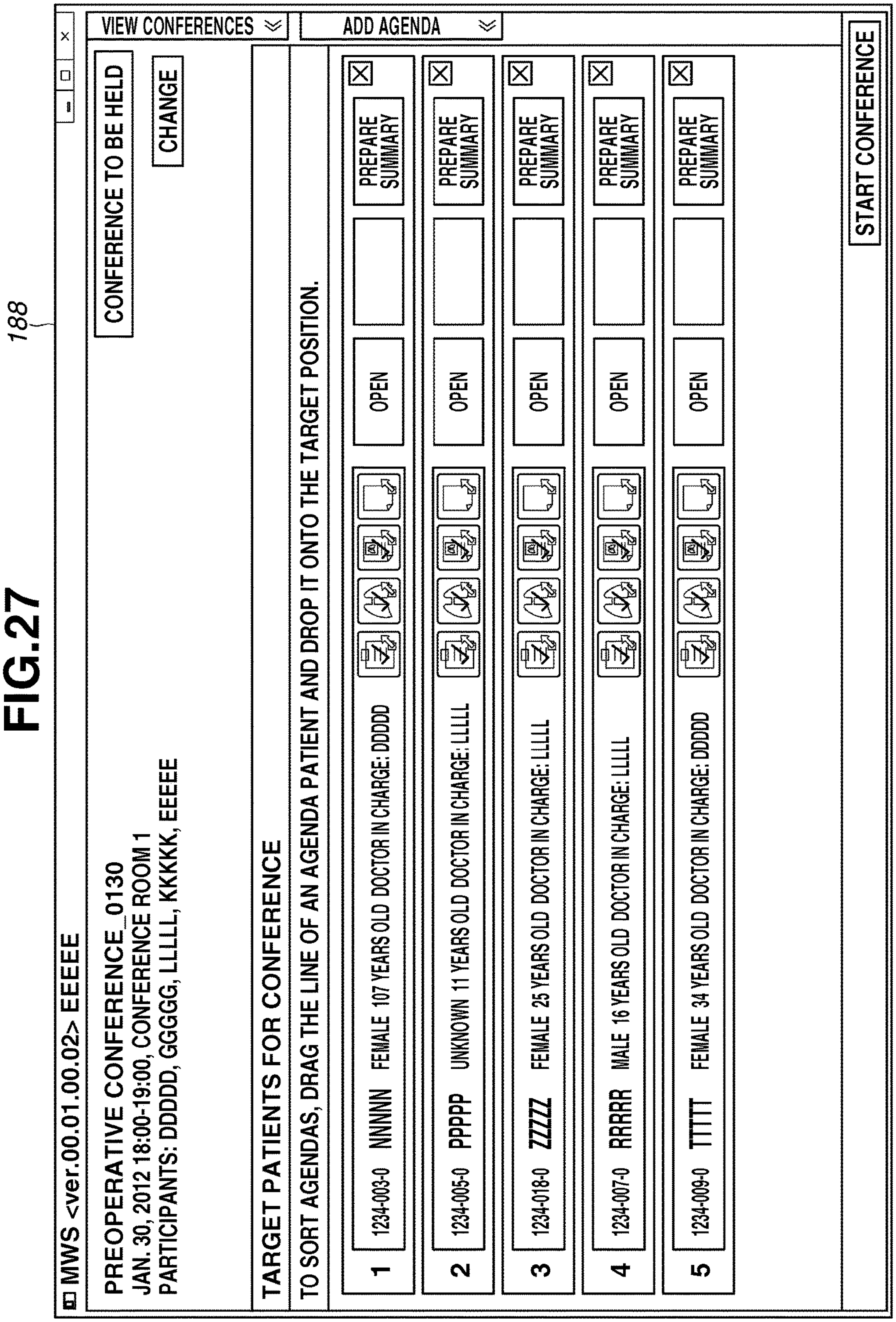

MWS <ver.00.01.00.02> EEEEE

PREOPERATIVE CONFERENCE_0130
JAN. 30, 2012 18:00-19:00, CONFERENCE ROOM 1
PARTICIPANTS: DDDDD, GGGGG, LLLLL, KKKKK, EEEEE

| VIEW CONFERENCES ⌄ | ADD AGENDA ⌄ | CONFERENCE TO BE HELD CHANGE |

TARGET PATIENTS FOR CONFERENCE
TO SORT AGENDAS, DRAG THE LINE OF AN AGENDA PATIENT AND DROP IT ONTO THE TARGET POSITION.

| # | ID | Name | Details | | OPEN | PREPARE SUMMARY |
|---|---|---|---|---|---|---|
| 1 | 1234-003-0 | NNNNN | FEMALE 107 YEARS OLD DOCTOR IN CHARGE: DDDDD | | OPEN | PREPARE SUMMARY |
| 2 | 1234-005-0 | PPPPP | UNKNOWN 11 YEARS OLD DOCTOR IN CHARGE: LLLLL | | OPEN | PREPARE SUMMARY |
| 3 | 1234-018-0 | ZZZZZ | FEMALE 25 YEARS OLD DOCTOR IN CHARGE: LLLLL | | OPEN | PREPARE SUMMARY |
| 4 | 1234-007-0 | RRRRR | MALE 16 YEARS OLD DOCTOR IN CHARGE: LLLLL | | OPEN | PREPARE SUMMARY |
| 5 | 1234-009-0 | TTTTT | FEMALE 34 YEARS OLD DOCTOR IN CHARGE: DDDDD | | OPEN | PREPARE SUMMARY |

START CONFERENCE

FIG.29

| DATA NAME | DATA CONTENTS |
|---|---|
| TERMINAL USED TO REGISTER MATERIAL | PC1 |
| PERSON WHO REGISTERED MATERIAL | DR. J |
| REGISTRATION TARGET BINDER | PATIENT NAME: MR. A |
| BINDER MATERIAL ID | 0000000315 |
| LOCATION OF REGISTERED MATERIAL | C:¥CONFERENCE MATERIAL¥IMAGE X.JPG |
| DATE OF MATERIAL PREPARATION | FEB. 08, 2012 |

FIG.30

| DATA NAME | DATA CONTENTS |
|---|---|
| CONFERENCE NAME | CONFERENCE M |
| CONFERENCE ID | 817 |
| PLANNED ATTENDANCES | DR. J, DR. K, DR, L |
| PLANNED DATE AND TIME | DEC. 30, 2011 11:00-12:00 |
| PLANNED PLACE | CONFERENCE ROOM 1 |
| ATTENDANCES | DR. J AND DR. K |
| DATE AND TIME OF CONFERENCE | DEC. 30, 2011 11:05-NOT DETERMINED (CONFERENCE IN PROGRESS) |
| PLACE OF CONFERENCE | CONFERENCE ROOM 1, CONFERENCE ROOM 2 (OTHER SITE) |
| USE OF IMAGE SHARING | YES |
| AGENDA LIST | PATIENT NAME: MR. A, MR. B, MR. C, MR. D |

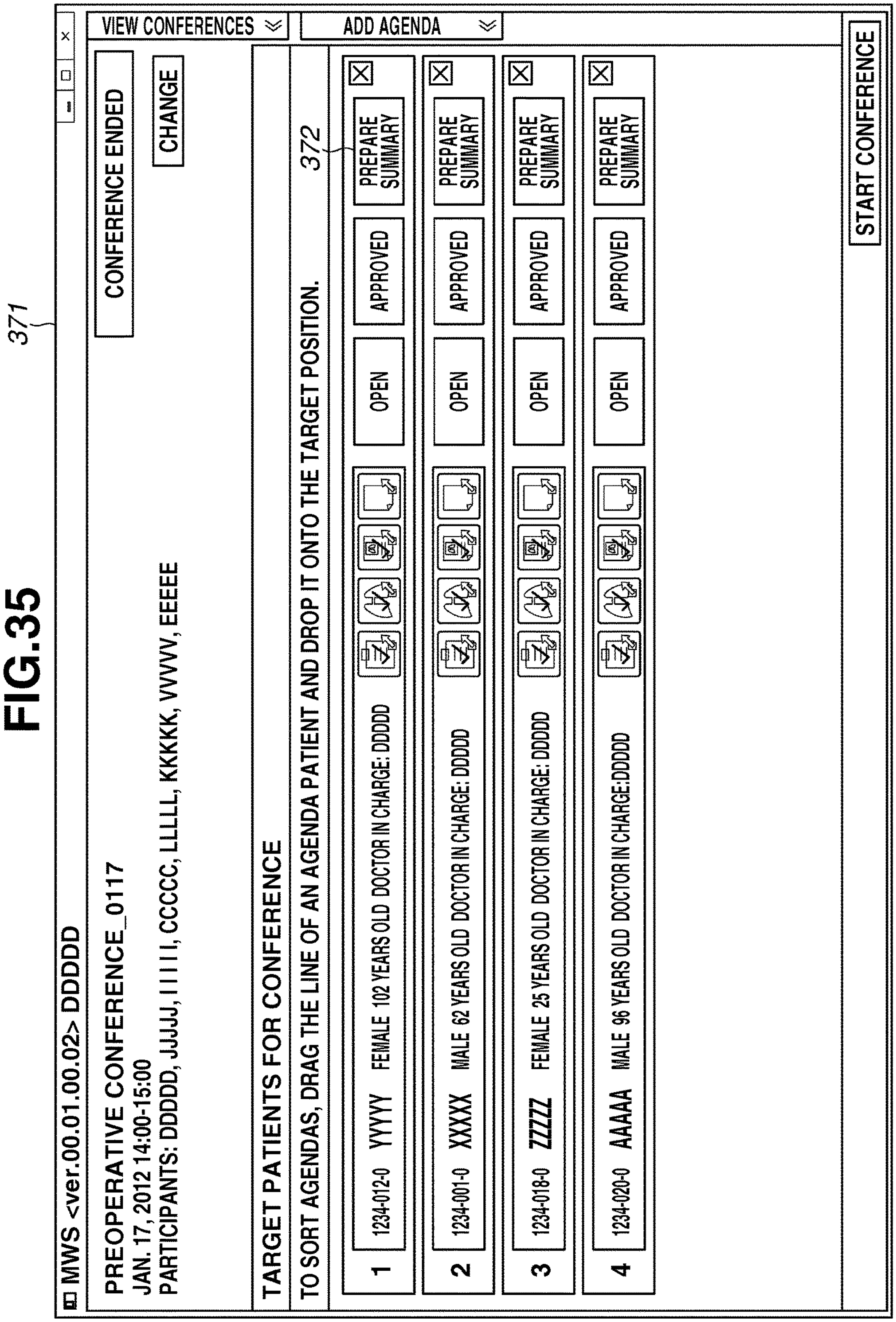

FIG.35

| MWS <ver.00.01.00.02> DDDDD | | | | | | | | |
|---|---|---|---|---|---|---|---|---|
| PREOPERATIVE CONFERENCE_0117 — 371 | | | | | VIEW CONFERENCES ⌄ | ADD AGENDA ⌄ | | |
| JAN. 17, 2012 14:00-15:00 | | | | | CONFERENCE ENDED | | | |
| PARTICIPANTS: DDDDD, JJJJJ, IIIII, CCCCC, LLLLL, KKKKK, VVVVV, EEEEE | | | | | CHANGE | | | |

TARGET PATIENTS FOR CONFERENCE
TO SORT AGENDAS, DRAG THE LINE OF AN AGENDA PATIENT AND DROP IT ONTO THE TARGET POSITION.  — 372

| | | | | | | | | |
|---|---|---|---|---|---|---|---|---|
| 1 | 1234-012-0 | YYYYY | FEMALE | 102 YEARS OLD | DOCTOR IN CHARGE: DDDDD | OPEN | APPROVED | PREPARE SUMMARY |
| 2 | 1234-001-0 | XXXXX | MALE | 62 YEARS OLD | DOCTOR IN CHARGE: DDDDD | OPEN | APPROVED | PREPARE SUMMARY |
| 3 | 1234-018-0 | ZZZZZ | FEMALE | 25 YEARS OLD | DOCTOR IN CHARGE: DDDDD | OPEN | APPROVED | PREPARE SUMMARY |
| 4 | 1234-020-0 | AAAAA | MALE | 96 YEARS OLD | DOCTOR IN CHARGE: DDDDD | OPEN | APPROVED | PREPARE SUMMARY |

START CONFERENCE

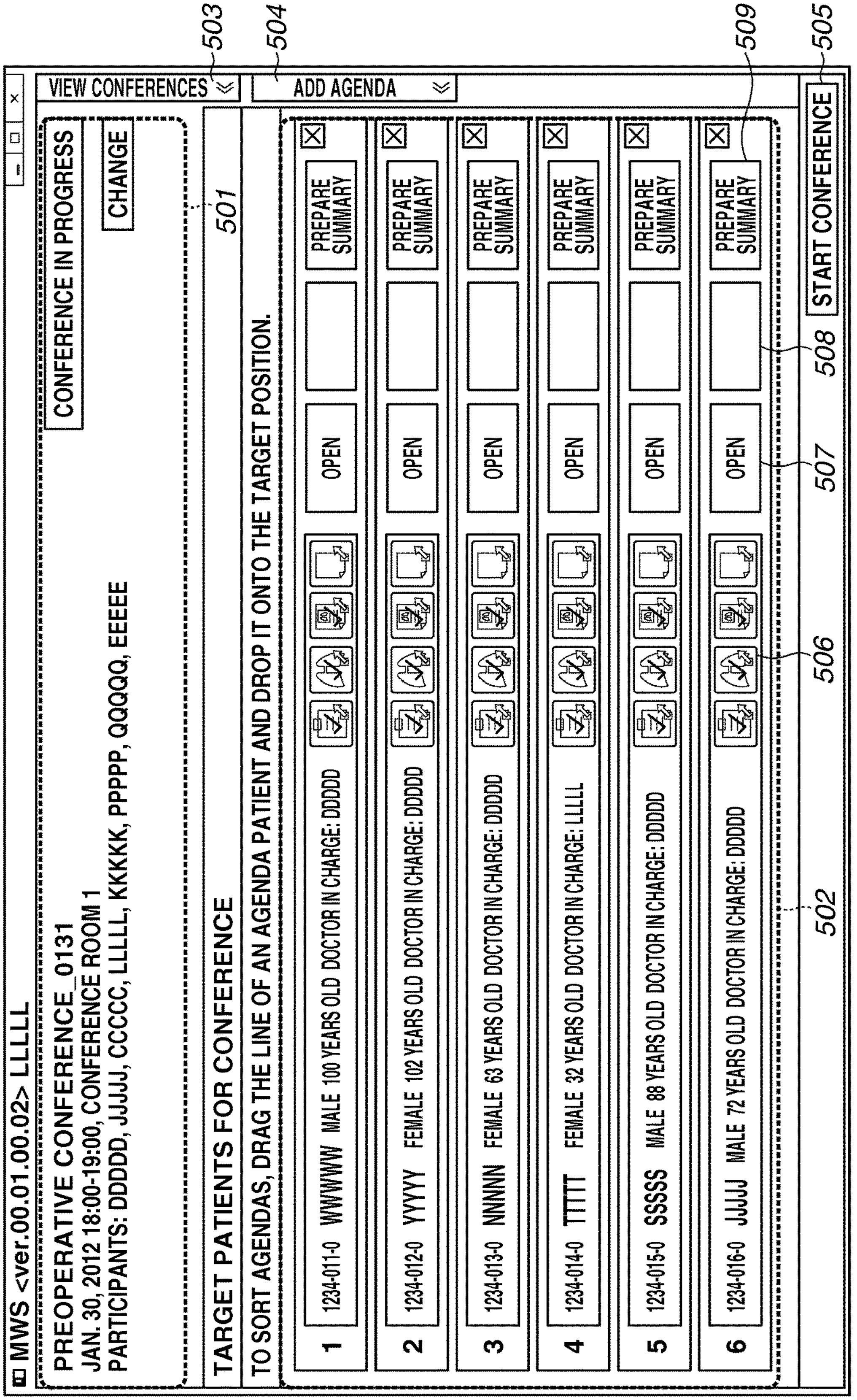

FIG.39A

MWS <ver.00.01.00.02> LLLLL

PREOPERATIVE CONFERENCE_0131
JAN. 30, 2012 18:00-19:00, CONFERENCE ROOM 1
PARTICIPANTS: DDDDD, JJJJJ, CCCCC, LLLLL, KKKKK, PPPPP, QQQQQ, EEEEE

CONFERENCE IN PROGRESS — CHANGE — 501

TARGET PATIENTS FOR CONFERENCE

TO SORT AGENDAS, DRAG THE LINE OF AN AGENDA PATIENT AND DROP IT ONTO THE TARGET POSITION.

VIEW CONFERENCES — 503
ADD AGENDA — 504
START CONFERENCE — 505

| | | | 506 | 507 | 508 | |
|---|---|---|---|---|---|---|
| 1 | 1234-011-0 WWWWW MALE 100 YEARS OLD DOCTOR IN CHARGE: DDDDD | | | OPEN | | PREPARE SUMMARY ☒ |
| 2 | 1234-012-0 YYYYY FEMALE 102 YEARS OLD DOCTOR IN CHARGE: DDDDD | | | OPEN | | PREPARE SUMMARY ☒ |
| 3 | 1234-013-0 NNNNN FEMALE 63 YEARS OLD DOCTOR IN CHARGE: DDDDD | | | OPEN | | PREPARE SUMMARY ☒ |
| 4 | 1234-014-0 TTTTT FEMALE 32 YEARS OLD DOCTOR IN CHARGE: LLLLL | | | OPEN | | PREPARE SUMMARY ☒ |
| 5 | 1234-015-0 SSSSS MALE 88 YEARS OLD DOCTOR IN CHARGE: DDDDD | | | OPEN | | PREPARE SUMMARY ☒ |
| 6 | 1234-016-0 JJJJJ MALE 72 YEARS OLD DOCTOR IN CHARGE: DDDDD | | | | | |

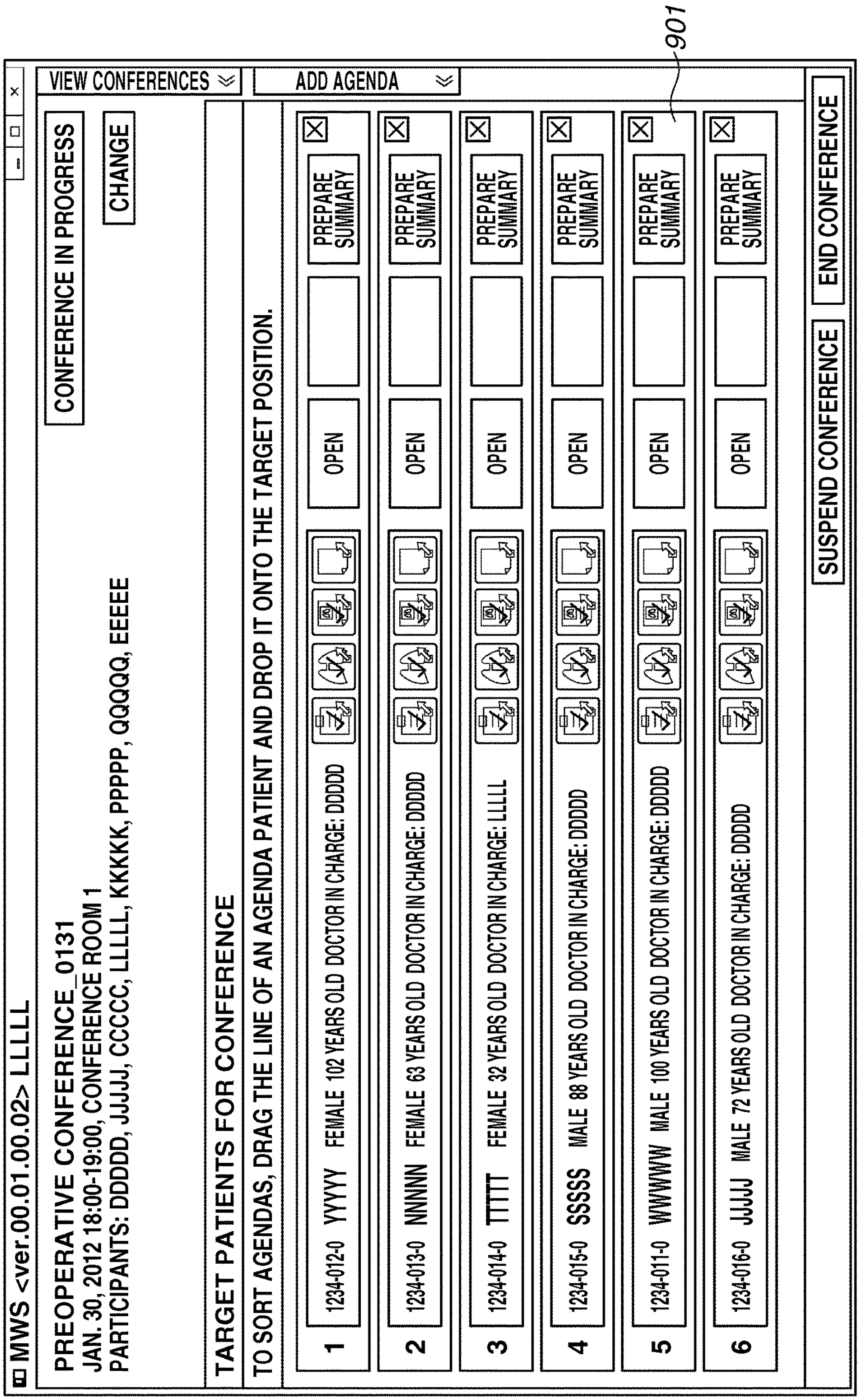

FIG.39E

MWS <ver.00.01.00.02> LLLLL

PREOPERATIVE CONFERENCE_0131
JAN. 30, 2012 18:00-19:00, CONFERENCE ROOM 1
PARTICIPANTS: DDDDD, JJJJJ, CCCCC, LLLLL, KKKKK, PPPPP, QQQQQ, EEEEE

CONFERENCE IN PROGRESS [CHANGE]

| VIEW CONFERENCES ⌄ | ADD AGENDA ⌄ |

TARGET PATIENTS FOR CONFERENCE
TO SORT AGENDAS, DRAG THE LINE OF AN AGENDA PATIENT AND DROP IT ONTO THE TARGET POSITION.

| # | Patient ID | Name | Sex | Age | Doctor | | Open | Prepare Summary |
|---|---|---|---|---|---|---|---|---|
| 1 | 1234-012-0 | YYYYY | FEMALE | 102 YEARS OLD | DOCTOR IN CHARGE: DDDDD | | OPEN | PREPARE SUMMARY ☒ |
| 2 | 1234-013-0 | NNNNN | FEMALE | 63 YEARS OLD | DOCTOR IN CHARGE: DDDDD | | OPEN | PREPARE SUMMARY ☒ |
| 3 | 1234-014-0 | TTTTT | FEMALE | 32 YEARS OLD | DOCTOR IN CHARGE: LLLLL | | OPEN | PREPARE SUMMARY ☒ |
| 4 | 1234-015-0 | SSSSS | MALE | 88 YEARS OLD | DOCTOR IN CHARGE: DDDDD | | OPEN | PREPARE SUMMARY ☒ |
| 5 | 1234-011-0 | WWWWW | MALE | 100 YEARS OLD | DOCTOR IN CHARGE: DDDDD | | OPEN | PREPARE SUMMARY ☒ —901 |
| 6 | 1234-016-0 | JJJJJ | MALE | 72 YEARS OLD | DOCTOR IN CHARGE: DDDDD | | OPEN | PREPARE SUMMARY ☒ |

[SUSPEND CONFERENCE] [END CONFERENCE]

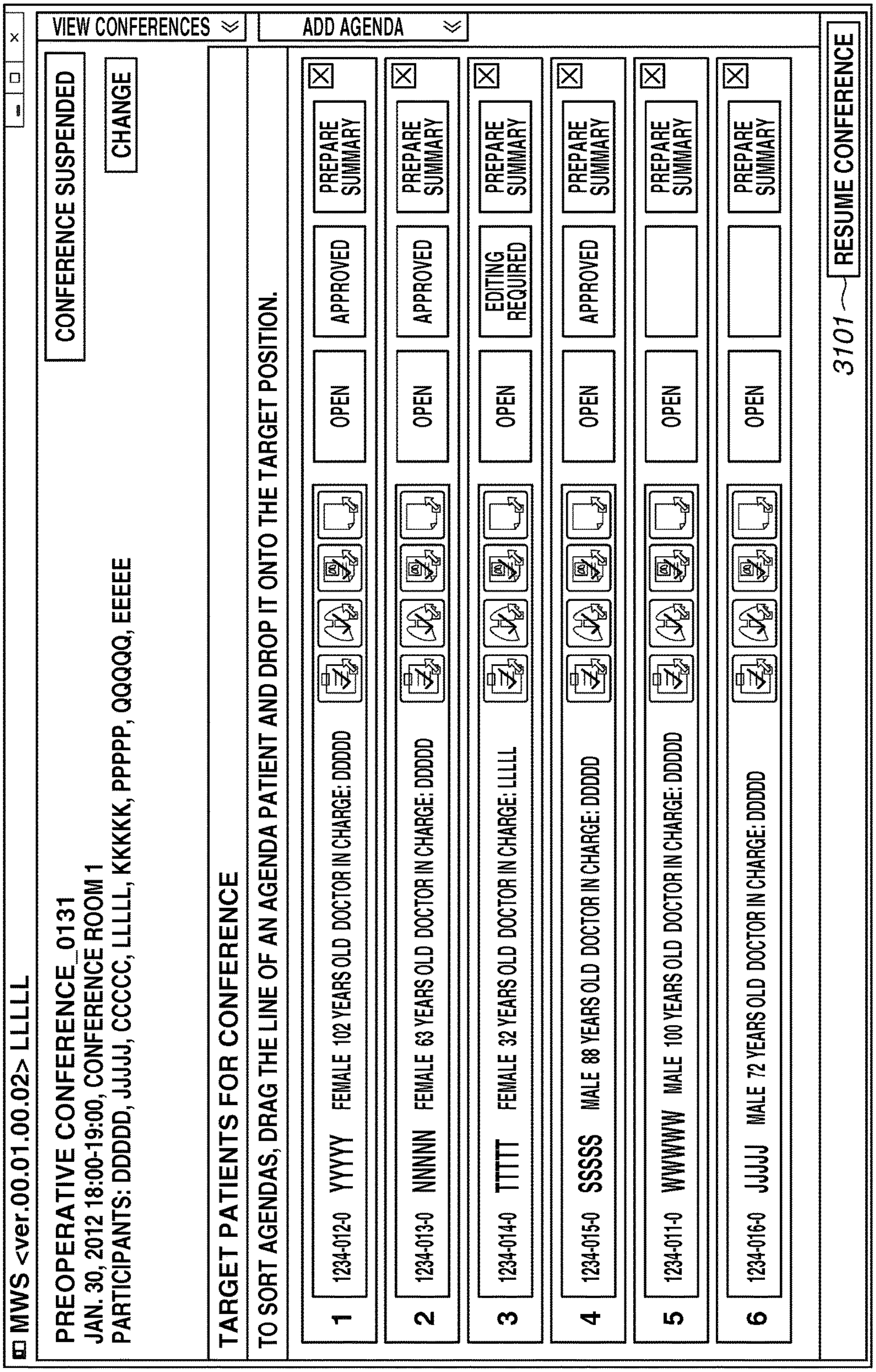

FIG.47B

□ MWS <ver.00.01.00.02> LLLLL

PREOPERATIVE CONFERENCE_0131
JAN. 30, 2012 18:00-19:00, CONFERENCE ROOM 1
PARTICIPANTS: DDDDD, JJJJJ, CCCCC, LLLLL, KKKKK, PPPPP, QQQQQ, EEEEE

CONFERENCE SUSPENDED | CHANGE

VIEW CONFERENCES ≫ | ADD AGENDA ≫

TARGET PATIENTS FOR CONFERENCE
TO SORT AGENDAS, DRAG THE LINE OF AN AGENDA PATIENT AND DROP IT ONTO THE TARGET POSITION.

| # | ID | Name | Details | | | | Status | Action | |
|---|---|---|---|---|---|---|---|---|---|
| 1 | 1234-012-0 | YYYYY | FEMALE 102 YEARS OLD DOCTOR IN CHARGE: DDDDD | | | | OPEN | APPROVED | PREPARE SUMMARY | ☒ |
| 2 | 1234-013-0 | NNNNN | FEMALE 63 YEARS OLD DOCTOR IN CHARGE: DDDDD | | | | OPEN | APPROVED | PREPARE SUMMARY | ☒ |
| 3 | 1234-014-0 | TTTTT | FEMALE 32 YEARS OLD DOCTOR IN CHARGE: LLLLL | | | | OPEN | EDITING REQUIRED | PREPARE SUMMARY | ☒ |
| 4 | 1234-015-0 | SSSSS | MALE 88 YEARS OLD DOCTOR IN CHARGE: DDDDD | | | | OPEN | APPROVED | PREPARE SUMMARY | ☒ |
| 5 | 1234-011-0 | WWWWW | MALE 100 YEARS OLD DOCTOR IN CHARGE: DDDDD | | | | OPEN | | PREPARE SUMMARY | ☒ |
| 6 | 1234-016-0 | JJJJJ | MALE 72 YEARS OLD DOCTOR IN CHARGE: DDDDD | | | | OPEN | | PREPARE SUMMARY | ☒ |

3101 — RESUME CONFERENCE

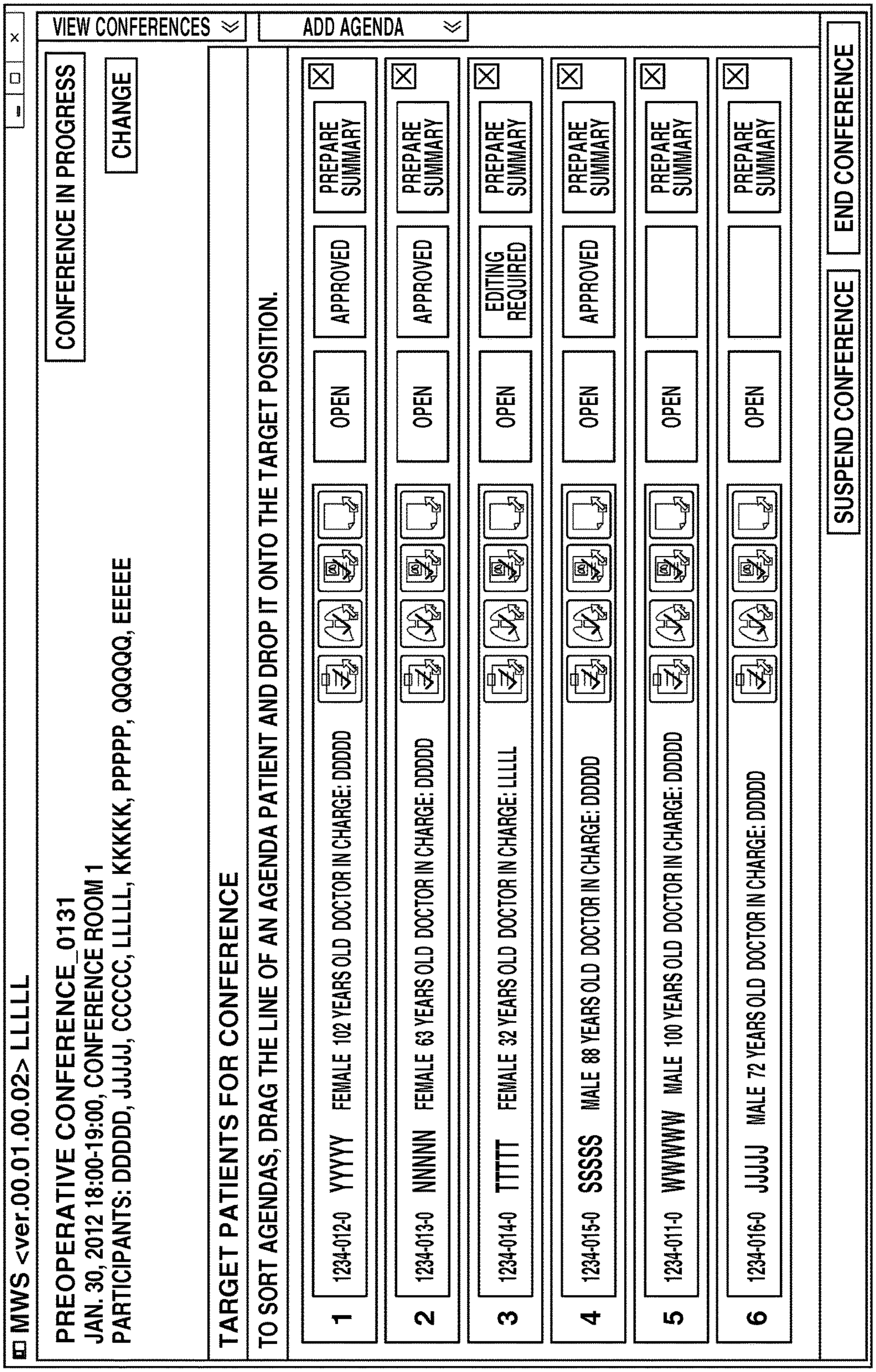

FIG. 47C

MWS <ver.00.01.00.02> LLLLL

PREOPERATIVE CONFERENCE_0131
JAN. 30, 2012 18:00-19:00, CONFERENCE ROOM 1
PARTICIPANTS: DDDDD, JJJJJ, CCCCC, LLLLL, KKKKK, PPPPP, QQQQQ, EEEEE

VIEW CONFERENCES | ADD AGENDA

CONFERENCE IN PROGRESS | CHANGE

TARGET PATIENTS FOR CONFERENCE
TO SORT AGENDAS, DRAG THE LINE OF AN AGENDA PATIENT AND DROP IT ONTO THE TARGET POSITION.

| # | ID | Name | Details | | | | Status | Action |
|---|---|---|---|---|---|---|---|---|
| 1 | 1234-012-0 | YYYYY | FEMALE 102 YEARS OLD DOCTOR IN CHARGE: DDDDD | | | | OPEN | APPROVED | PREPARE SUMMARY |
| 2 | 1234-013-0 | NNNNN | FEMALE 63 YEARS OLD DOCTOR IN CHARGE: DDDDD | | | | OPEN | APPROVED | PREPARE SUMMARY |
| 3 | 1234-014-0 | TTTTT | FEMALE 32 YEARS OLD DOCTOR IN CHARGE: LLLLL | | | | OPEN | EDITING REQUIRED | PREPARE SUMMARY |
| 4 | 1234-015-0 | SSSSS | MALE 88 YEARS OLD DOCTOR IN CHARGE: DDDDD | | | | OPEN | APPROVED | PREPARE SUMMARY |
| 5 | 1234-011-0 | WWWWW | MALE 100 YEARS OLD DOCTOR IN CHARGE: DDDDD | | | | OPEN | | PREPARE SUMMARY |
| 6 | 1234-016-0 | JJJJJ | MALE 72 YEARS OLD DOCTOR IN CHARGE: DDDDD | | | | OPEN | | PREPARE SUMMARY |

SUSPEND CONFERENCE | END CONFERENCE

CONFERENCE PREPARATION APPARATUS, CONFERENCE PREPARATION METHOD, AND STORAGE MEDIUM

BACKGROUND OF THE INVENTION

Field of the Invention

The present invention relates to a medical conference preparation apparatus for efficiently preparing for a medical conference, and more particularly for preparing conference materials.

Description of the Related Art

Nowadays, many hospitals hold a medical conference in which doctors and medical staffs related to a target patient examine operative procedures prior to an operation. In the medical conference, the participants first confirm basic patient information and a Subjective, Objective, Assessment, Plan (SOAP) description of an electronic chart (electronic medical record). Then, the participants confirm an affected region while viewing Digital Imaging and Communication in Medicine (DICOM) images on a Picture Archiving and Communication Systems (PACS) viewer. Further, the participants refer to an examination report on radiogram diagnosis and pathology diagnosis by using a diagnostic reporting system.

In this case, however, during the conference, the participants need to open the page of the target patient in the electronic chart and also to activate the PACS viewer and other various material browsing applications each time. Thus, the conference cannot be smoothly advanced. There is a problem that a doctor in charge of the target patient cannot take much time to prepare for the conference because he or she is very busy. Japanese Patent Application Laid-Open No. 2005-43951 discusses a medical conference support system.

With the medical conference support system discussed in Japanese Patent Application Laid-Open No. 2005-43951, however, in addition to regular medical care and diagnosis, a doctor in charge needs to take much time to prepare for the conference particularly to prepare conference materials. For this reason, it has been impossible to easily prepare conference materials at the same timing as viewing a material during medical care and diagnosis.

SUMMARY OF THE INVENTION

The present invention is directed to providing a medical conference preparation system for enabling efficiently preparing for a medical conference without troublesome work.

According to an aspect of the present invention, a conference preparation apparatus includes a material identification information acquisition unit configured to acquire material identification information specified by an operation performed on a display screen, a material information acquisition unit configured to acquire material information from a server based on the material identification information acquired by the material identification information acquisition unit, a management unit configured to manage on a person-by-person basis the material information acquired by the material information acquisition unit, and an agenda management unit configured to associate the material identification information with conference items.

According to another aspect of the present invention, a conference support apparatus for supporting a medical conference includes a unit configured to acquire a template having a defined summary output pattern, a unit configured to acquire electronic chart information of a patient, a unit configured to acquire conference holding details for the patient, a unit configured to generate a summary of the electronic chart information and the conference holding details for the template and to store the summary in a file, and a unit configured to associate the stored summary with the patient.

According to yet another aspect of the present invention, a conference support apparatus for supporting a medical conference includes a unit configured to set patient examination data and an agenda for the conference, and a display control unit configured to, when a list of patient information is displayed as an agenda for the conference, display as an icon a conference material preparation status or conclusion status for the agenda.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 18 illustrates an example of a conference reservation screen.

FIG. 19 illustrates an example of a conference reservation screen.

FIG. 20 illustrates an example of a conference reservation screen.

FIG. 21 illustrates an example of a conference reservation screen.

FIG. 24 illustrates an example of a conference screen.

FIG. 25 illustrates an example of a conference screen.

FIG. 26 illustrates an example of a conference screen.

FIG. 27 illustrates an example of a conference screen.

FIG. 29 illustrates an example of material registration information.

FIG. 30 illustrates an example of conference information.

FIG. 35 illustrates a display screen of the conference client apparatus according to the second exemplary embodiment.

FIG. 39A illustrates a screen of the conference advancing unit of the conference client apparatus before starting a conference, FIG. 39E illustrates an operation for changing the order of agenda patients on the conference client apparatus.

FIG. 47B illustrates a state where a conference is suspended on the conference client apparatus, and FIG. 47C illustrates a state where the conference is resumed on the conference client apparatus.

DESCRIPTION OF THE EMBODIMENTS

Various exemplary embodiments, features, and aspects of the invention will be described in detail below with reference to the drawings.

Figure 1:
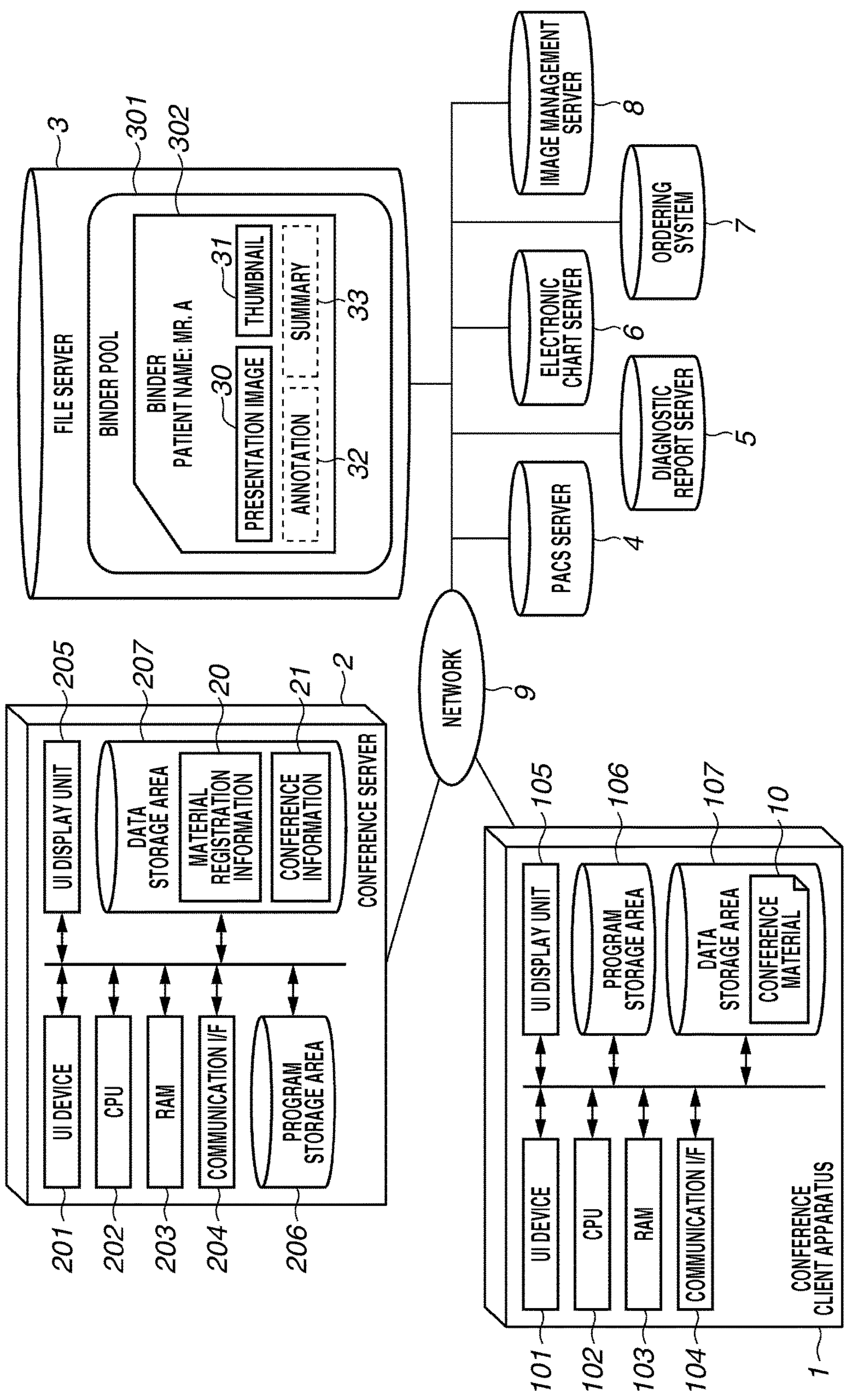
FIG. 1 illustrates a configuration of a conference preparation system for holding a medical conference according to a first exemplary embodiment.

FIG. 1 illustrates a configuration of a conference preparation system according to a first exemplary embodiment. The conference preparation system according to the first exemplary embodiment includes a conference client apparatus 1 and a conference server 2. The conference preparation system is connected with various servers (a file server 3, a PACS server 4, a diagnostic report server 5, an electronic chart server 6, an ordering system 7, and an image management server 8) in a hospital. There may be a plurality of the conference clients 1. Further, the conference client apparatus 1 may include the function of the conference server 2 to provide a peer-to-peer (P2P) configuration. The conference client apparatus 1, the conference server 2, and the above-described servers 3 to 8 in the hospital are connected via a wired or wireless network 9.

The conference client apparatus 1 will be described in detail below. The hardware configuration of the conference server 2 is similar to that of the conference client apparatus 1. A user interface (UI) device 101 is a mouse, a digitizer, or a keyboard which is used to input user instructions to the conference client apparatus 1. The conference client apparatus 1 includes a central processing unit (CPU) 102 and a random access memory (RAM) 103. When the CPU 102 loads a program from a program storage area 106 into the RAM 103 and then interprets and executes it, the conference client apparatus 1 is able to perform various control and calculations and display UIs. A communication interface (I/F) 104 connected with the network 9 serves as a communication interface between the conference client apparatus 1, the conference server 2, and the servers 3 to 8 in the hospital.

A UI display 105 is a light emitting diode (LED) display or a liquid crystal panel for displaying the status and processing of the conference client apparatus 1. The conference client apparatus 1 further includes the program storage area 106 and a data storage area 107. Although these two storage areas can be implemented by using a hard disk or a flash memory, the present invention does not depend on a specific storage medium. The conference client apparatus 1 stores a conference material 10 in the data storage area 107. The conference material 10 may be stored in the file server 3. The conference server 2 stores material registration information 20 and conference information 21 in a data storage area 207. An example of the material registration information 20 is illustrated in FIG. 29, and an example of the conference information 21 is illustrated in FIG. 30.

Conference materials are collected for each individual patient or case and managed on a binder basis. However, entities of conference materials are not stored in binders but only management information of conference materials is stored in binders. The file server 3 includes a binder pool 301 in which a binder 302 is generated for each individual patient or case. The binder pool 301 may be included in the data storage area 207 of the conference server 2. In each binder 302, a presentation image 30 and a thumbnail 31 are generated for each of registered materials. Since medical images are difficult to handle because of large sizes, the presentation image 30 more suitable for display during the conference is generated. Information of a handwritten note taken for an image during the conference is stored in each binder 302 as an annotation 32. Further, a document summarizing a conclusion of the conference and images used in the conference is stored in each binder 302 as a summary 33.

Figure 28:
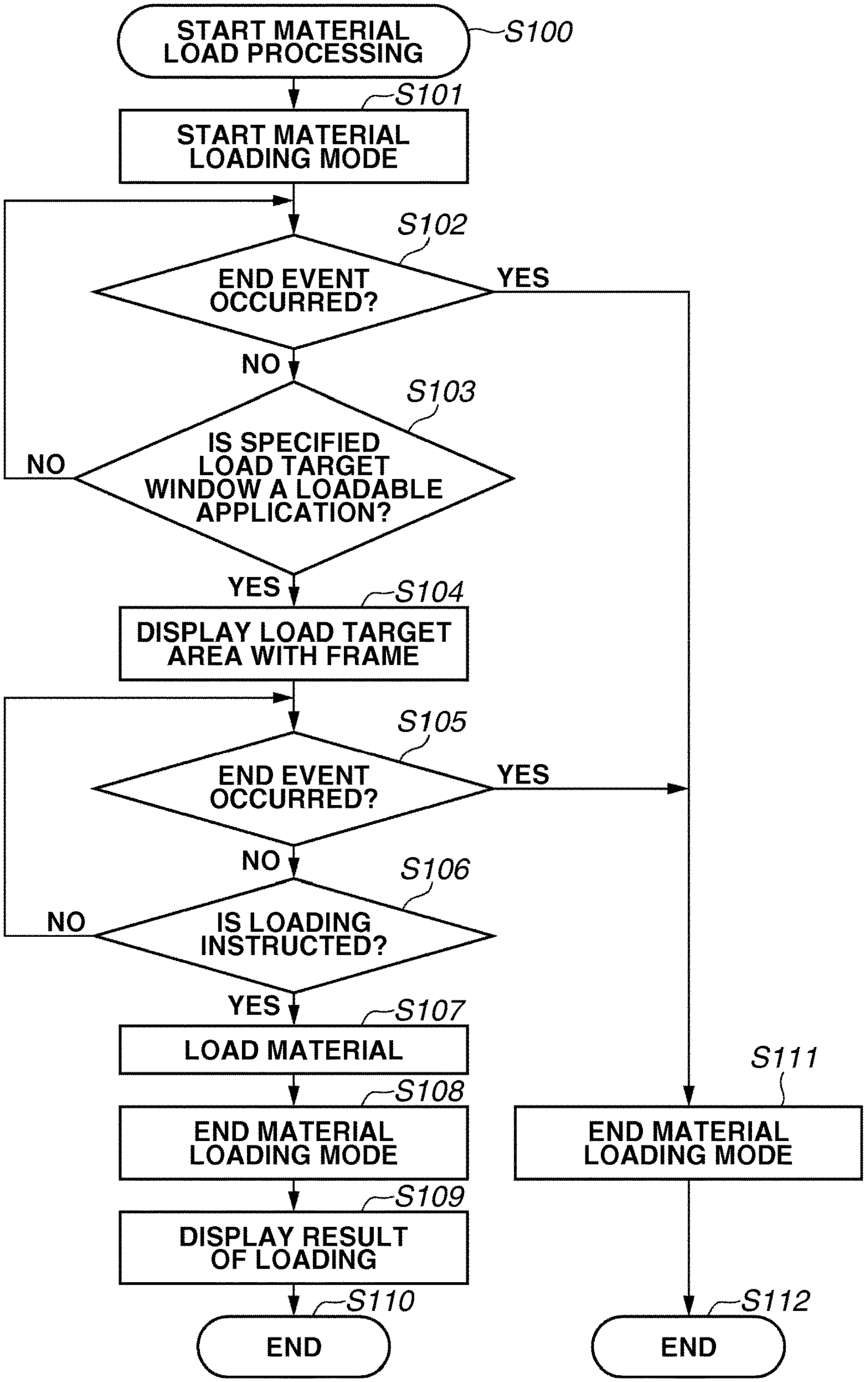
FIG. 28 is a flowchart illustrating material loading processing.

The following describes processing for loading a material performed by the conference preparation system with reference to the system configuration illustrated in FIG. 1, the flowchart illustrated in FIG. 28, and example screens illustrated in FIGS. 2 to 16. The following describes a use case where a doctor in charge of a certain patient performs medical care and diagnosis for the patient and at the same time prepares a material required for a medical conference, by operating the UI device 101 via a screen displayed on the UI display 105 of the conference client apparatus 1 illustrated in FIG. 1.

Figure 2:
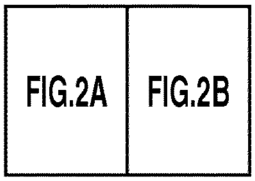
FIG. 2, which is composed of FIGS. 2A and 2B, illustrates an example screen before the material loading mode is activated.
Figure 2A:
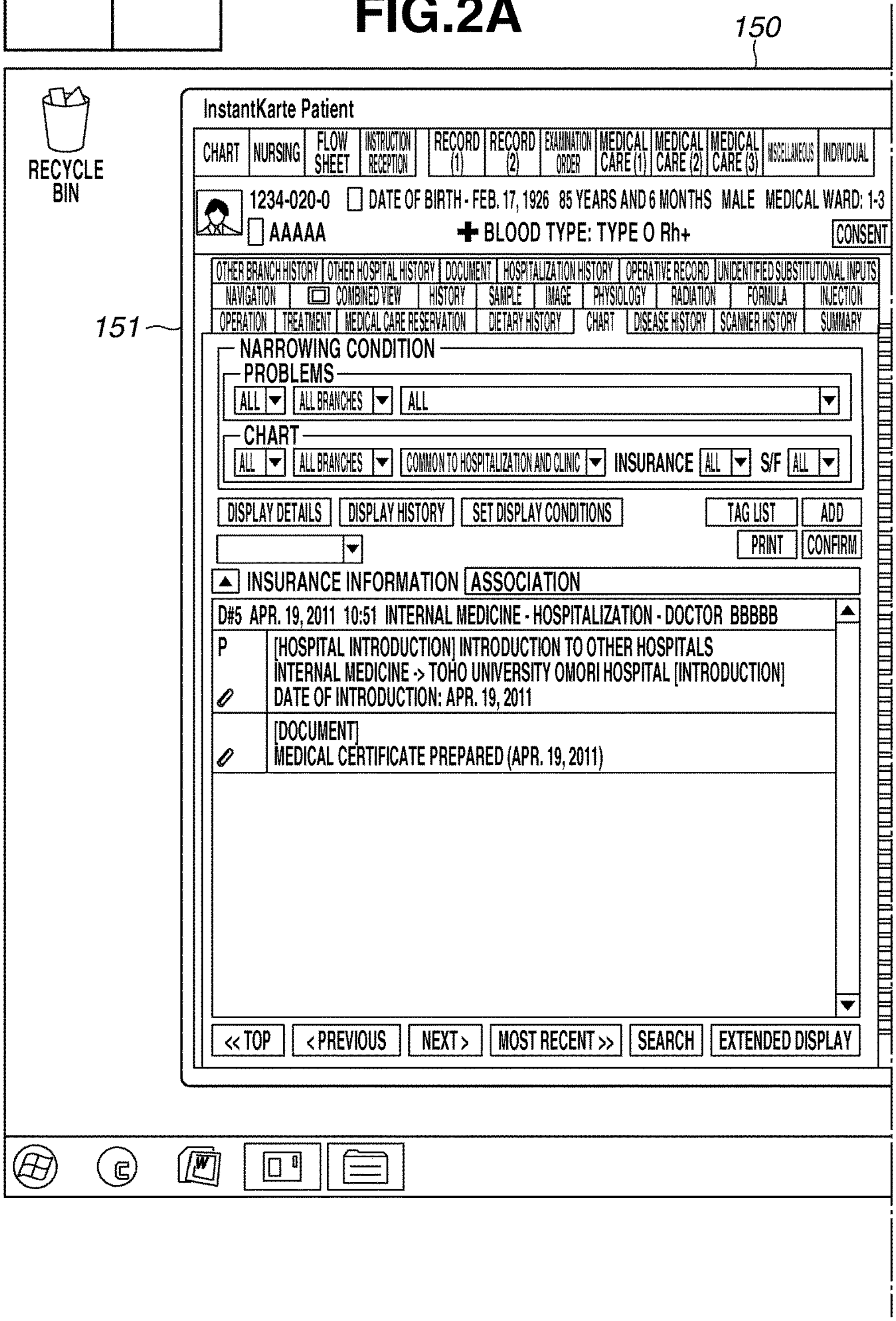
Figure 2B:
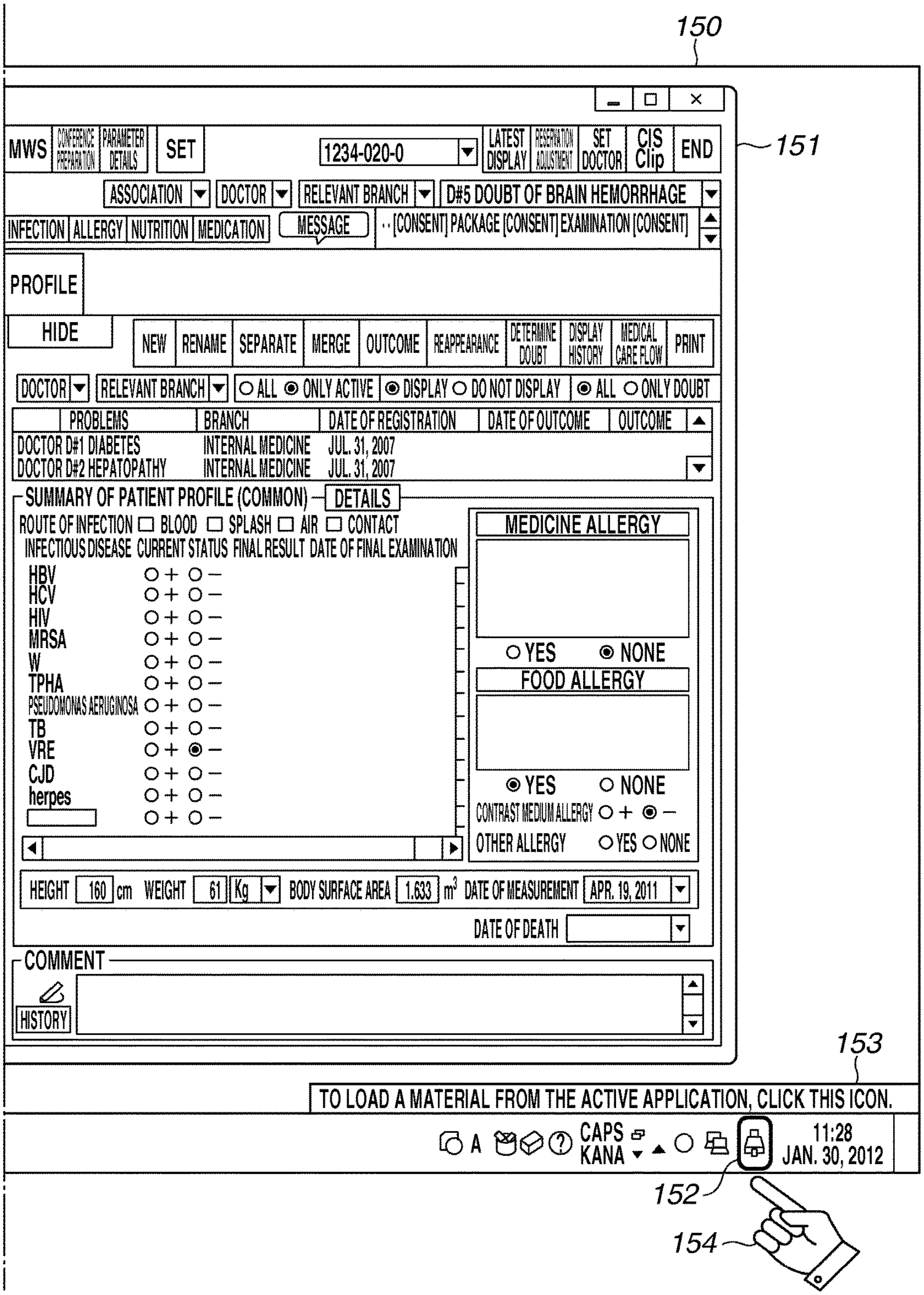

The following describes processing for loading basic patient information (material identification information) and a SOAP description from an electronic chart system 151 on a desktop screen 150 illustrated in FIG. 2. When the doctor in charge brings a pointing unit 154 close to a LOAD MATERIAL button 152, a guidance message is temporarily displayed, as illustrated by a pop-up 153. When the user clicks the LOAD MATERIAL button 152, the electronic chart system 151 starts material loading processing. Subsequently, the processing proceeds according to the flowchart illustrated in FIG. 28.

Figure 3:
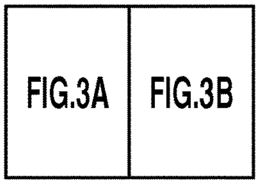
FIG. 3, which is composed of FIGS. 3A and 3B, illustrates an example screen after the material loading mode is activated.
Figure 3A:
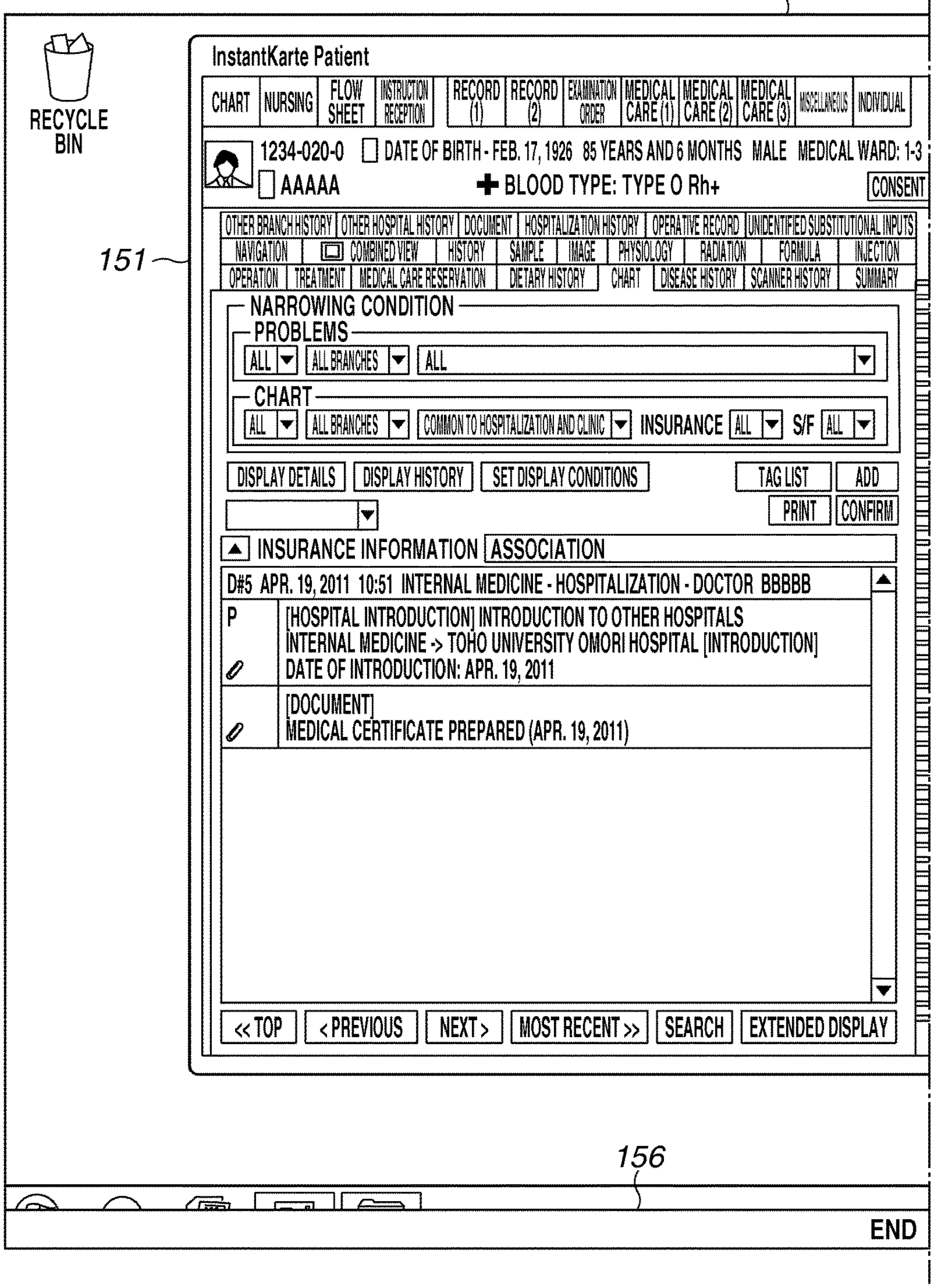

In step S101, when the material loading mode is activated, the desktop screen 150 is covered by a white semi-transparent window, as illustrated in FIG. 3, and a guidance is temporarily displayed, as illustrated by a pop-up 155. When a mode termination event, such as clicking an END button 156, is determined to have been generated in the material loading mode (YES in step S102), then in step S111, the conference preparation system exits the material loading mode. When the material loading mode ends, the semi-transparent white window disappears and then the former desktop screen 150 appears, as illustrated in FIG. 2.

Figure 4:
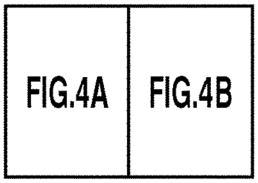
FIG. 4, which is composed of FIGS. 4A and 4B, illustrates an example screen after a load target material is specified.
Figure 4A:
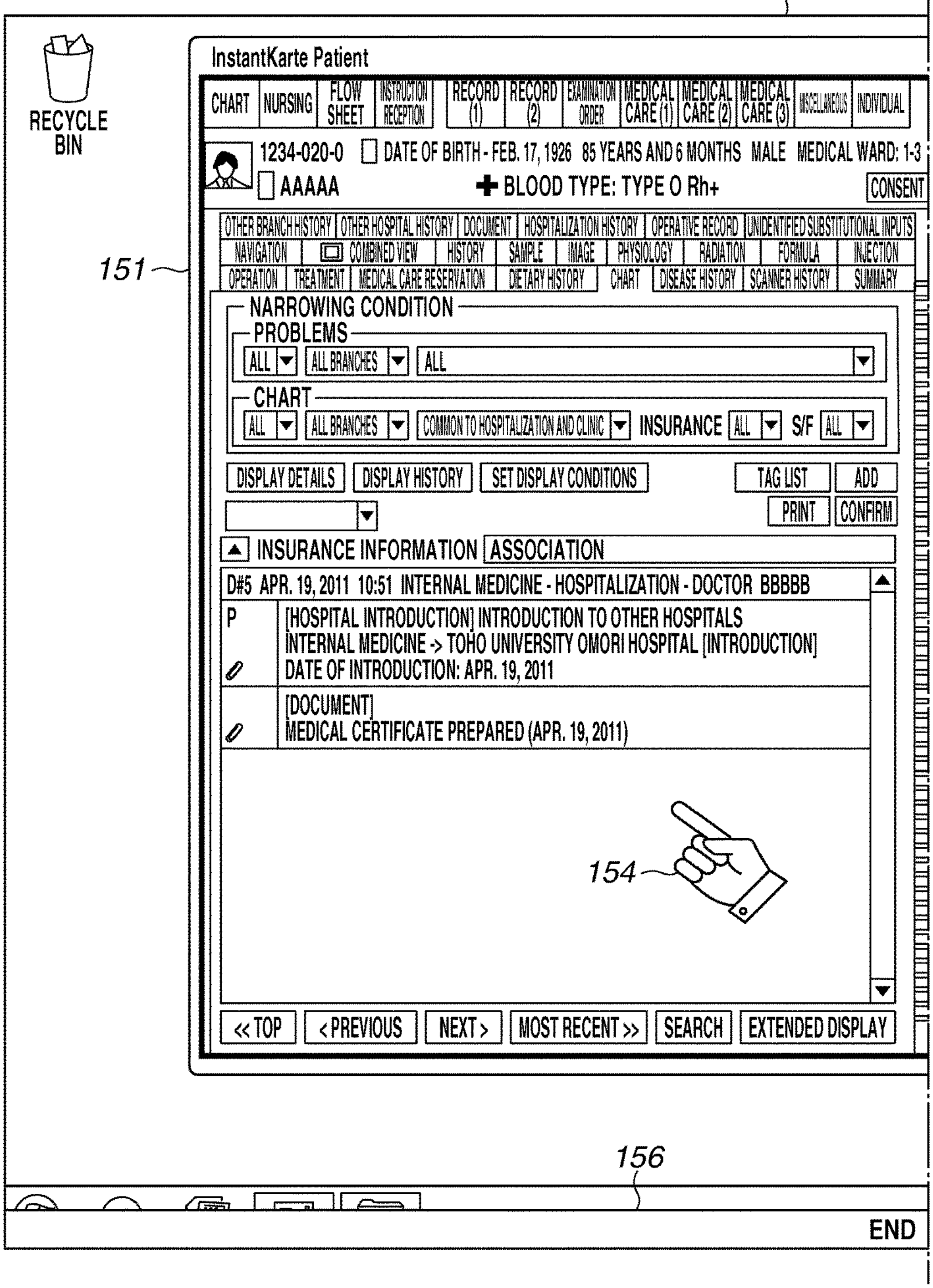

Then, in the material loading mode, when the user clicks the screen of the electronic chart system 151 by using the pointing unit 154, as illustrated in FIG. 4, a load target material is specified. A load target material may be specified by any method other than clicking. For example, a load target material may also be specified, for example, by bringing the pointing unit 154 over the load target material. When a load target window is specified, the electronic chart system 151 searches for the process of the window's owner based on the window handle and then determines whether the target application is a loadable application (in this case, the electronic chart system 151) based on the process name. When the target application is determined to be a loadable application (YES in step S103), then in step S104, the electronic chart system 151 encloses a load target area 157 with a red square frame. The method for specifying a load target area is not limited to enclosing it with a red square frame. For example, a hole may be made in the white semi-transparent window on the load target area 157. Then, when the user double-clicks or right-clicks the load target area 157 by using the pointing unit 154 to instruct to execute loading (YES in step S106), then in step S107, the electronic chart system 151 loads the material. The instruction for loading execution is not limited to double-clicking and right-clicking.

Figure 5:
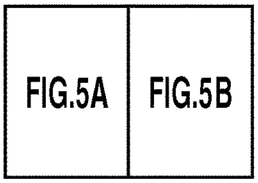
FIG. 5, which is composed of FIGS. 5A and 5B, illustrates an example screen displaying a result of loading the load target material.
Figure 5A:
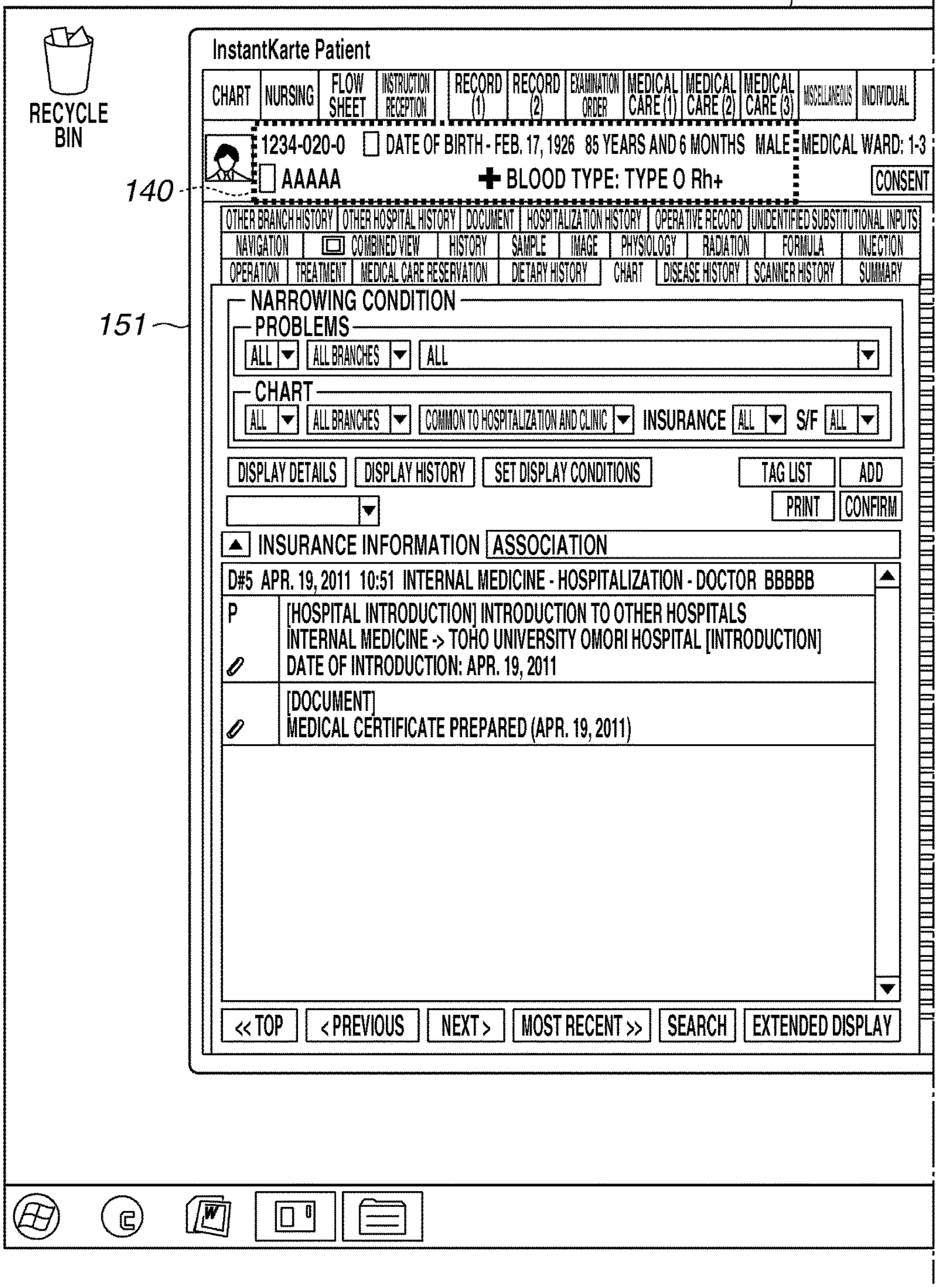
Figure 5B:
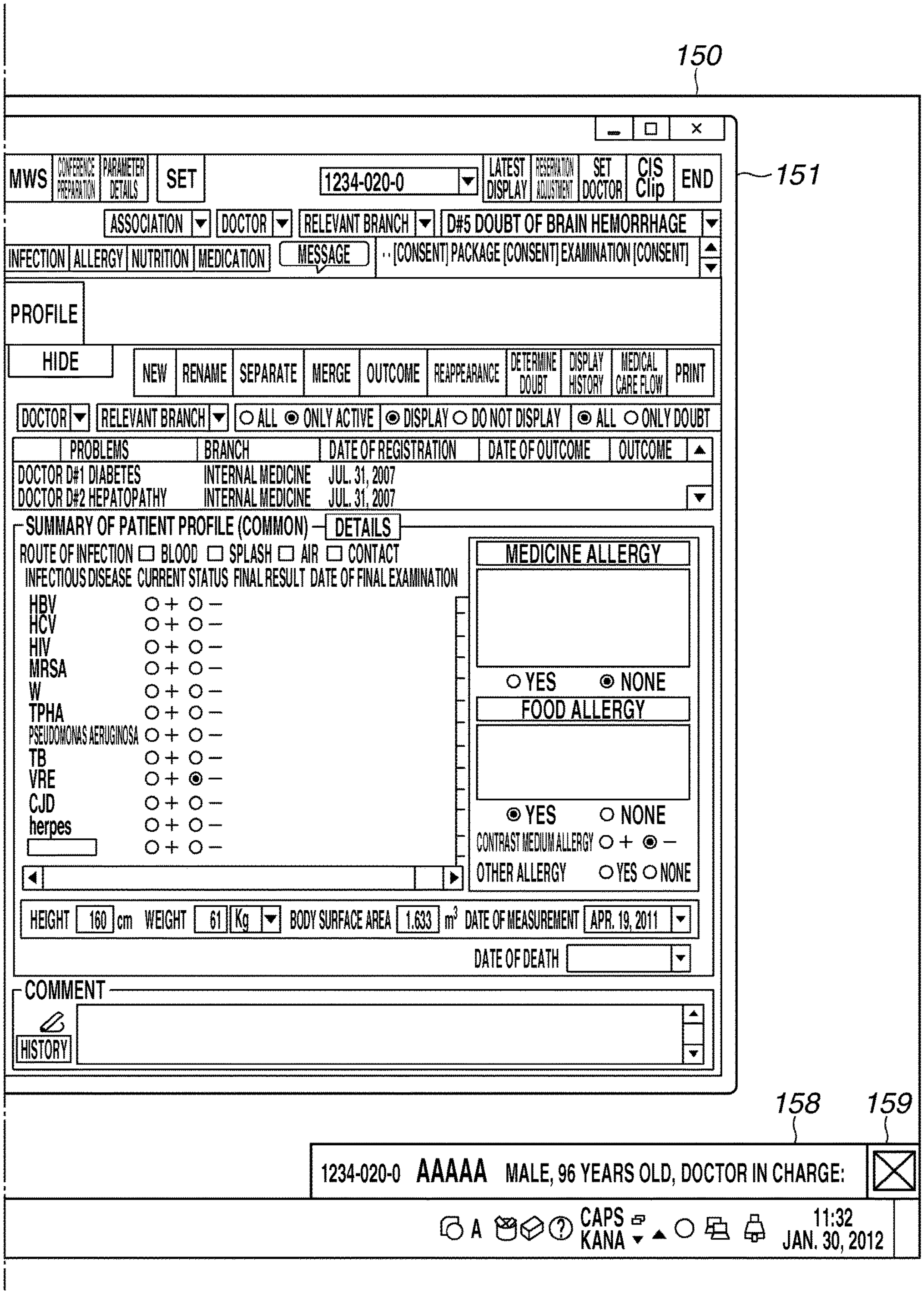

In step S107, the electronic chart system 151 loads a material by acquiring a basic patient information character string 140 displayed on the screen, as illustrated in FIG. 5. The electronic chart system 151, which displays the basic patient information character string 140 through an original drawing process without using the standard GUI components of the operating system (OS), acquires the area of the basic patient information character string 140 as image information, and converts the image information into character code strings through the character recognition process. Further, the electronic chart system 151 acquires the SOAP description from the electronic chart server 6 illustrated in FIG. 1 based on the basic patient information (for example, patient ID) acquired by using the above-described method. In addition, the electronic chart system 151 may acquire the SOAP description by directly issuing to a database of the electronic chart server 6 a structured query language (SQL) by using the basic patient information (for example, patient ID) as a key.

The basic patient information and the SOAP description acquired are stored as the material registration information 20 in the data storage area 207 of the conference server 2 illustrated in FIG. 1. Further, a binder 302 corresponding to the patient name or case name in the loaded basic patient information is generated in the binder pool 301 of the file server 3.

When material loading is completed, in step S108, the electronic chart system 151 exits the material loading mode. In step S109, an indicator 158 displays a result of loading, as illustrated in FIG. 5. At this timing, the loaded material can be canceled by pressing a CANCEL button 159 included in the indicator 158.

Figure 6:
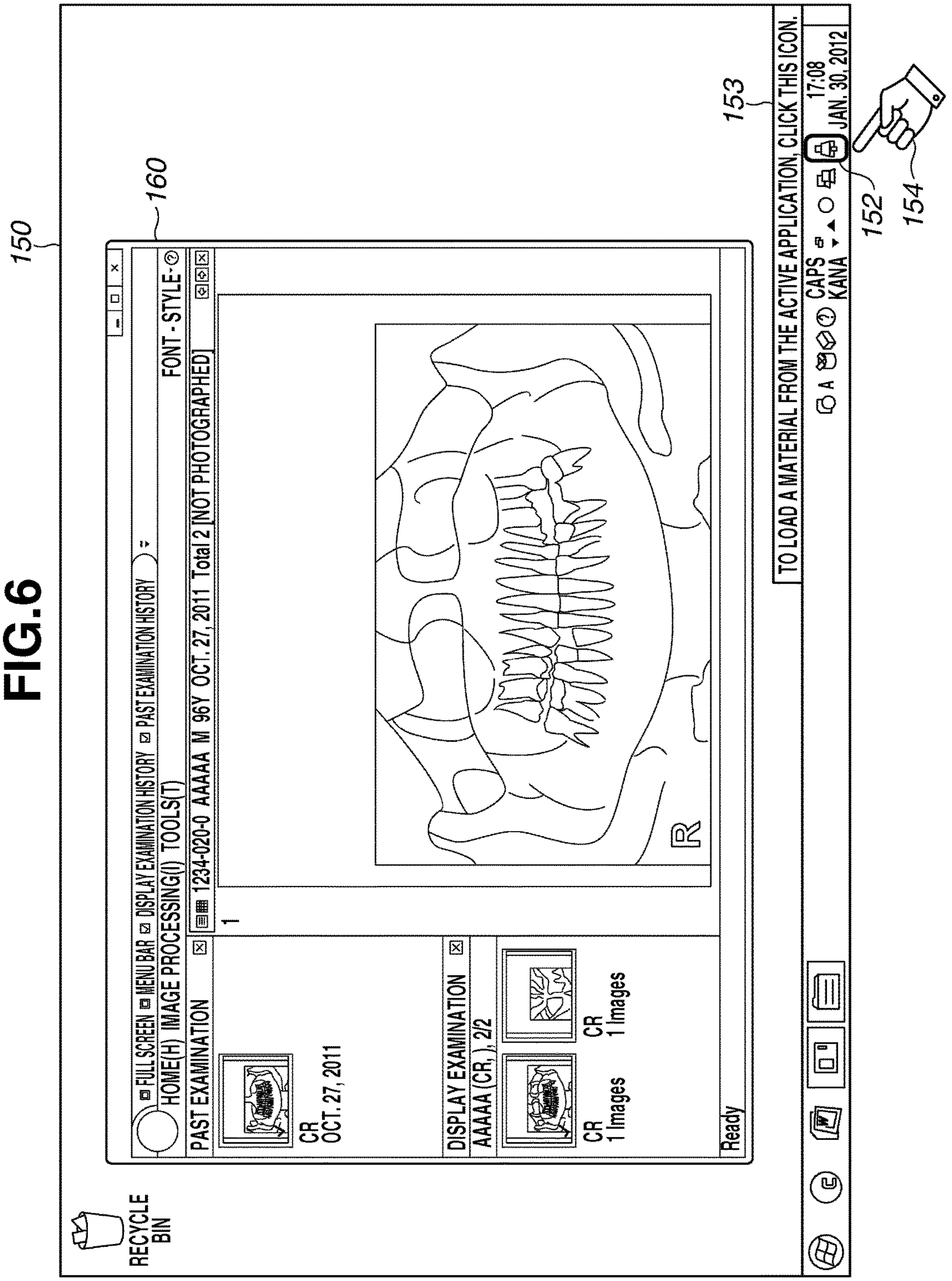
FIG. 6 illustrates an example screen before the material loading mode is activated.

The following describes processing for loading DICOM image information (material information) from a PACS viewer 160 on the desktop screen 150 illustrated in FIG. 6. Similar to the case of the electronic chart, the PACS viewer 160 starts the material loading processing when the doctor in charge clicks the LOAD MATERIAL button 152. Subsequently, the processing proceeds according to the flowchart illustrated in FIG. 28.

Figure 7:
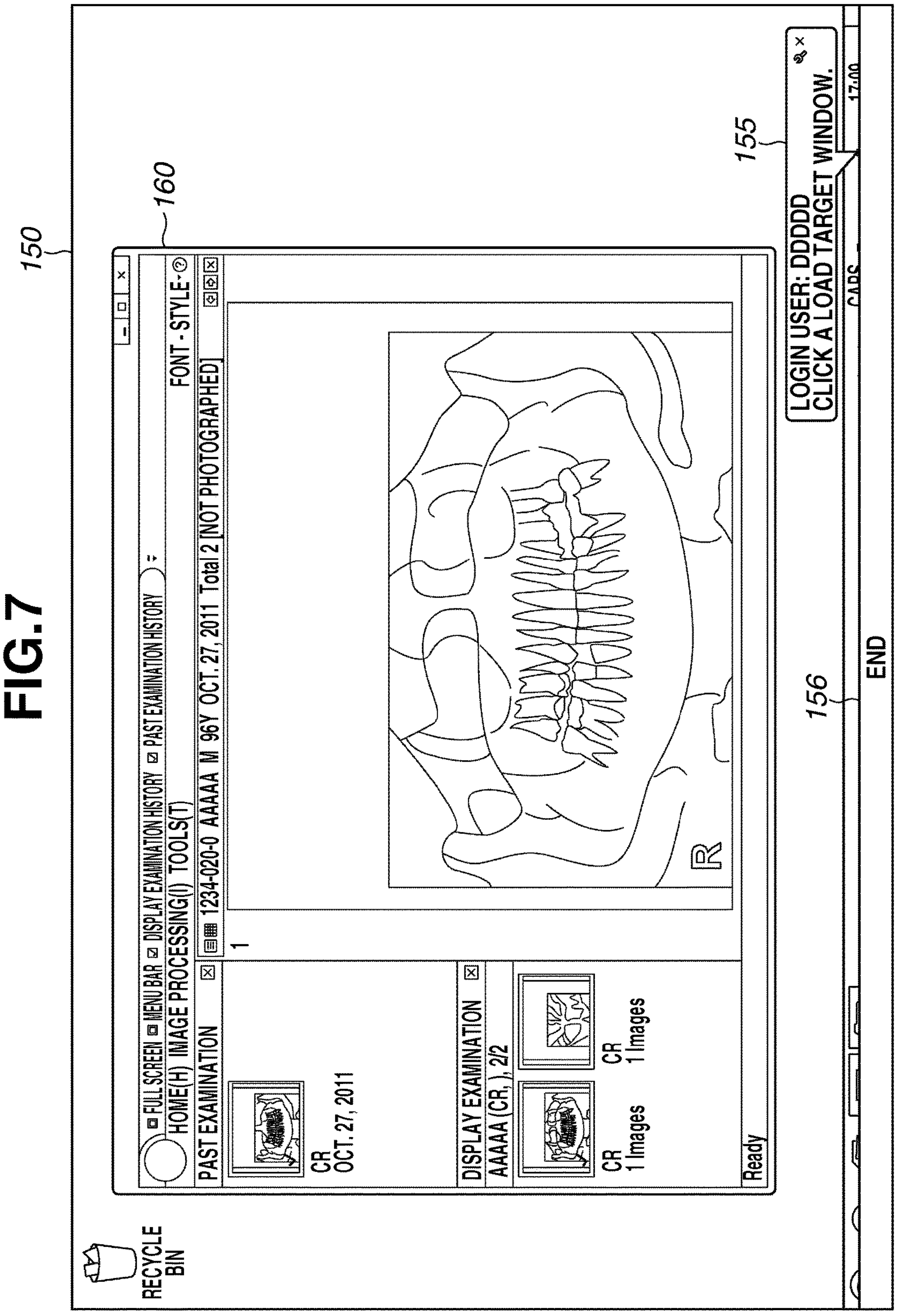
FIG. 7 illustrates an example screen after the material loading mode is activated.

In step S101, when the material loading mode is activated, the desktop screen 150 is covered by a semi-transparent white window, as illustrated in FIG. 7. The pop-up 155 and the END button 156 operate in a similar way to the case of the electronic chart system 151.

Figure 8:
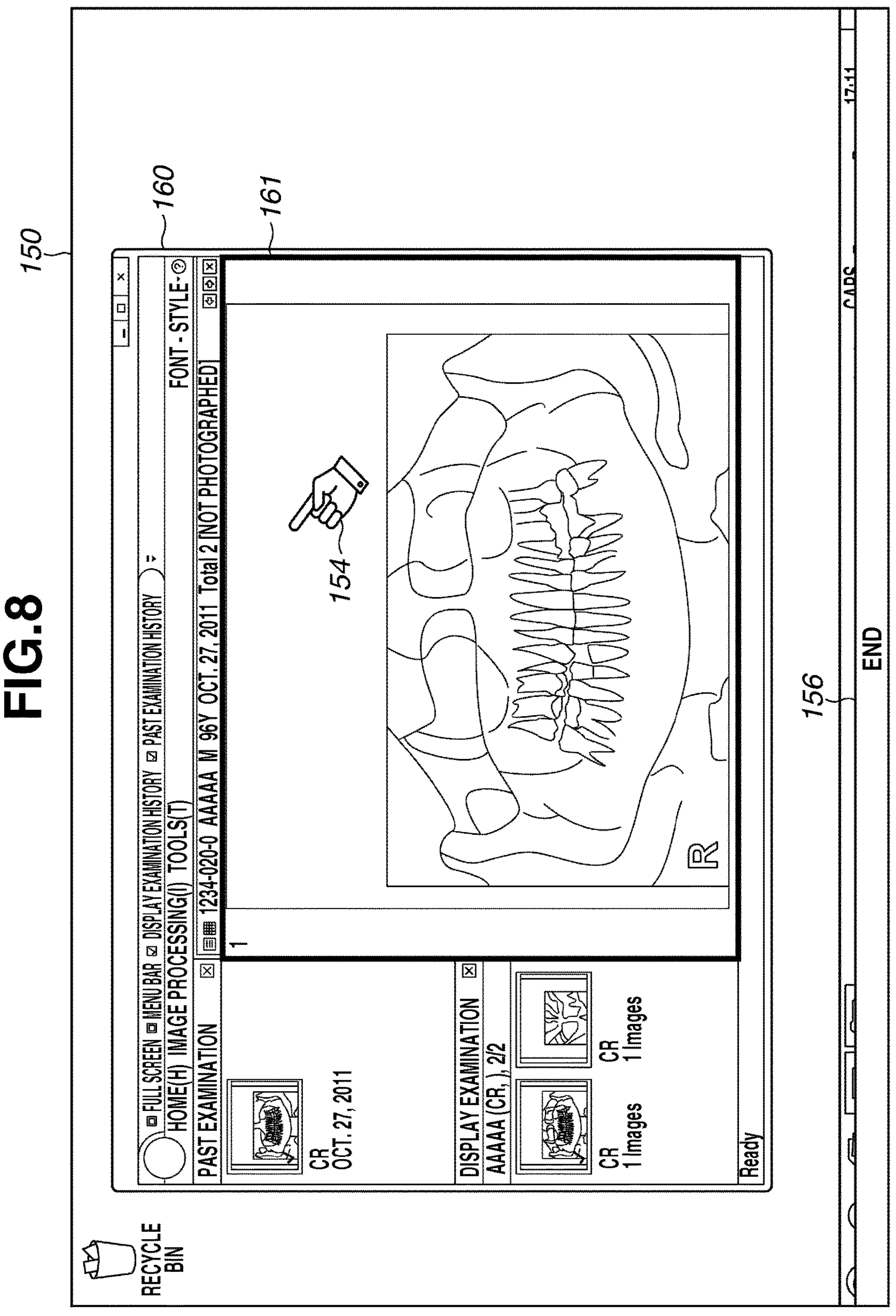
FIG. 8 illustrates an example screen after a load target material is specified.

When the user clicks a target DICOM image screen of the PACS viewer 160 by using the pointing unit 154 in the material loading mode, as illustrated in FIG. 8, a load target material is specified. A load target material may be specified by any method other than clicking. When a load target window is specified, the PACS viewer 160 searches for the process of the window's owner based on the window handle and then determines whether the target application is a loadable application (in this case, the PACS viewer 160) based on the process name. When the target application is determined to be a loadable application (YES in step S103), then in step S104, the PACS viewer 160 encloses a load target area 161 with a red square frame. With the PACS viewer 160, a load target area can be specified for each DICOM image and, even when a plurality of DICOM images is displayed on the PACS viewer 160, each individual image to be acquired can be specified.

The method for specifying a load target area is not limited to enclosing it with a red square frame. Then, when the user double-clicks or right-clicks the load target area 161 by using the pointing unit 154 to instruct executing loading (YES in step S106), then in step S107, the PACS viewer 160 loads the material. The instruction for loading execution is not limited to double-clicking and right-clicking.

Figure 9:
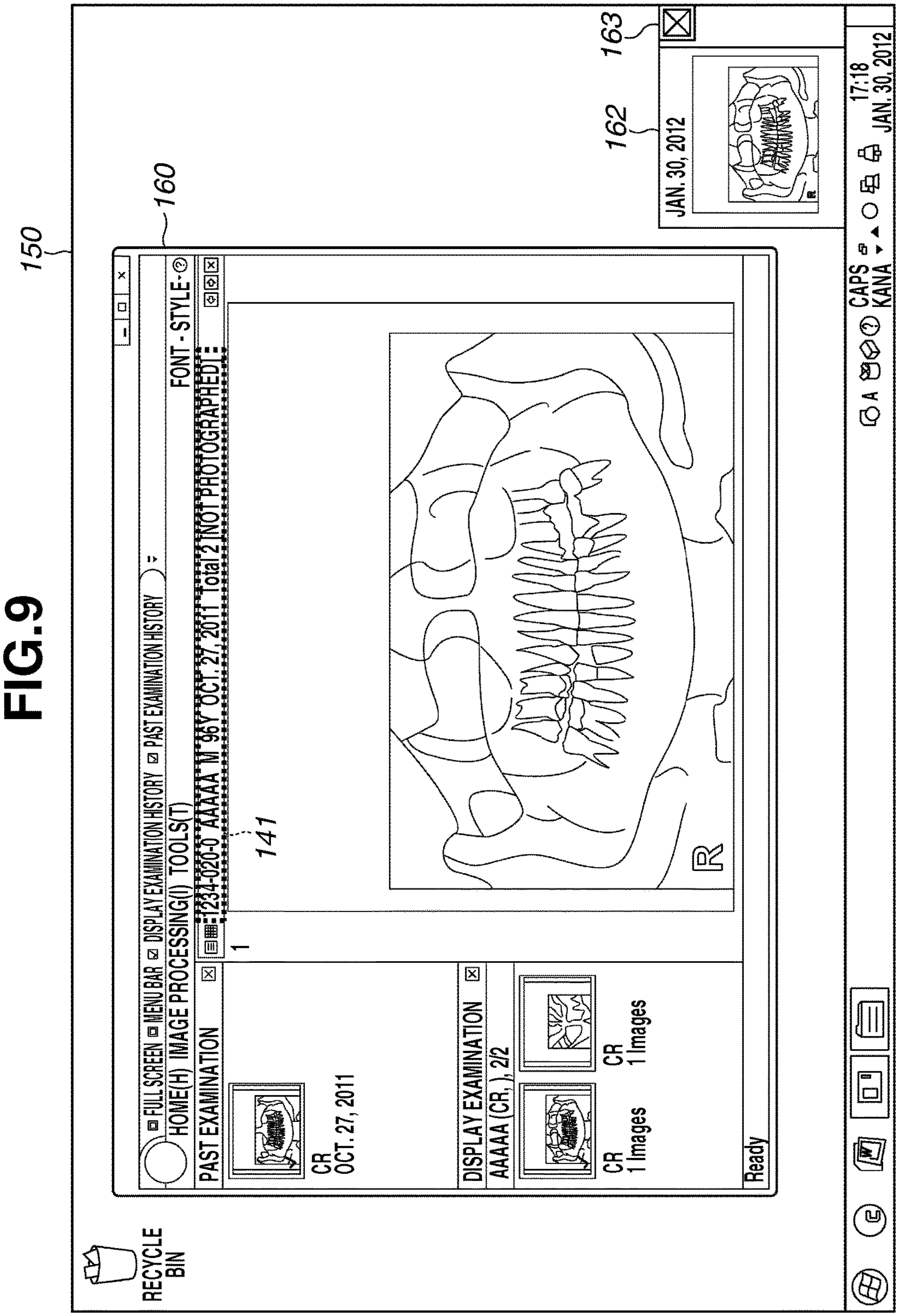
FIG. 9 illustrates an example screen displaying a result of loading the load target material.
Figure 10A:
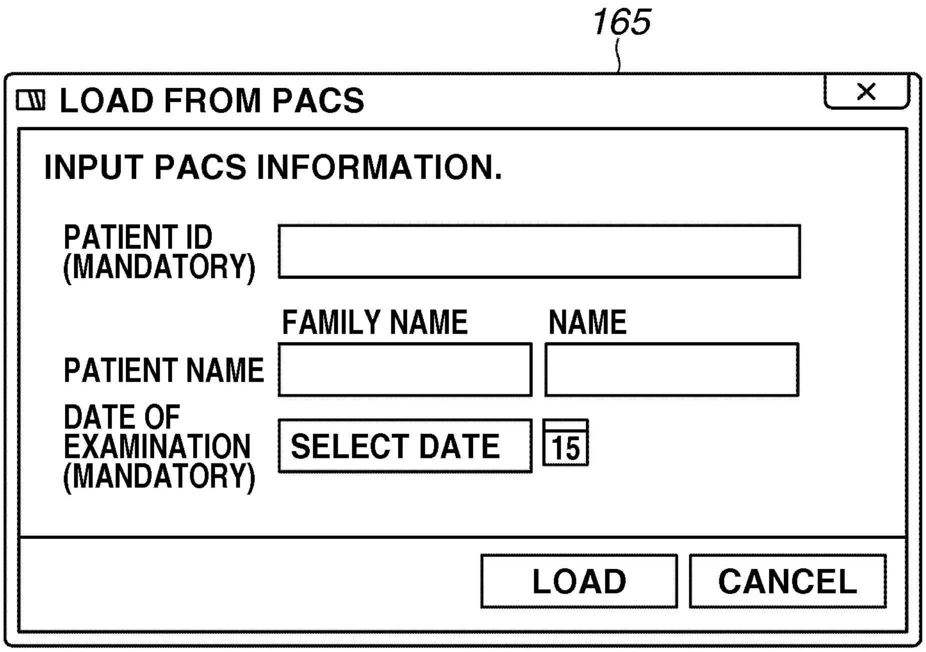
FIGS. 10A and 10B illustrate example dialog screens for manually inputting patient information.
Figure 10B:
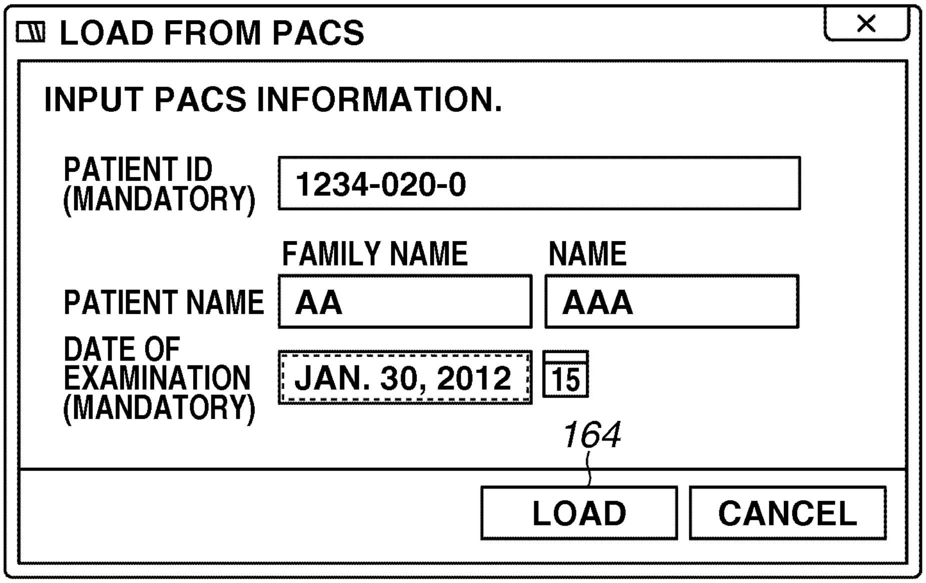

In step S107, the PACS viewer 160 loads a material by performing screen capturing for the load target area 161 and then acquiring an image identification character string 141 displayed on the screen, as illustrated in FIG. 9. The PACS viewer 160, which displays the image identification character string 141 through original drawing without using the standard GUI components of the operating system (OS), acquires the area of the image identification character string 141 as image information, and converts the image information into character code strings through the character recognition process. the PACS viewer 160 acquires the DICOM image information from the PACS server 4 illustrated in FIG. 1 by using the DICOM protocol based on the image identification information (for example, the patient ID and the date of examination) acquired by the above-described method. In addition, the PACS viewer 160 may acquire the DICOM image information by displaying an input dialog as illustrated in FIGS. 10A and 10B on the desktop screen 150, and then having the doctor in charge manually input insufficient information.

The acquired DICOM image information is stored as the material registration information 20 in the data storage area 207 of the conference server 2 illustrated in FIG. 1. The acquired screen capture image is stored as the presentation image 30 in the binder 302 of the binder pool 301 of the file server 3 corresponding to the patient name or case name in the loaded DICOM image information, Further, a reduced version of the relevant image is stored as the thumbnail 31.

When material loading is completed, in step S108, the PACS viewer 160 exits the material loading mode. In step S109, an indicator 162 displays a result of loading, as illustrated in FIG. 9. At this timing, the loaded material can be canceled by pressing a CANCEL button 163 included in the indicator 162.

Figure 11:
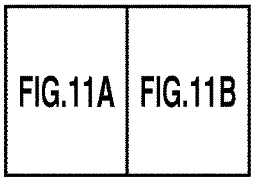
FIG. 11, which is composed of FIGS. 11A and 11B, illustrates an example screen before the material loading mode is activated.
Figure 11A:
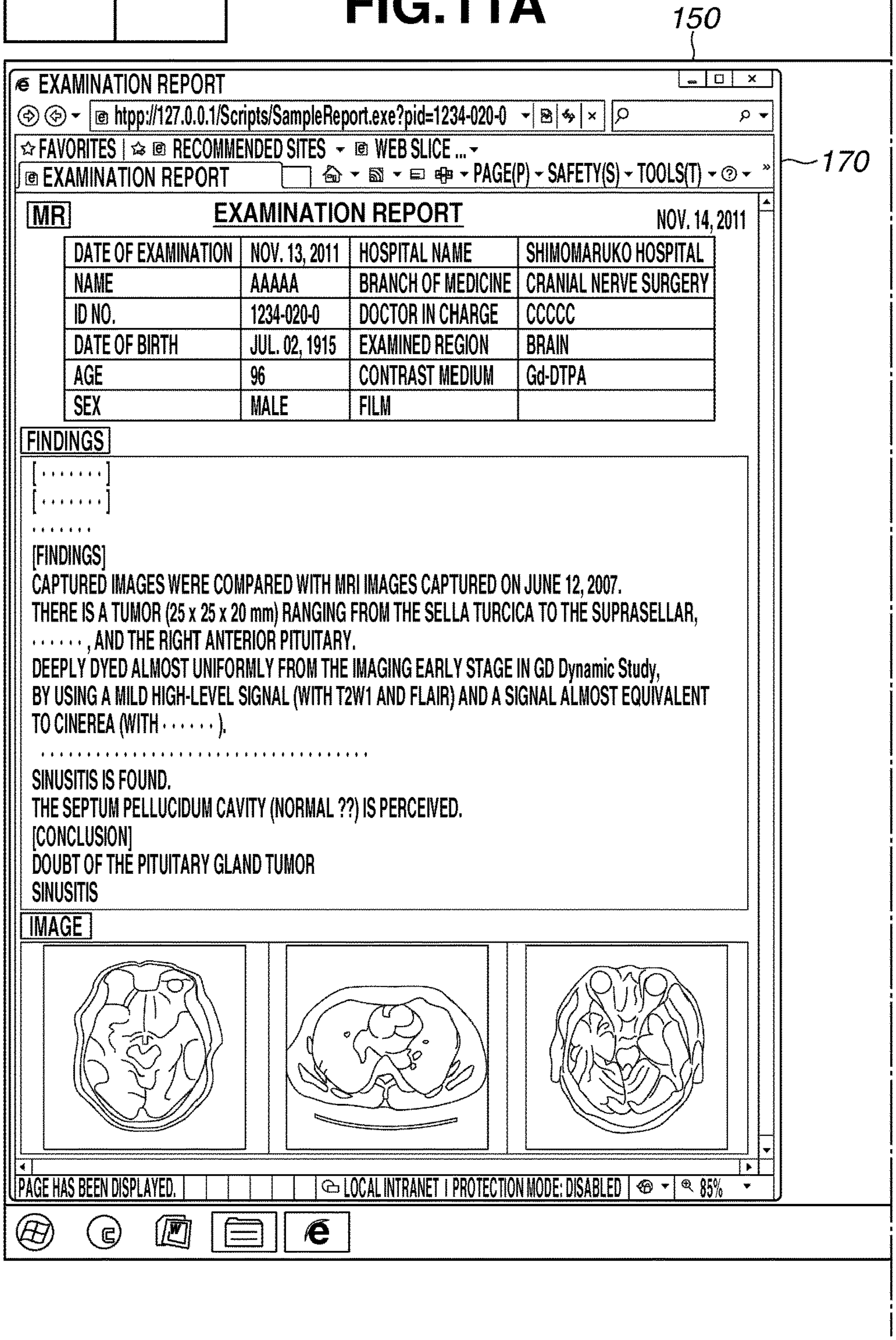
Figure 11B:
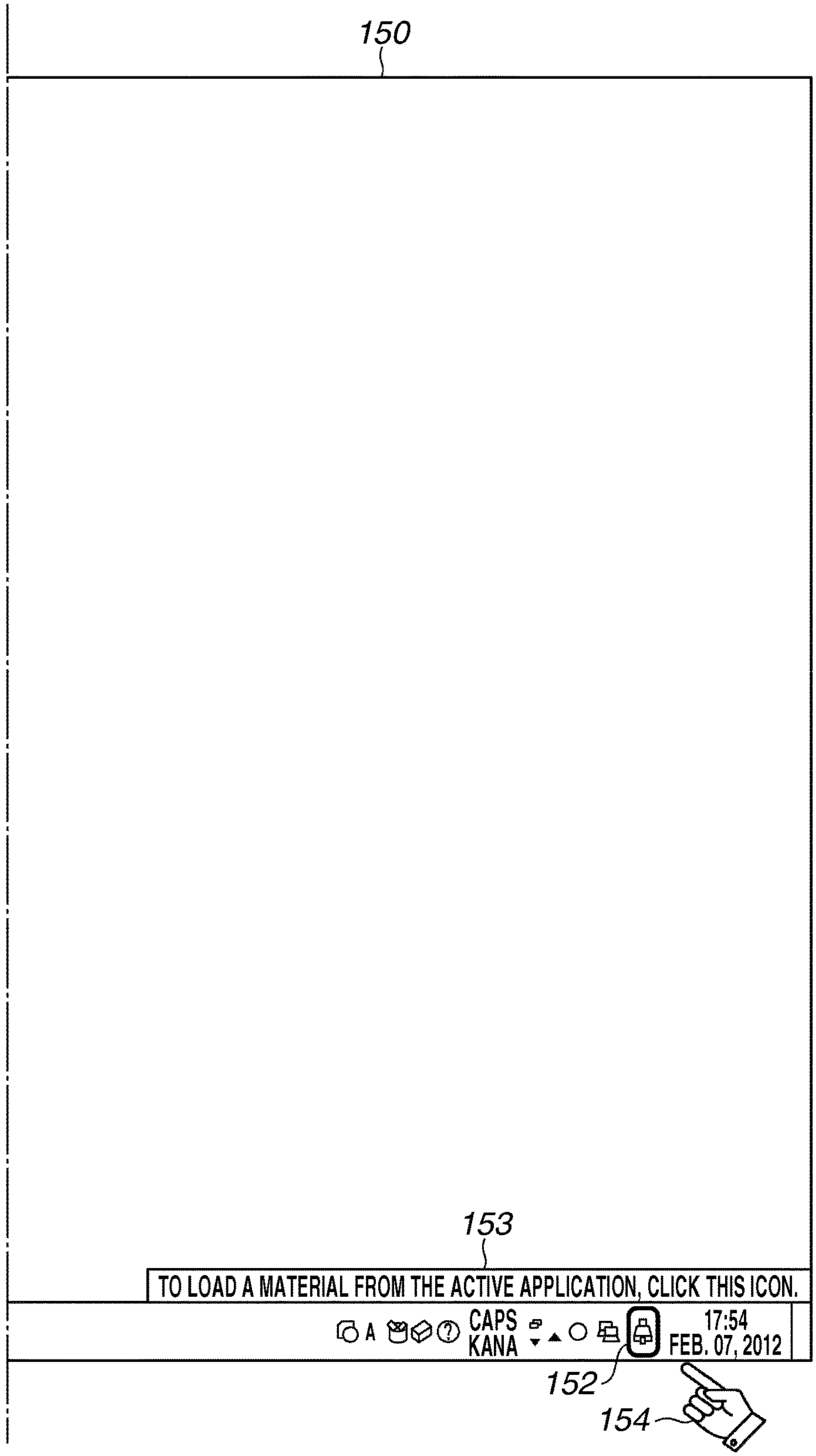

The following describes processing for loading examination report information from the diagnostic reporting system 170 on the desktop screen 150 illustrated in FIG. 11. Similar to the case of the electronic chart system 151, when the doctor in charge clicks the LOAD MATERIAL button 152, the diagnostic reporting system 170 starts the material loading processing. Subsequently, the processing proceeds according to the flowchart illustrated in FIG. 28.

Figure 12:
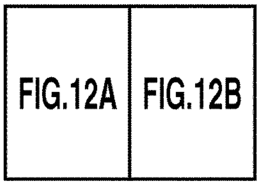
FIG. 12, which is composed of FIGS. 12A and 12B, illustrates an example screen after the material loading mode is activated.
Figure 12A:
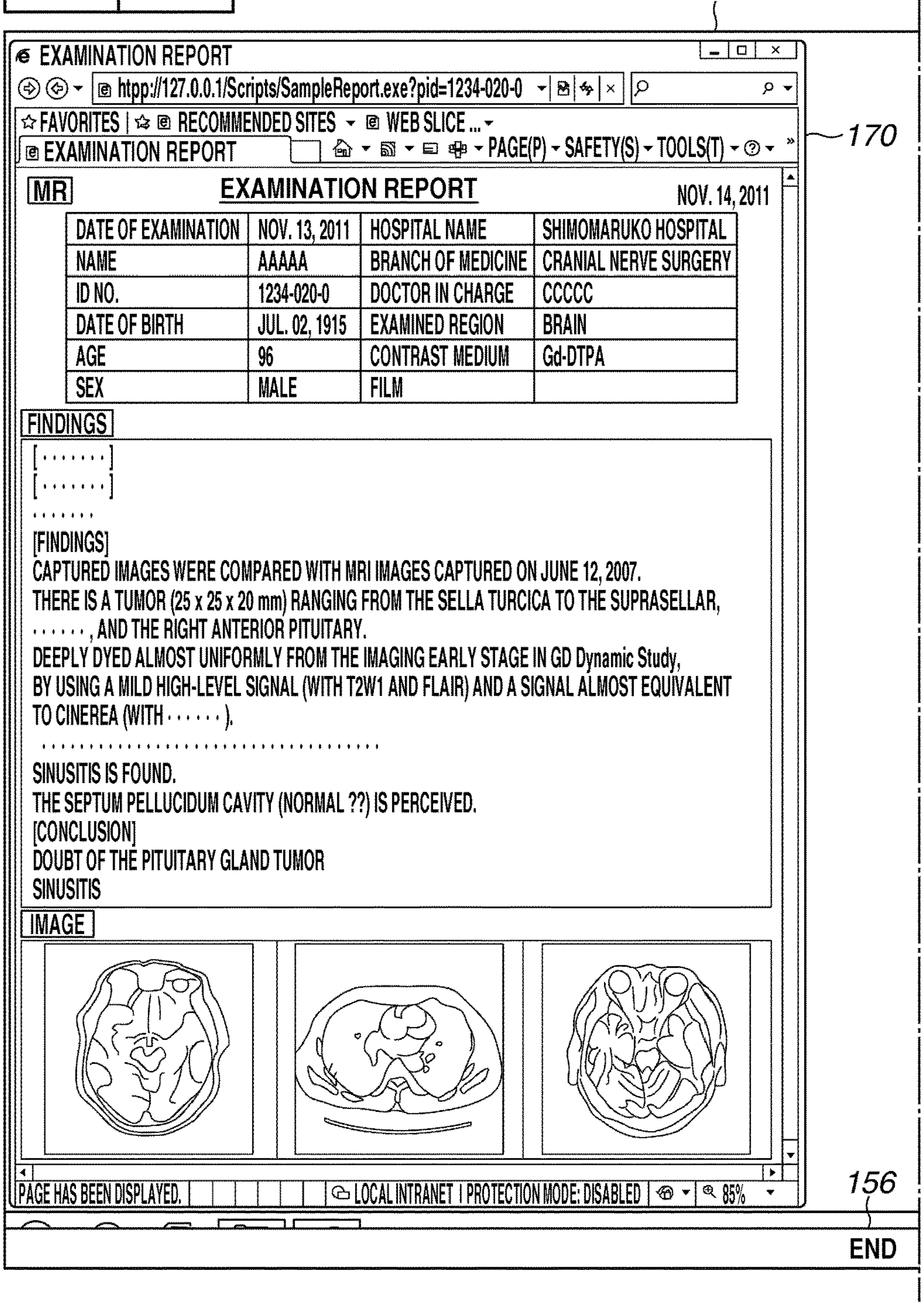
Figure 12B:
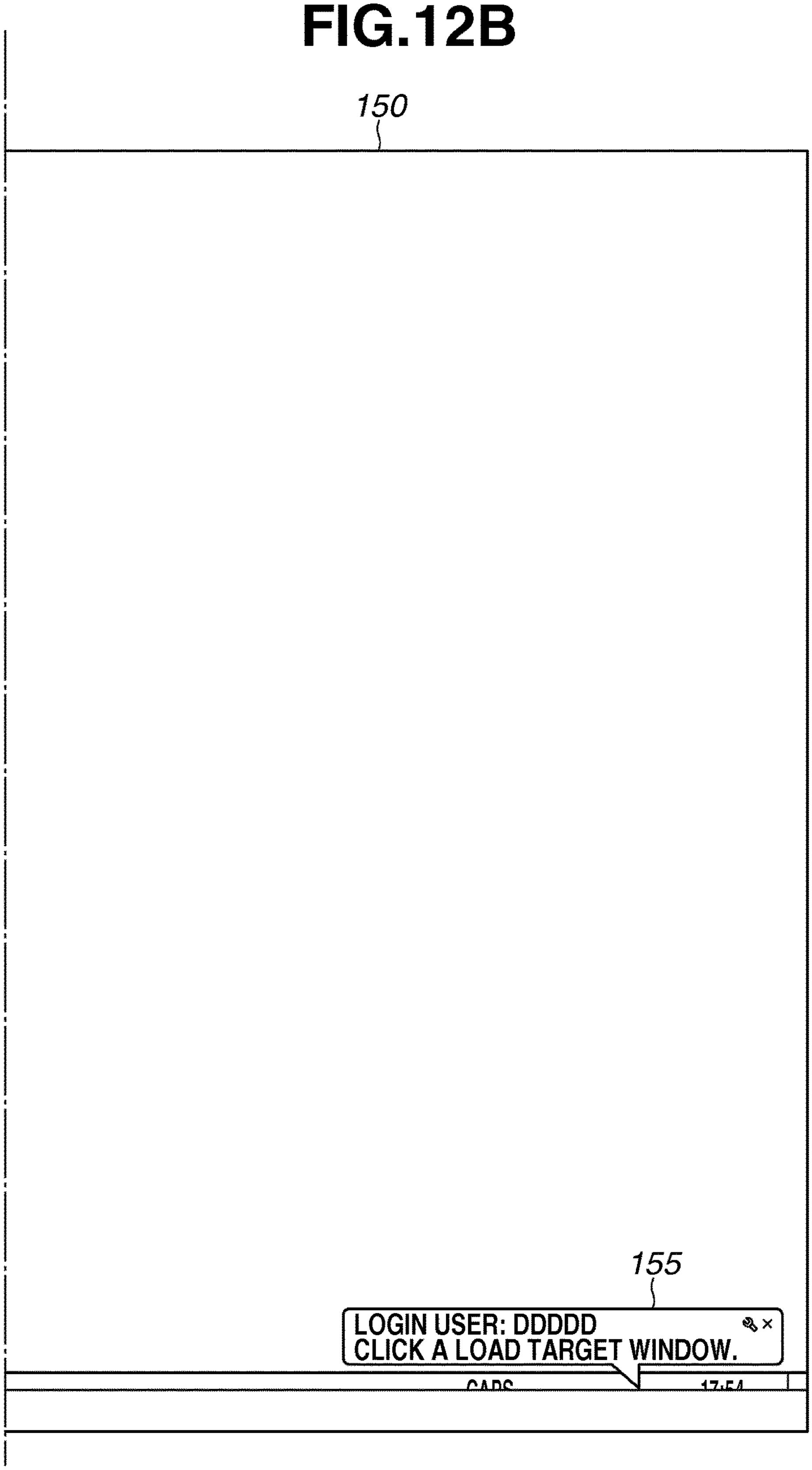

In step S101, when the material loading mode is activated, the desktop screen 150 is covered by a semi-transparent white window, as illustrated in FIG. 12. The pop-up 155 and the END button 156 operate in a similar way to the case of the electronic chart.

Figure 13:
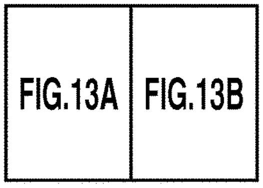
FIG. 13, which is composed of FIGS. 13A and 13B, illustrates an example screen after a load target material is specified.
Figure 13A:
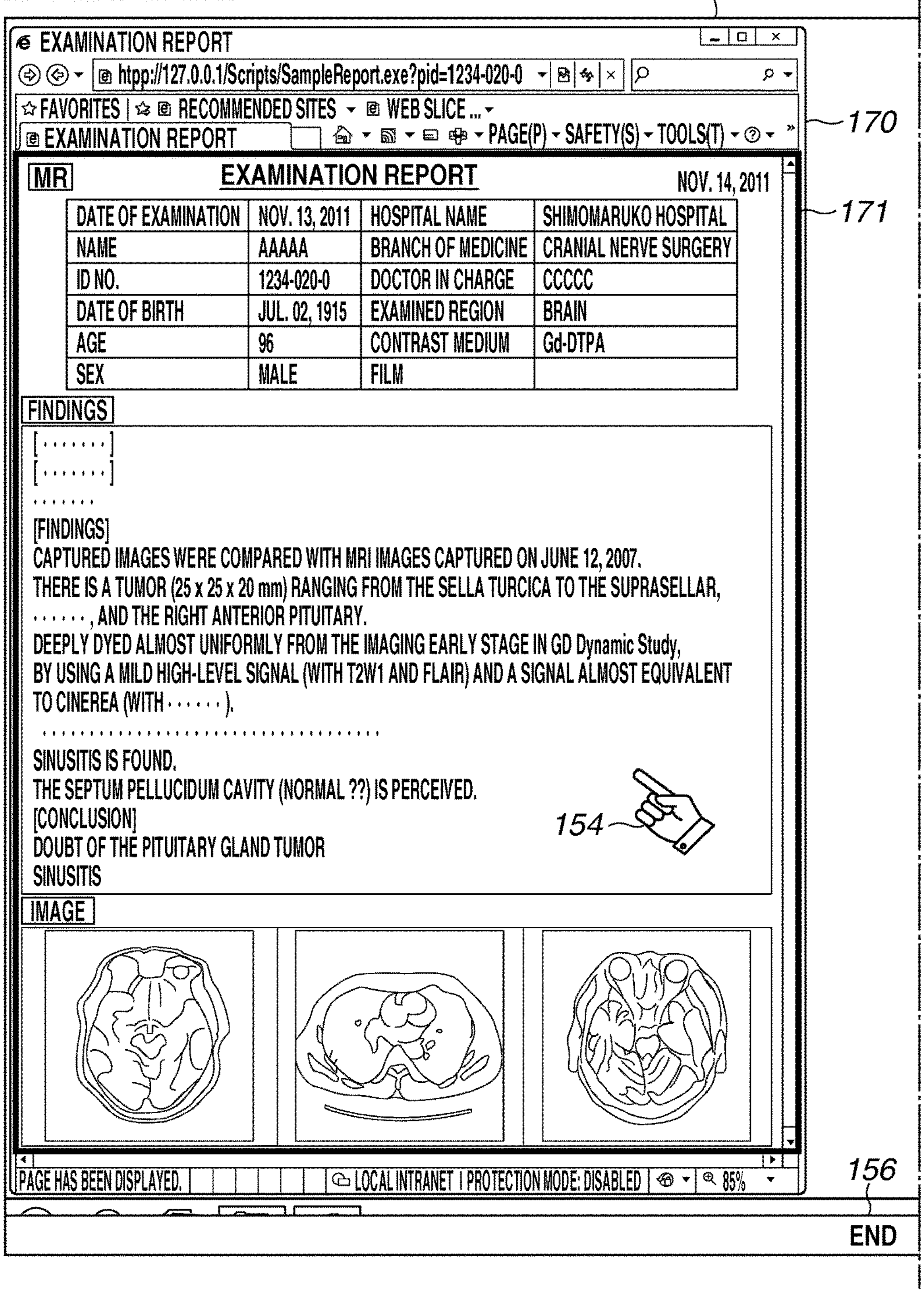
Figure 13B:
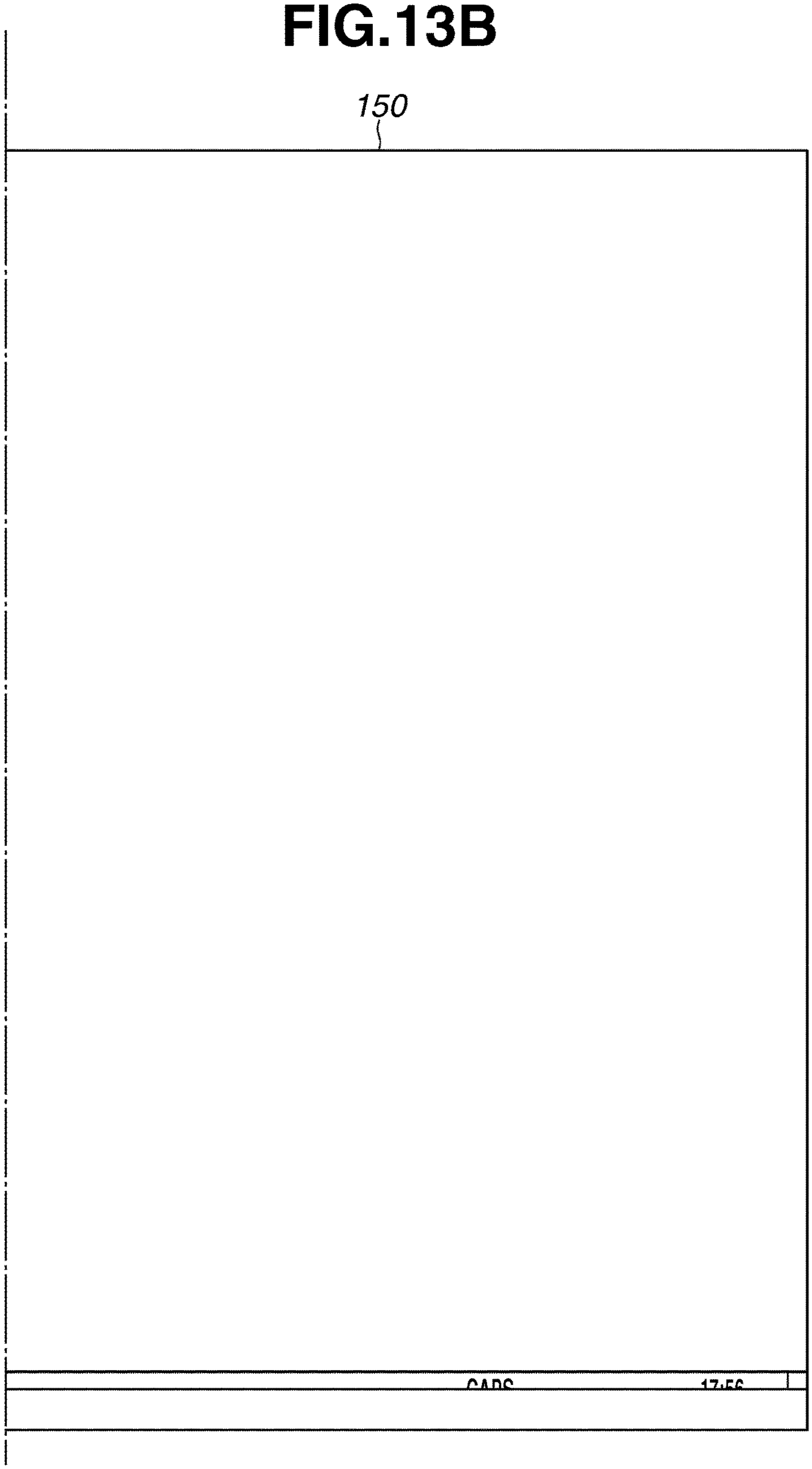

Then, when the user clicks the screen of the diagnostic reporting system 170 by using the pointing unit 154 in the material loading mode, as illustrated in FIG. 13, a load target material is specified. A load target material may be specified by any method other than clicking. When a load target window is specified, the diagnostic reporting system 170 searches for the process of the window's owner based on the window handle and then determines whether the target application is a loadable application (in this case, the diagnostic reporting system 170) based on the process name. When the target application is determined to be a loadable application (YES in step S103), then in step S104, the diagnostic reporting system 170 encloses a load target area 171 with a red square frame. The method for specifying a load target area is not limited to enclosing it with a red square frame. Then, when the user double-clicks or right-clicks the load target area 171 by using the pointing unit 154 to instruct executing loading (YES in step S106), then in step S107, the diagnostic reporting system 170 loads the material. The instruction for loading execution is not limited to double-clicking and right-clicking.

Figure 14:
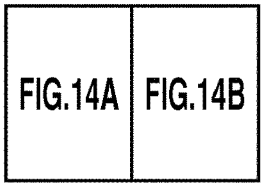
FIG. 14, which is composed of FIGS. 14A and 14B, illustrates an example screen displaying a result of loading the load target material.
Figure 14A:
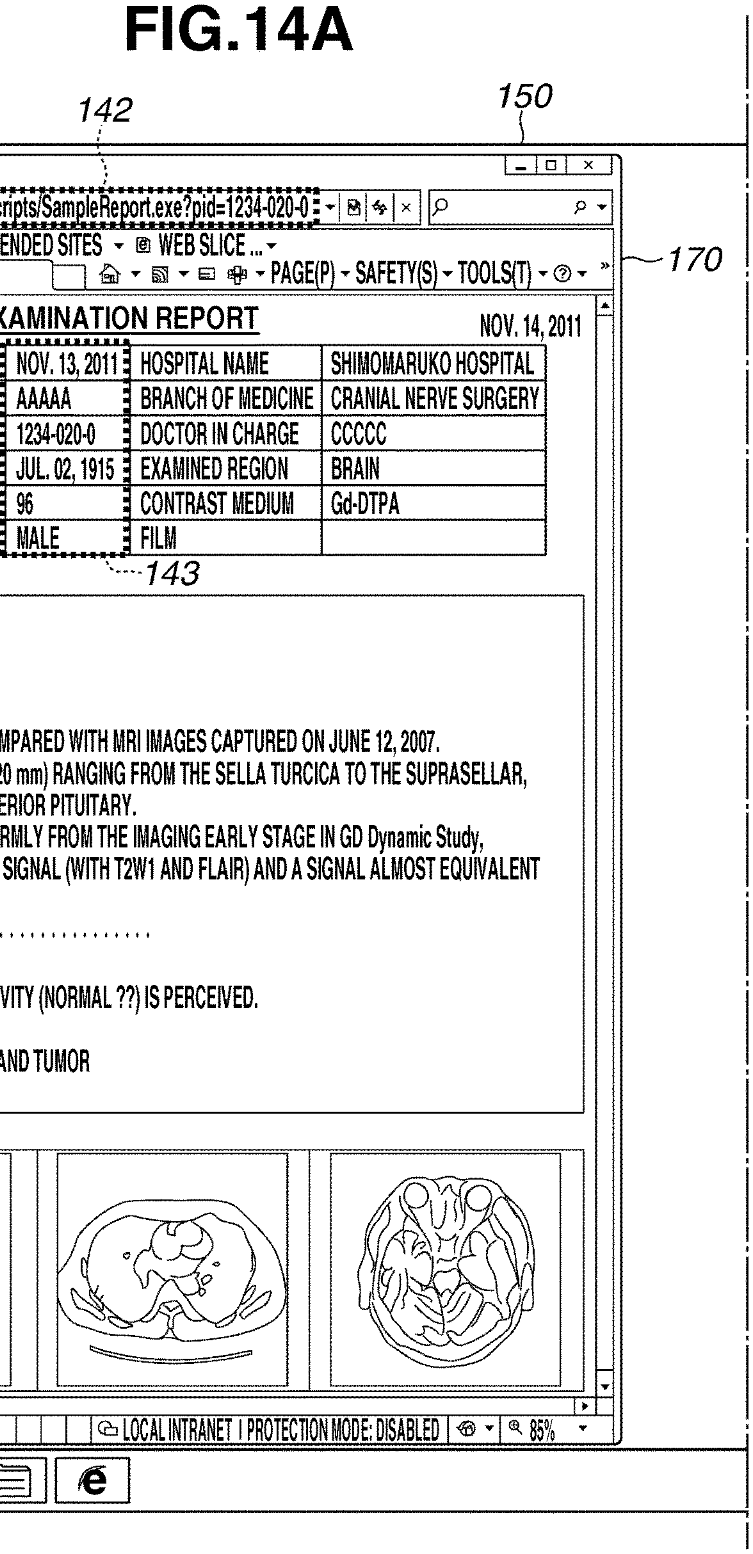
Figure 14B:
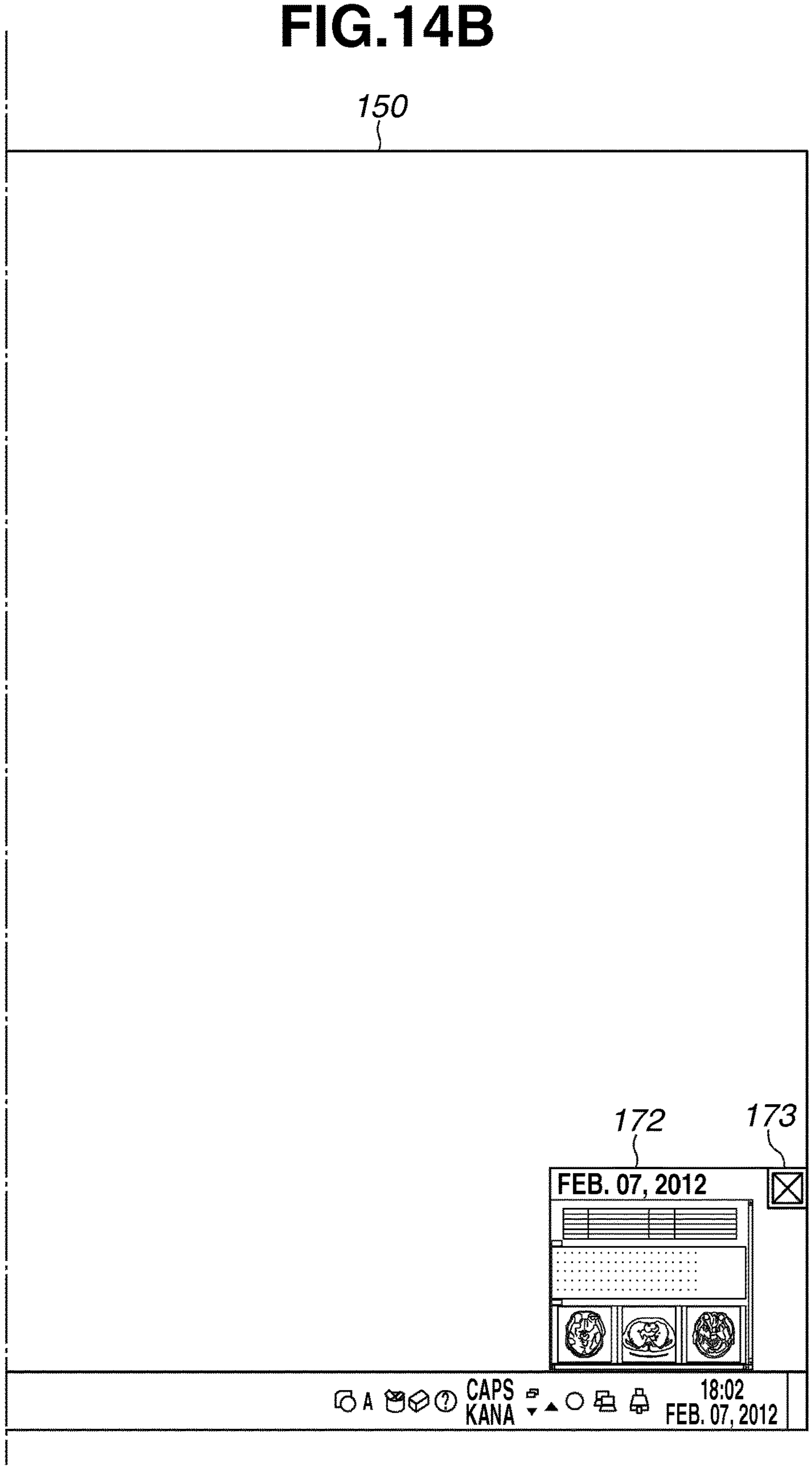

In step S107, the diagnostic reporting system 170 loads a material by performing screen capturing for the load target area 171 and then acquiring an examination identification character string 143 displayed on the screen, as illustrated in FIG. 14. The diagnostic reporting system 170, which displays the examination identification character string 143 through original drawing without using the standard GUI components of the operating system (OS), acquires the area of the examination identification character string 143 as image information, and converts the image information into character code strings through the character recognition process. In addition, the diagnostic reporting system 170 may acquire a URL character string displayed on an address bar 142 illustrated in FIG. 14 and then acquire examination identification information contained in the URL character string. The diagnostic reporting system 170 acquires examination report information from the diagnostic report server 5 illustrated in FIG. 1 by using the HTTP protocol based on the examination identification information (for example, the patient ID and the date and time of examination) acquired by the above-described method.

The acquired examination report information is stored as the material registration information 20 in the data storage area 207 of the conference server 2 illustrated in FIG. 1. The acquired screen capture image is stored as the presentation image 30 in the binder 302 of the binder pool 301 of the file server 3 corresponding to the patient name or case name in the loaded examination report information. Further, a reduced version of the relevant image is stored as the thumbnail 31. Thus, materials are managed on a person-by-person basis.

When material loading is completed, in step S108, the diagnostic reporting system 170 exits the material loading mode. In step S109, an indicator 172 displays a result of loading, as illustrated in FIG. 14. At this timing, the loaded material can be canceled by pressing a CANCEL button 173 included in the indicator 172.

Figure 15:
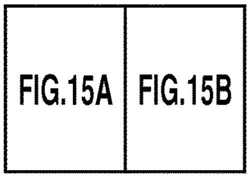
FIG. 15, which is composed of FIGS. 15A and 15B, illustrates an example screen for opening a loaded material confirmation screen.
Figure 15A:
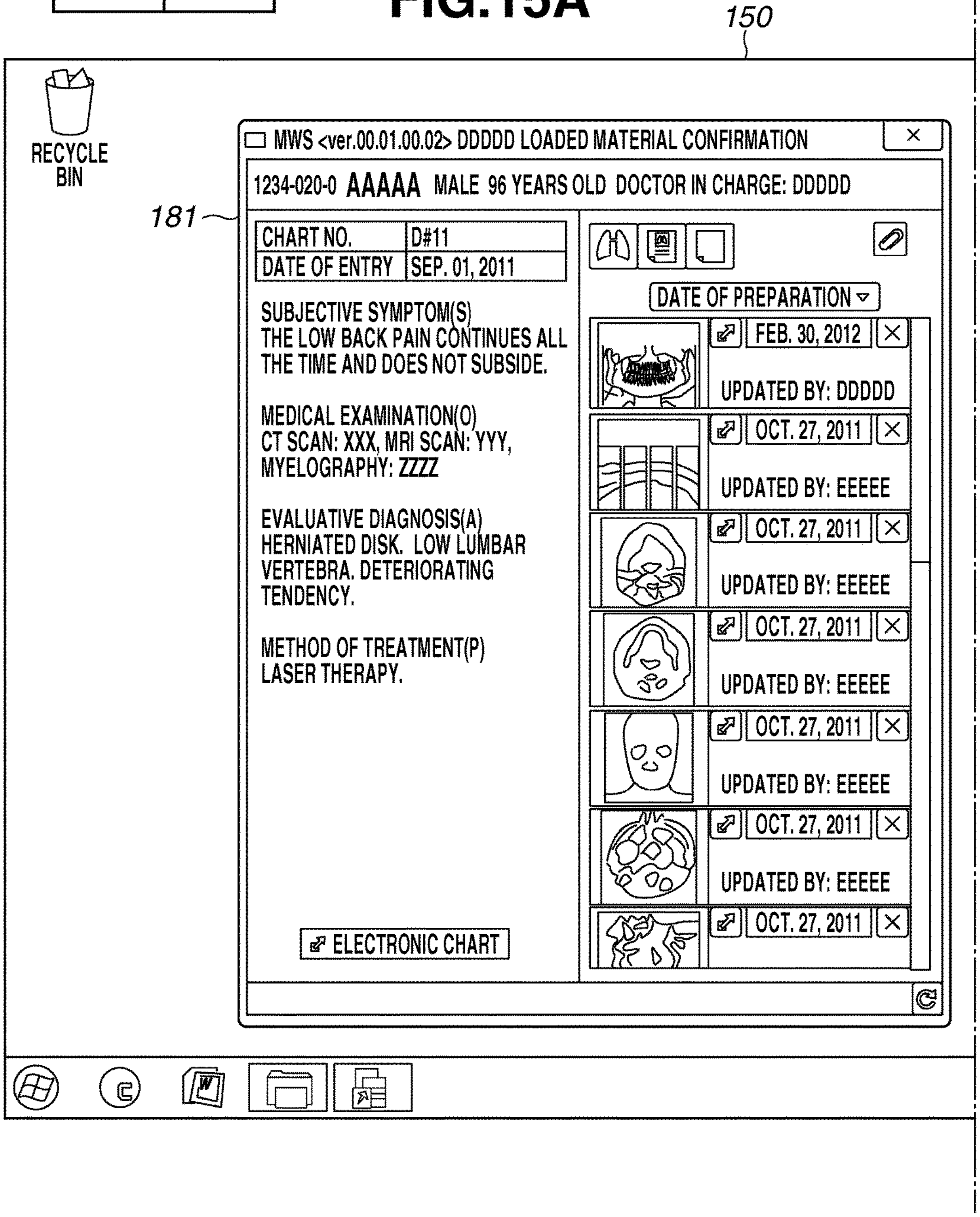
Figure 15B:
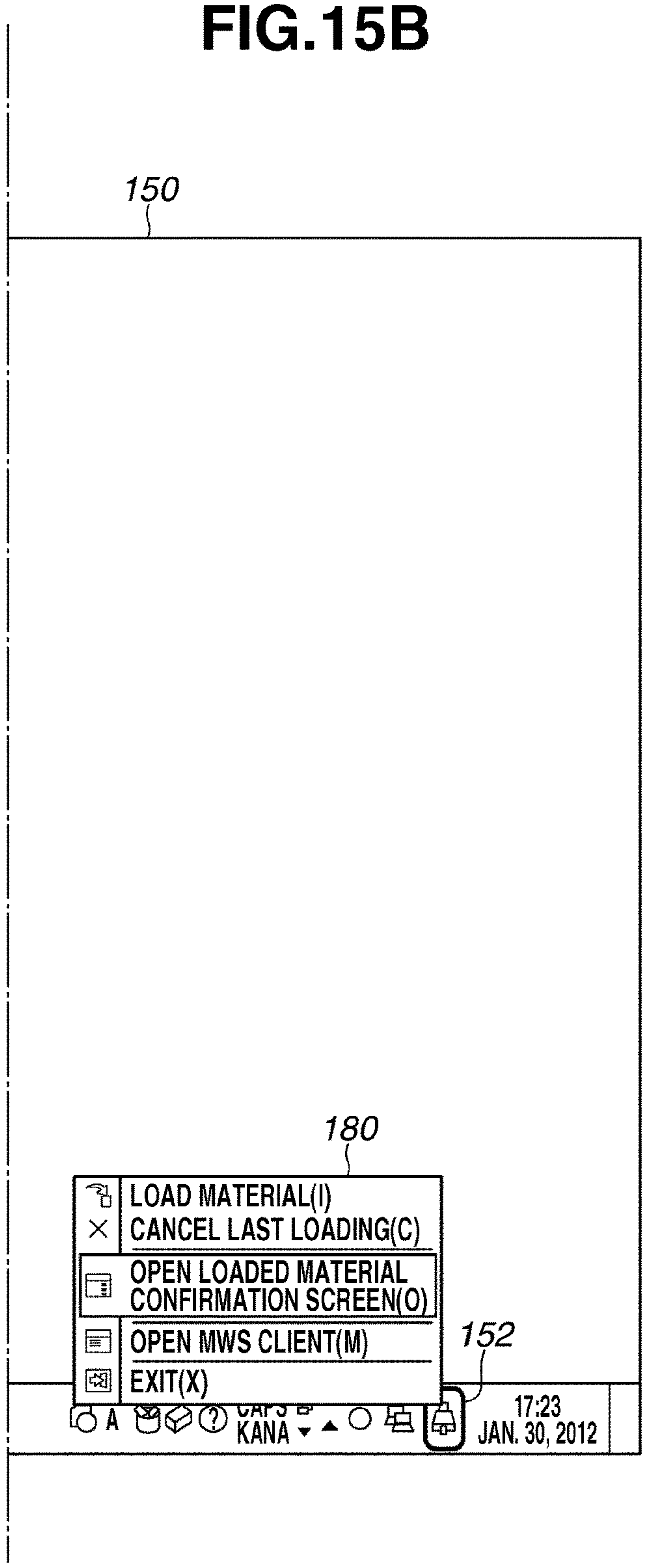

When the user right-clicks or long-presses the LOAD MATERIAL button 152, as illustrated in FIG. 15, a conference preparation menu 180 appears allowing the user to open a loaded material confirmation screen 181.

Figure 16:
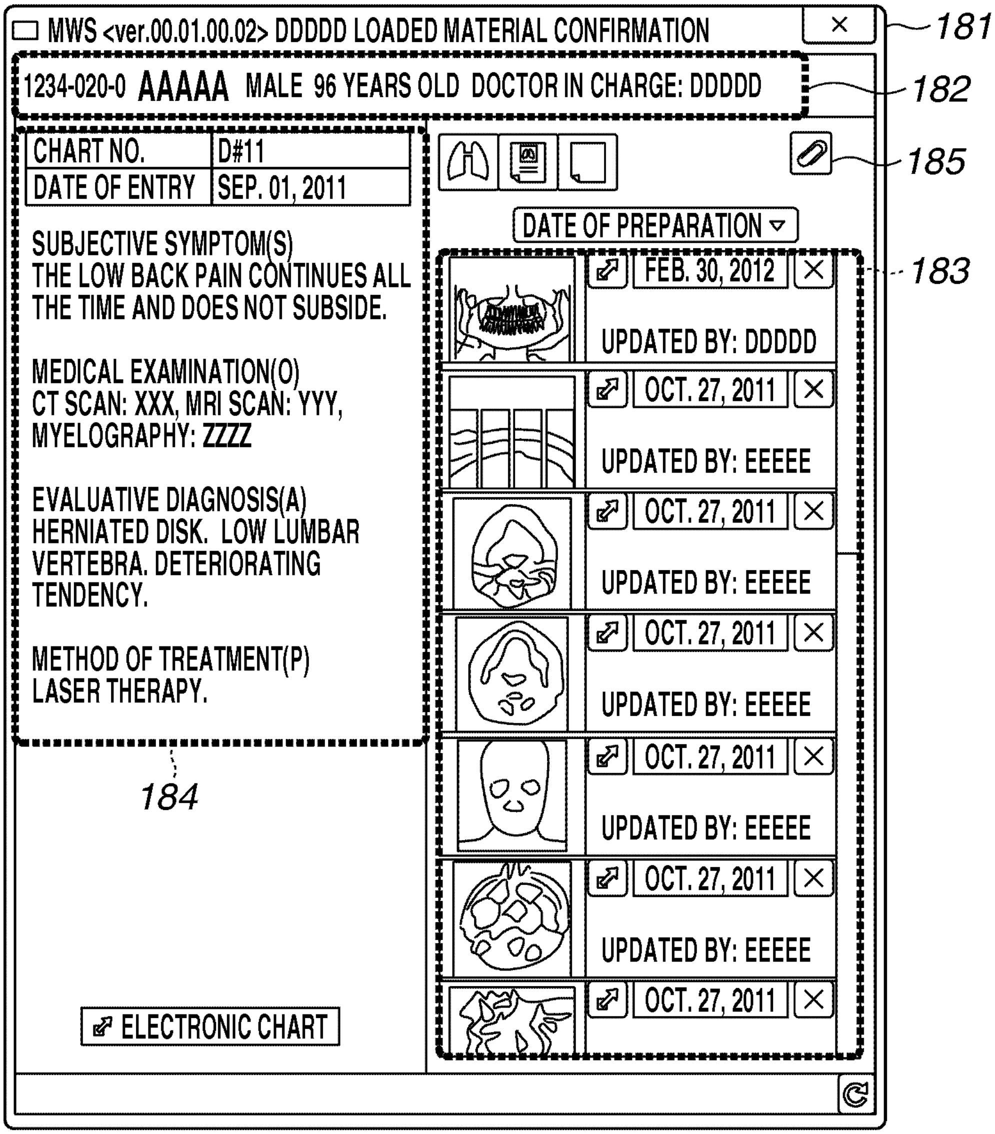
FIG. 16 illustrates an example of the loaded material confirmation screen.

As illustrated in FIG. 16, the loaded basic patient information 182 is displayed at the top of the loaded material confirmation screen 181, the loaded SOAP description 184 is displayed on the left pane, and a loaded DICOM image information list 183 is displayed on the right pane.

When the user presses an ATTACHMENT button 185 illustrated in FIG. 16, a file selection dialog appears. This dialog enables loading a general document file (conference material 10), such as a general image (images other than DICOM) and a portable document format (PDF) file, stored in the image management server 8 illustrated in FIG. 1. An image or a document file can also be loaded by dragging it and dropping it into the loaded material confirmation screen 181.

The following describes processing for reserving a conference and appending an agenda in the conference preparation system with reference to the system configuration illustrated in FIG. 1 and example screens illustrated in FIGS. 17 to 27. The following describes an example use case where a conference organizer prepares a preoperative conference by operating the UI device 101 through a screen displayed on the UI display 105 of the conference client apparatus 1 illustrated in FIG. 1. Although the conference organizer is a doctor in the following descriptions, a hospital staff, such as a medical clerk, may serve as a conference organizer.

For a regular conference, conference reservation is automatically performed and, therefore, an operation for reserving the regular conference is required only once (only the first time). Further, it is possible to search for the latest operation order from the ordering system 7 illustrated in FIG. 1, and to automatically append an operation target patient as an agenda for each conference.

Figure 17:
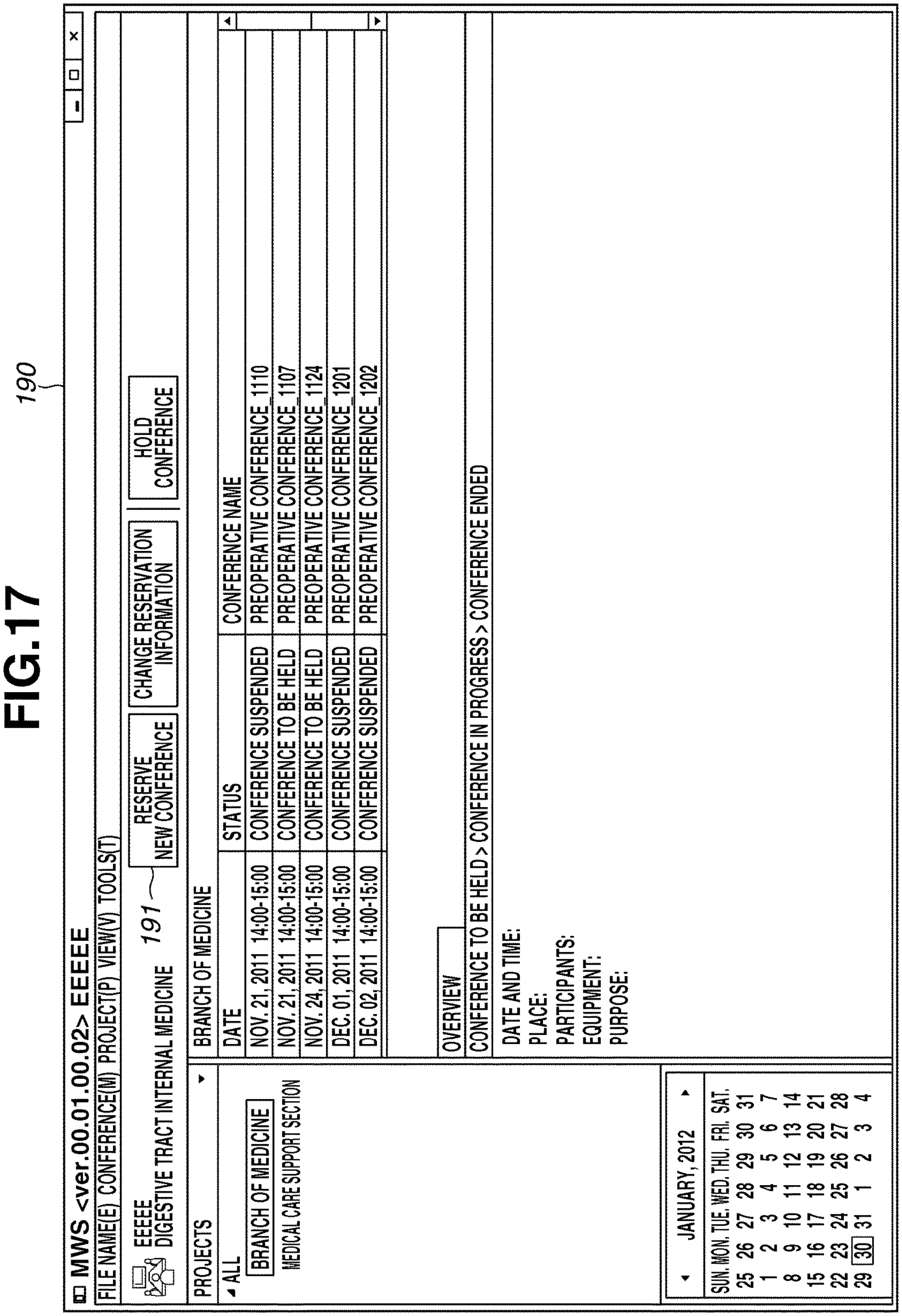
FIG. 17 illustrates an example of a conference list screen.

First, the user opens a conference list screen 190 as illustrated in FIG. 17 by operating the UI device 101 illustrated in FIG. 1. Then, the user presses a RESERVE NEW CONFERENCE button 191 to open the conference reservation screen 189 as illustrated in FIG. 18, and then inputs a conference title in the conference title input area 192. Then, the user presses a NEXT button 193 to change the conference reservation screen 189, as illustrated in FIG. 19, and then specifies participants, conference room, and equipment in an input area 194 and specifies date and time in an input area 195. Then, the user presses a NEXT button 196 to change the conference reservation screen 189, as illustrated in FIG. 20, and then specifies the purpose of the conference in an input area 197. Then, the user presses a NEXT button 198 to change the conference reservation screen 189, as illustrated in FIG. 21, allowing the user to finally confirm the details of the reservation. When the user presses an ISSUE HOLDING NOTIFICATION button 199, conference reservation is completed and a holding notification is issued to the participants by e-mail.

Figure 22:
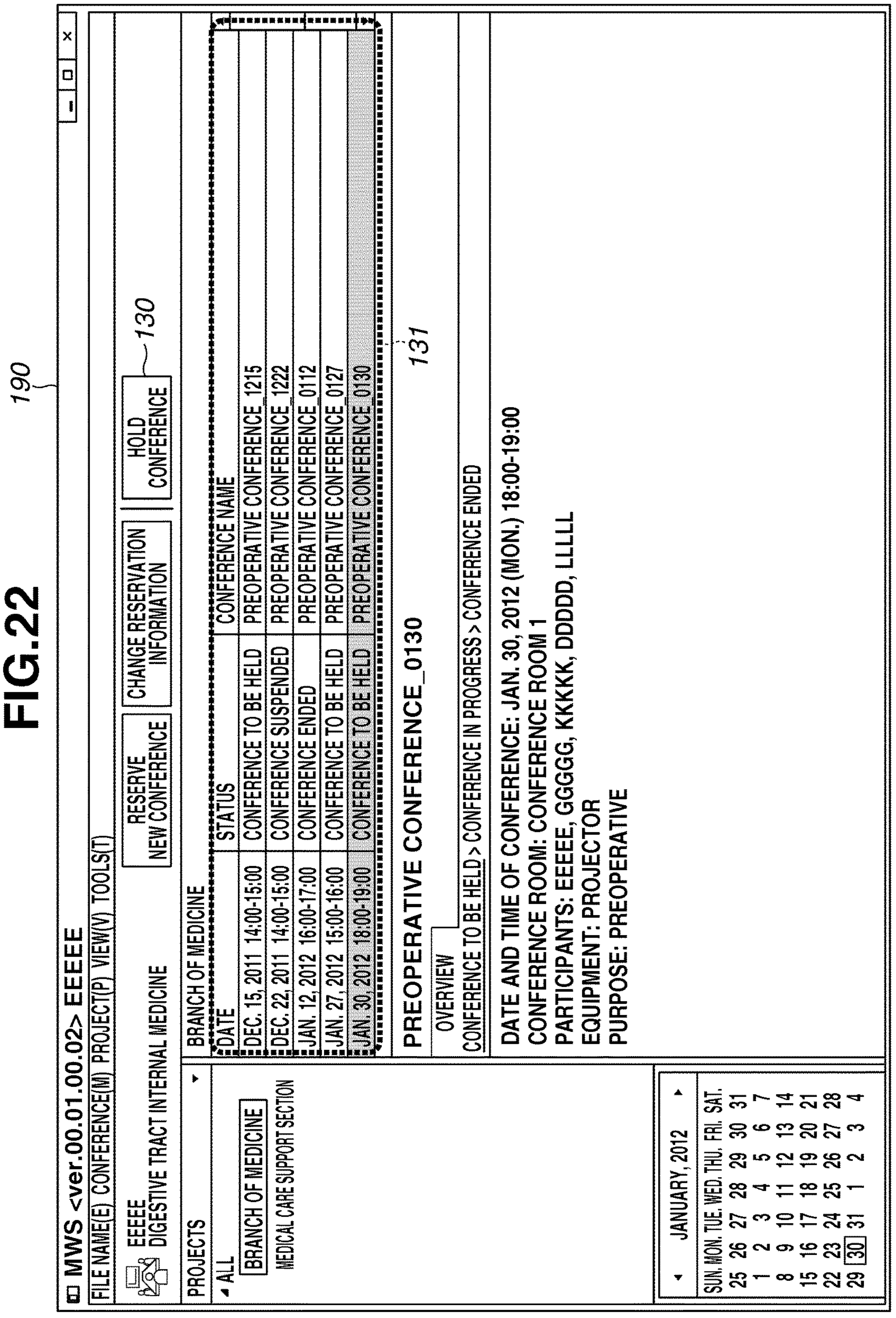
FIG. 22 illustrates an example of a conference list screen.
Figure 23:
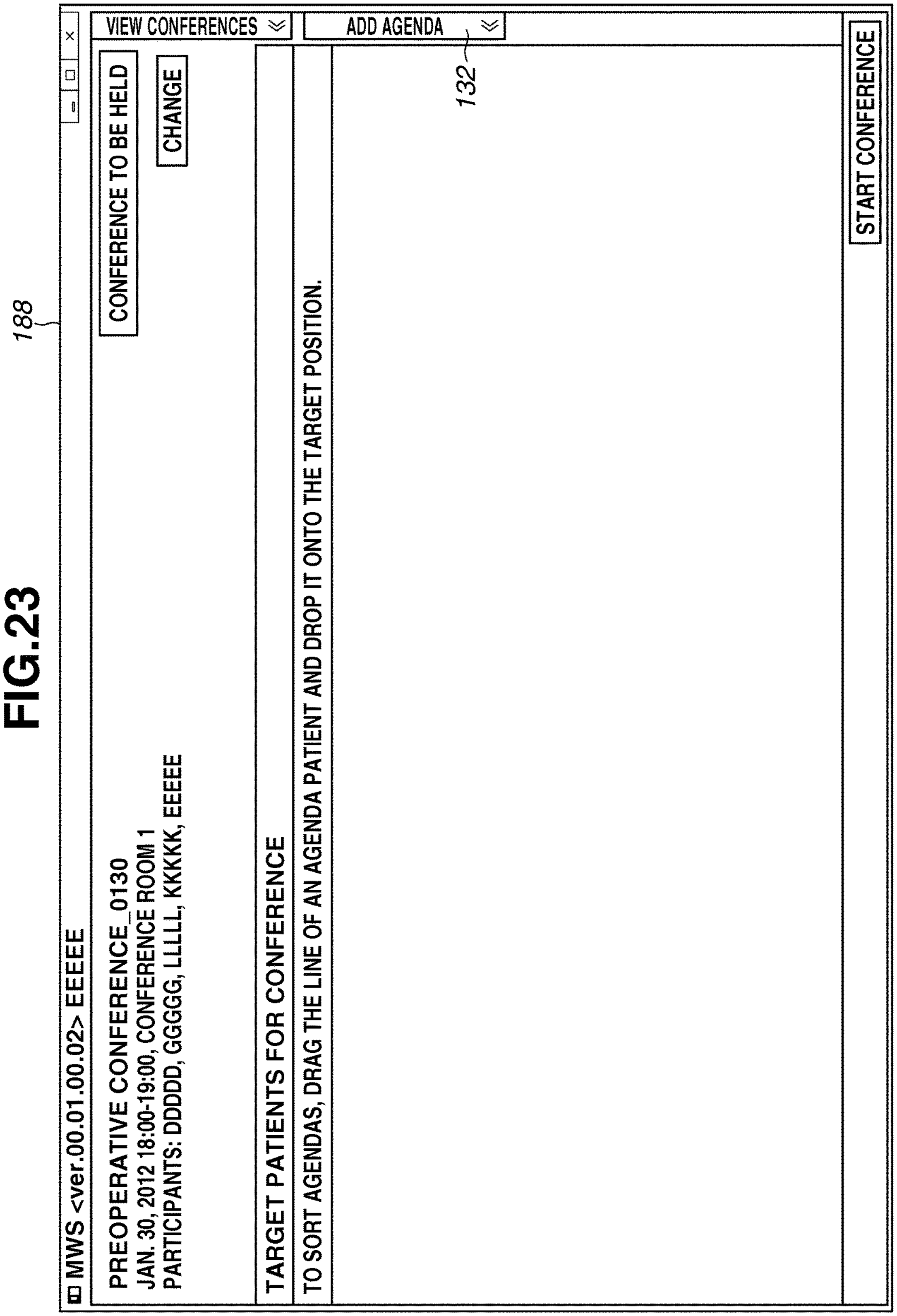
FIG. 23 illustrates an example of a conference screen.

When conference reservation is completed, the conference list screen 190 as illustrated in FIG. 22 is resumed. Then, the user selects a reserved conference in a conference list 131 and then press the HOLD CONFERENCE button 130 to open a conference screen 188 as illustrated in FIG. 23. Then, the user presses the ADD AGENDA button 132 to display a patient search panel 133 as illustrated in FIG. 24. At this timing, it is possible to search for a patient who should be an agenda patient, by using the patient ID and patient name as a key, it is also possible to list only patients for whom the user has prepared materials, as illustrated in a patient list 136 illustrated in FIG. 25, by checking a check box 134 and then pressing a SEARCH button 135. When the user presses an ADD button 137, an agenda list item 138 is appended, as illustrated in FIG. 26. For each list item, it is possible to drag a leftmost section 139 of the patient list 136 and drop it into the bottom left area of the conference screen 188 to append the relevant patient to the agenda. After appending a predetermined patient to the agenda in this way, the user presses the ADD AGENDA button 132 once again to close the patient search panel 133. Conference preparation is completed, as illustrated in FIG. 27.

A second exemplary embodiment of the present invention will be described below. A conference support apparatus according to the present exemplary embodiment generates a summary on a patient basis based on information referred to and input at a medical conference, and manages the summary in association with patient information.

The overall configuration of the conference support apparatus according to the second exemplary embodiment is similar to that illustrated in FIG. 1.

Figure 31:
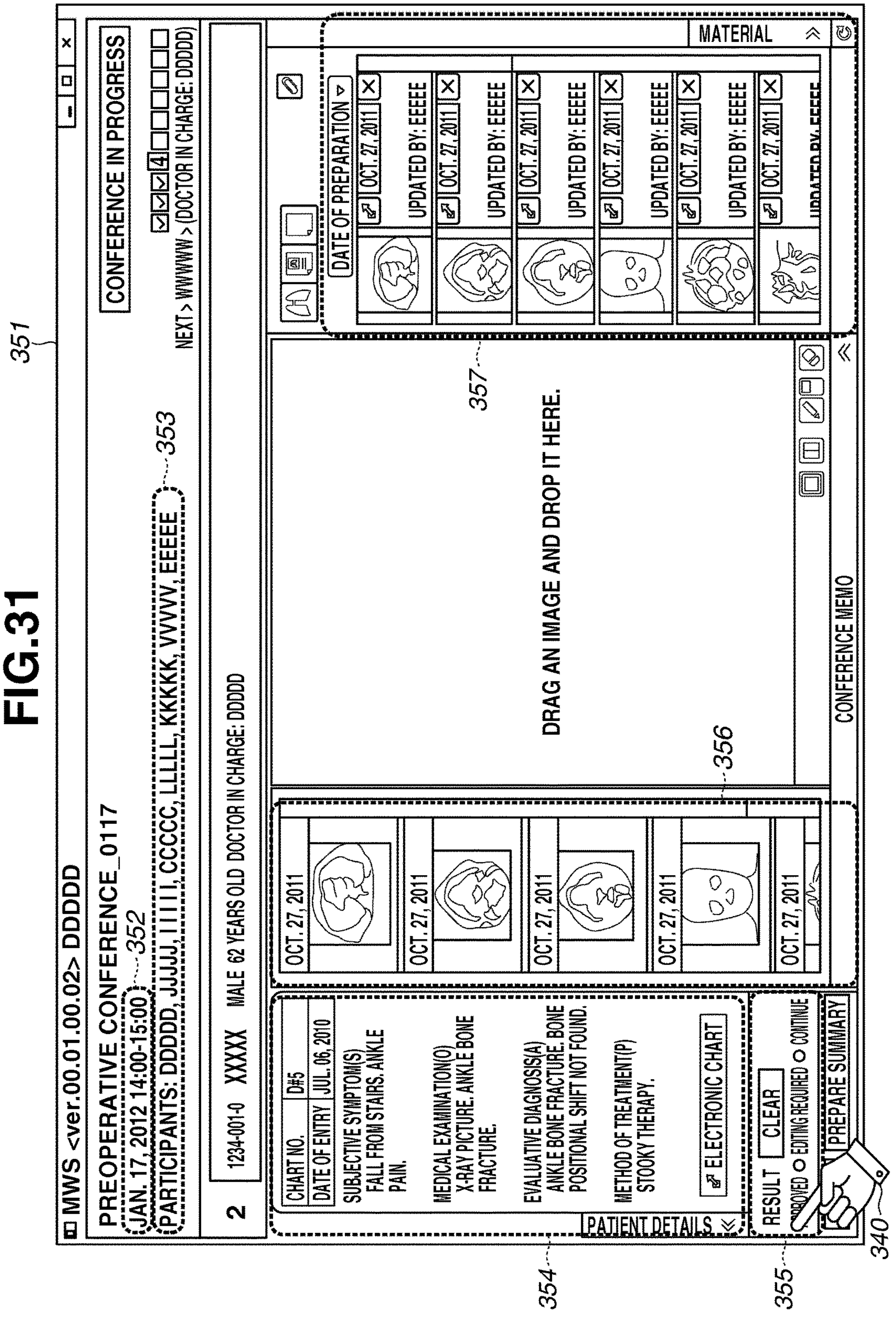
FIG. 31 illustrates a display screen of a conference client apparatus according to a second exemplary embodiment.

FIG. 31 illustrates a screen displayed during a conference by the conference client apparatus 1 according to the second exemplary embodiment. The doctor approves the operation method for each patient by using this screen. The conference screen automatically displays electronic chart information 354 including the operation method pre-input for each patient, pre-collected medical image information 357, relevant day's participant information 353, and conference date information 352. Doctors participating in the conference advance the conference referring to these pieces of information. Images specified by the doctors as a related material during the conference are stored as a summary output image list 356. When a result of the approval of the operation method proposed at the conference is acquired, the user selects "APPROVED", "EDITING REQUIRED", or "CONTINUE" in a result input area 355 to terminate discussions about the target patient.

Figure 32:
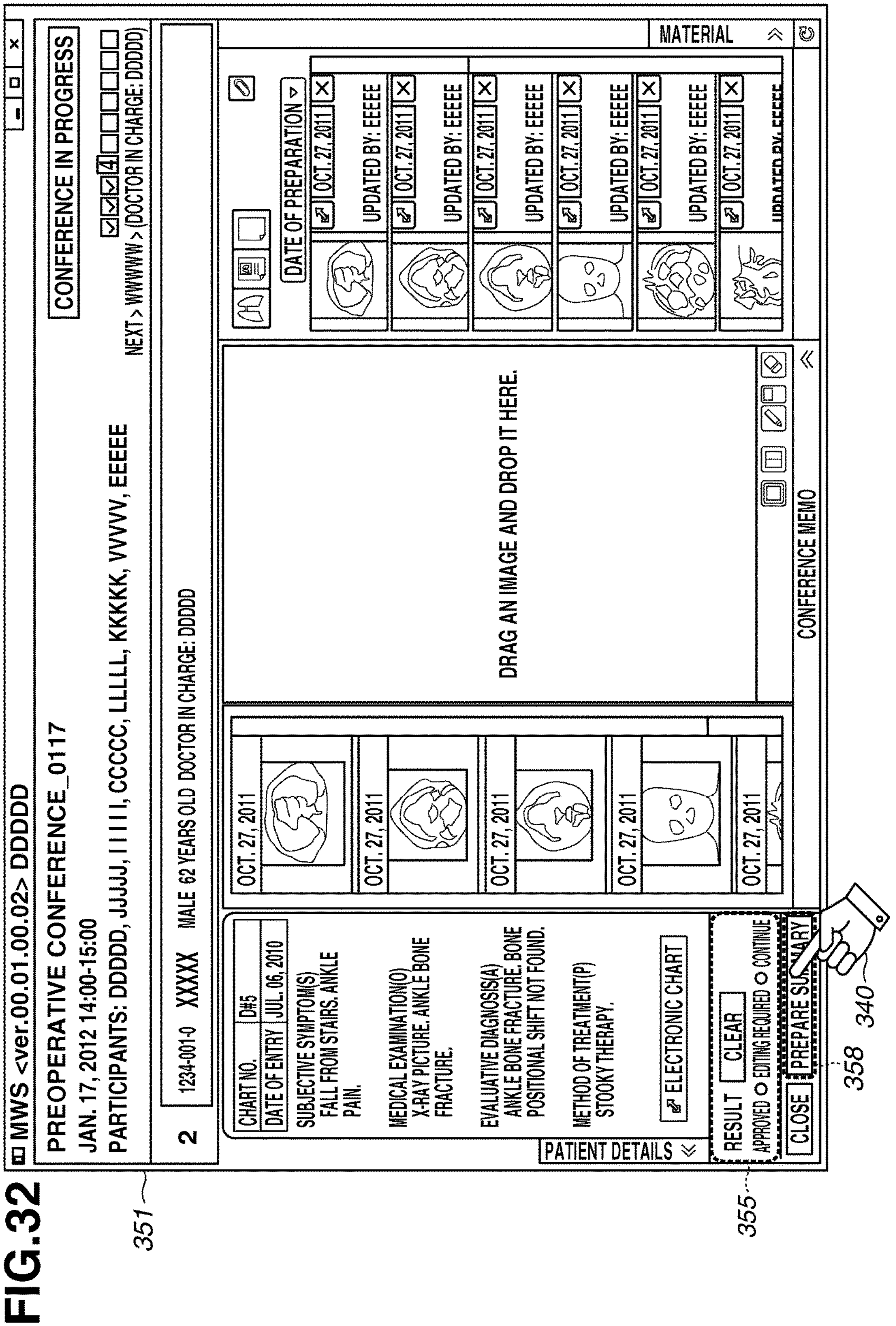
FIG. 32 illustrates a display screen of the conference client apparatus according to the second exemplary embodiment.
Figure 33:
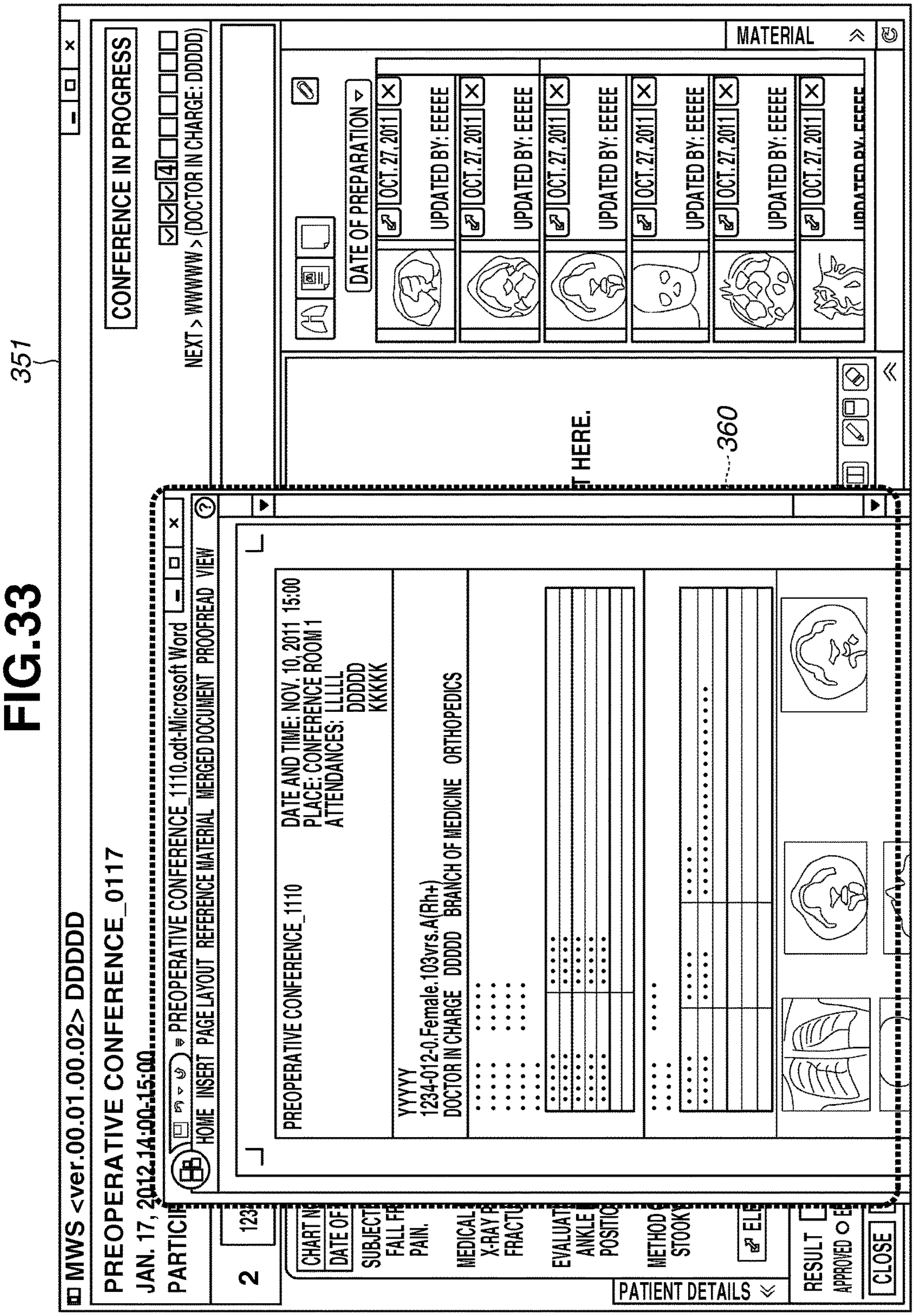
FIG. 33 illustrates a display screen of the conference client apparatus according to the second exemplary embodiment.

FIG. 32 illustrates a screen after the user selects an item in the result input area 355. Referring to FIG. 32, since the result is selected in the result input area 355, the PREPARE SUMMARY button 358 is enabled. At this time, when the doctor presses the PREPARE SUMMARY button 358, summary information 33 for the conference is generated and stored in the file server 3 in a state of being associated with the target patient. The timing at which the user presses the PREPARE SUMMARY button 358 is not limited to a timing immediately after the user selects an item in the result input area 355, but may be a timing after a person in charge appends a conference note after the conference. It is also possible to display an output result after summary output allowing a user to check the contents of the summary. FIG. 33 illustrate an output result 360 displayed immediately after summary output. This allows the user to immediately check the contents of the summary and, if there is a defect in the summary, correct the information on the conference screen, and then output the summary again.

Figure 34:
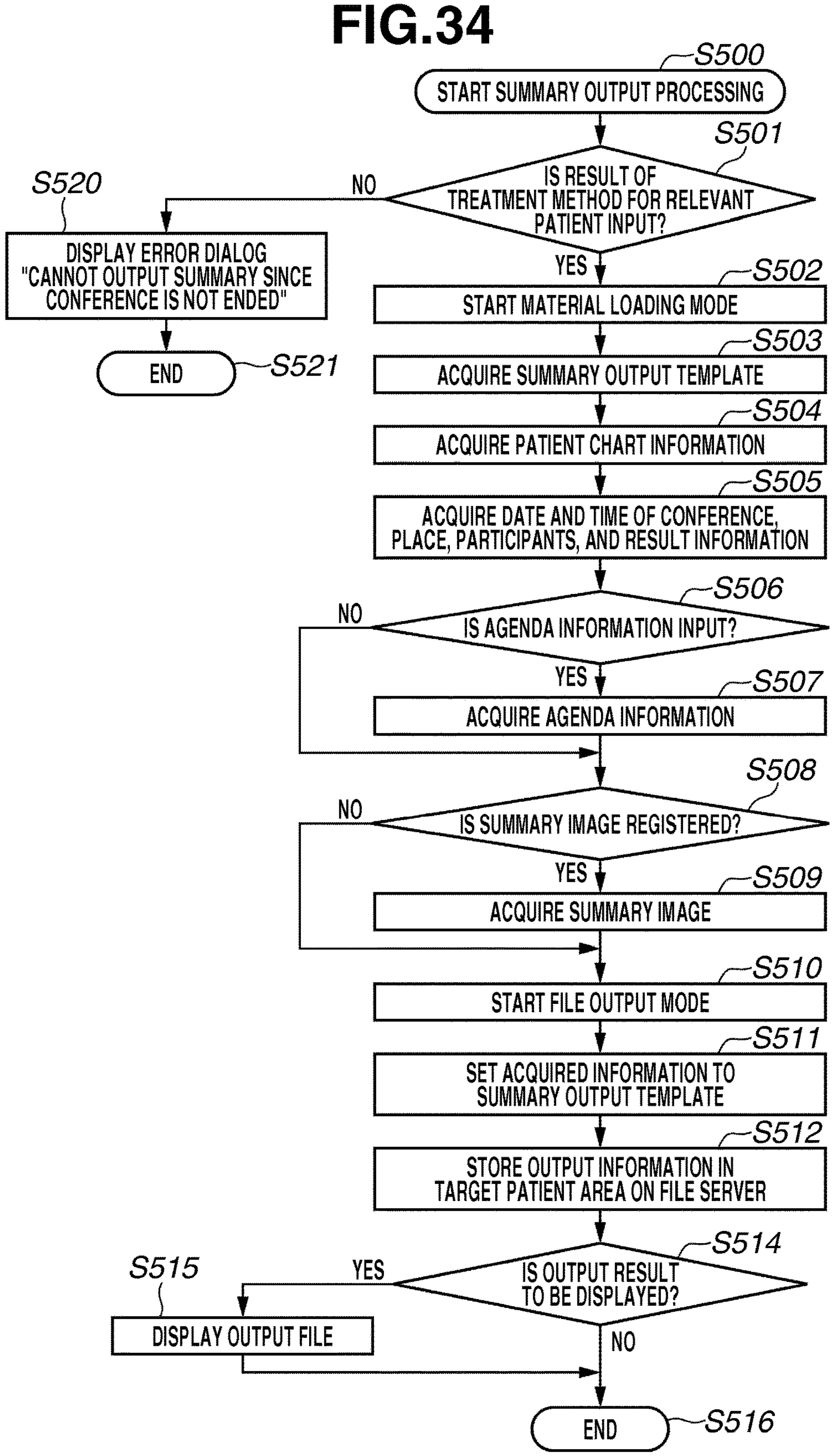
FIG. 34 is a flowchart illustrating summary output processing performed by the conference client apparatus according to the second exemplary embodiment.

The following describes processing performed by the conference client apparatus 1 according to the second exemplary embodiment in detail with reference to FIG. 34. FIG. 34 is a flowchart illustrating summary output processing performed by the conference client apparatus 1 according to the second exemplary embodiment.

In step S500, when the conference client apparatus 1 detects an event of pressing the PREPARE SUMMARY button 358, it starts the summary output processing. In step S501, the conference client apparatus 1 determines whether a conclusion is set for the conference subjected to summary output to the result input area 355. When a conclusion is set for the conference (YES in step S501), then in step S502, the conference client apparatus 1 enters the material loading mode. In steps S502 to S509, the conference client apparatus 1 acquires information required for summary output. In step S503, the conference client apparatus 1 acquires a template for summary output. Insteps S504 and S505, the conference client apparatus 1 acquires patient chart information and information about the date and time, place, participants, and result of the conference. When a conference note is determined to have been input (YES in step S506), then in step S507, the conference client apparatus 1 acquires conference note information. Otherwise (NO in step S506), then in step S508, when a summary image is determined to have been registered (YES in step S508), then in step S509, the conference client apparatus 1 acquires the registered summary image. The conference client apparatus 1 acquire all of these pieces of information from the servers 2 to 8. Although, in this example, the information to be acquired is predetermined information, the relevant information may be dynamically changed depending on the contents of the template. Further, the template may be dynamically changed depending on the conclusion of the conference and the result of diagnosis.

After information gathering, the processing proceeds to step S510 to enter the file output mode. In step S511, the conference client apparatus 1 identifies the type of information required to generate a summary based on the template acquired in step S503, extracts necessary information from the information acquired in steps S504 to S509, and applies it to the template. In step S512, the conference client apparatus 1 stores in the binder 302 (for managing information about the target patient as a summary file 33) the template to which various information is applied, thus establishing association with the patient. Finally, when the output result is determined to be confirmed (YES in step S514), then in step S515, the conference client apparatus 1 displays the summary file 33.

Otherwise, when summary output is instructed for a patient with whom the result is not input (NO in step S501), then in step S520, the conference client apparatus 1 displays an error dialog and cancels the summary output processing (since summary output is performed for a patient with whom the result has been acquired).

As described above, the present exemplary embodiment allows the user of the conference support apparatus to generate a summary without troublesome work, i.e., without gathering related materials or arranging documents. The present exemplary embodiment also enables managing the generated summary in a state of being associated with the patient.

The operation may be simplified by automatically outputting a summary not only when the PREPARE SUMMARY button 358 is pressed but also when a result input to the result input area 355, a conference end event, or a conference screen end is detected.

Further, a target patient list screen may be separately prepared to specify patients subjected to summary output. FIG. 35 illustrates a screen displaying a list of patients subjected to approval in the conference, and that a result of "APPROVED" is acquired for all of the patients. In this state, a summary may be generated for a specific patient by pressing a PREPARE SUMMARY button 372 provided for each patient, or summaries may be collectively output for all of the patients. Further, summaries may be automatically output for all of the patients when a conference end event is detected.

In a third exemplary embodiment of the present invention, the medical conference support system advances a conference in cooperation with the electronic chart system 151, a medical image management system, the examination reporting system, an image management system, and the file server 3 in the hospital. In particular, the present exemplary embodiment is characterized in material preparation status display, conclusion status display, conference progress status display, external system reference, non-DICOM image reference, summary material logging, and simplified conclusion input.

A typical configuration of the third exemplary embodiment is similar to that illustrated in FIG. 1.

Since the conference client apparatus 1 and the conference server 2 have a similar hardware configuration, only the conference client apparatus 1 will be described in detail below. The UI device 101 is a mouse, a digitizer, or a keyboard which is used to input user instructions to the conference client apparatus 1. The conference client apparatus 1 includes the CPU 102 and the RAM 103. When the CPU 102 loads a program from a program storage area 106 into the RAM 103 and then interprets and executes it, the conference client apparatus 1 is able to perform various control and calculations and display UIs. The communication I/F 104 connected with the network 9 serves as a communication interface between the conference client apparatus 1, the conference server 2, and the servers 3 to 8 in the hospital. The UI display 105 is an LED display or a liquid crystal panel for displaying the status and processing of the conference client apparatus 1. The conference client apparatus 1 further includes the program storage area 106 and the data storage area 107. Although these two storage areas can be implemented by using a hard disk or a flash memory, the present invention, of course, does not depend on a specific storage medium. The conference client apparatus 1 stores the conference material 10 in the data storage area 107. The conference material 10 may be stored in the file server 3. The conference server 2 stores material registration information 20 and the conference information 21 in the data storage area 207.

Conference materials are collected for each individual patient or case and managed on a binder basis. However, entities of conference materials are not stored in binders but only management information of conference materials is stored in binders. The file server 3 includes a binder pool 301 in which a binder 302 is generated for each individual patient or case. The binder pool 301 may be included in the data storage area 207 of the conference server 2. In each binder 302, the presentation image 30 and the thumbnail 31 are generated for each registered material. Since medical images are difficult to handle because of large sizes, the presentation image 30 more suitable for display during the conference is generated. Information of a handwritten note taken for an image during the conference is stored in each binder 302 as the annotation 32. Further, a document summarizing a conclusion of the conference and images used in the conference is stored in each binder 302 as the summary 33.

This configuration enables the medical conference support system operating on the conference client apparatus 1 and a conference server 2 to advance the conference in cooperation with the electronic chart system 151 and the medical image management system connected to the network 9.

The network 9 illustrated in FIG. 1 may be an intranet operated in a hospital or organization, or the Internet. Further, the network 9 may be a wired or wireless network.

Since the electronic chart system 151, the medical image management system, the examination reporting system, the image management system, the file server 3, and the order system are widely used apparatuses, descriptions of the hardware configuration and operation flows will be omitted.

Figure 36:
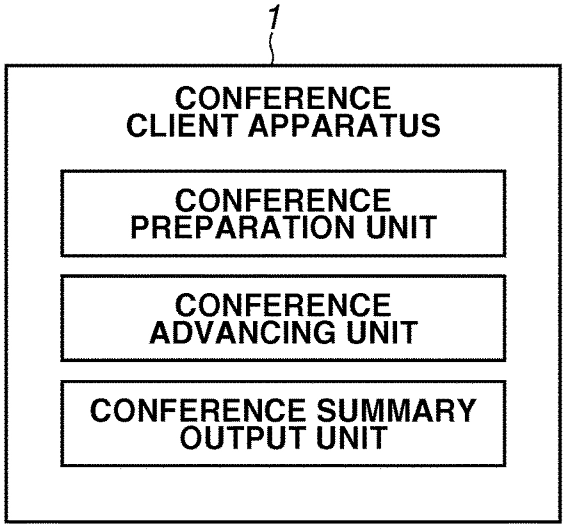
FIG. 36 schematically illustrates a program configuration of a conference client apparatus according to a third exemplary embodiment.

FIG. 36 schematically illustrates a program configuration of the conference support apparatus. The conference client apparatus 1 includes a conference preparation unit configured to prepare a conference material, such as patient examination data, and set a conference agenda, a conference advancing unit configured to support the progress of the conference referring to the conference material of the set agenda during the conference, and a conference summary output unit configured to generate and distribute a result of the conference as a summary. These programs are stored in a memory and storage device of each individual apparatus and executed by the CPU thereof. If necessary, these programs control the network I/F, the USB interface, and various controllers. These program detect user operations and automatic operations based on communication commands via a network interface, mouse, keyboard, and remote control operations via peripheral controllers, and voice commands via microphone input.

This configuration enables the medical conference support system according to the present invention to advance the conference in cooperation with the electronic chart system 151, the medical image management system, the examination reporting system, the image management system, and the file server 3 in the hospital. In particular, the present exemplary embodiment is characterized in material preparation status display, conclusion status display, conference progress status display, external system reference, non-DICOM image reference, summary material logging, and simplified conclusion input.

The following describes operations of each program with reference to accompanying drawings, on the premise that setting information (read when each program is activated) is read from a nonvolatile storage device and the network 9 when each individual apparatus is activated, and stored in a memory and storage device of each individual apparatus. These setting values include specified values at the time of shipment and user-defined values set by using other tools.

Figure 37:
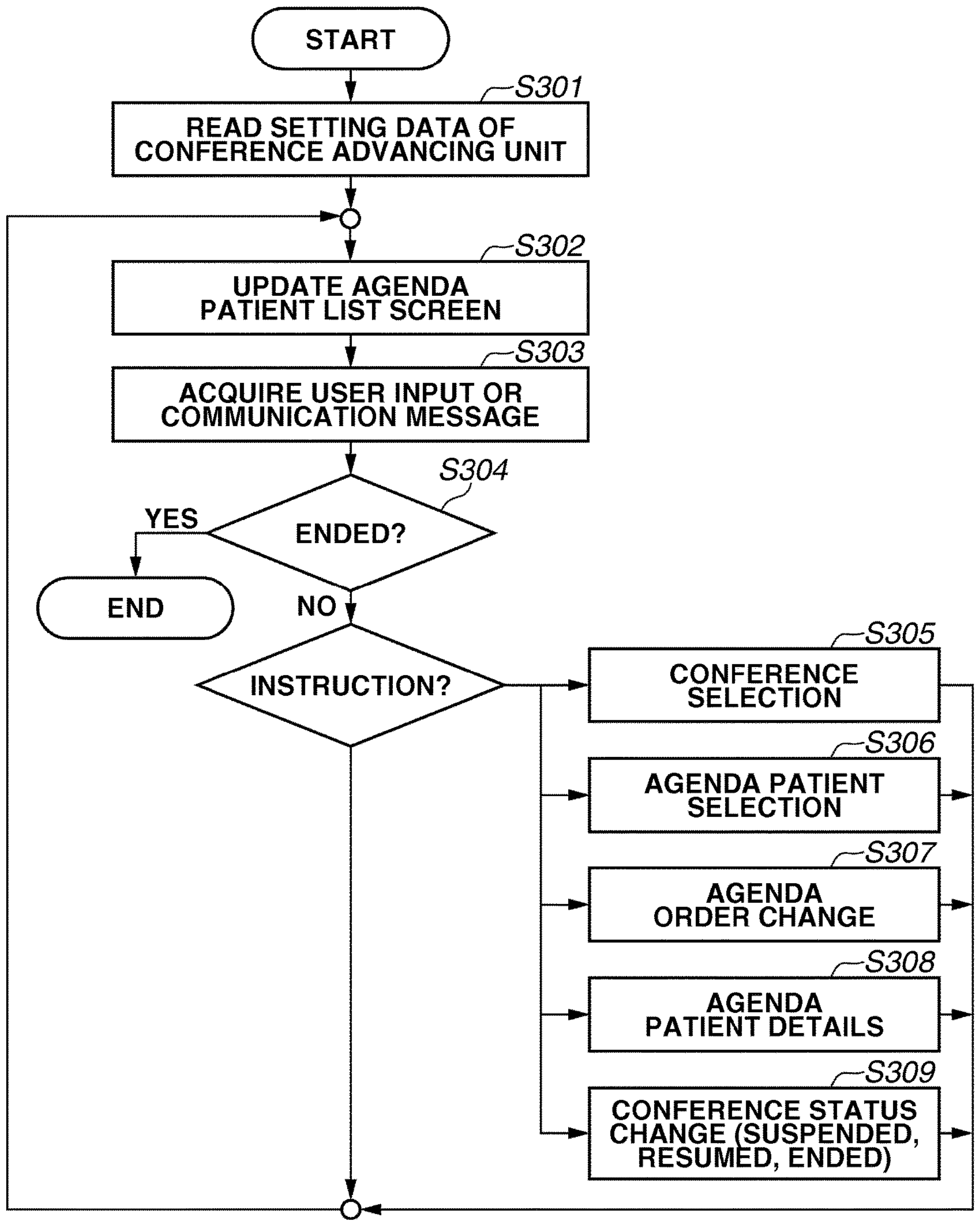
FIG. 37 is a flowchart illustrating the operation of an agenda list screen of a conference advancing unit of the conference client apparatus according to the third exemplary embodiment.

FIG. 37 is a flowchart illustrating the operation of the agenda list screen of the conference advancing unit of the conference client apparatus 1. In the agenda list screen, the conference advancing unit displays the conference information 21, and the agenda patient list of a selected conference, receives an operation from the user (doctor or other medical staff), and performs processing according to the operation.

In step S301, the conference client apparatus 1 reads the setting information of the conference advancing unit. In step S302, the conference client apparatus 1 updates the agenda patient list screen. In step S303, the conference client apparatus 1 acquires an user input or communication message, and performs the following processing according to the user input or communication message. When the user input or communication message is determined to be an end instruction (YES in step S304), the processing of the conference advancing unit ends. When the user input or communication message is determined to be a conference selection instruction, then in step S305, the conference client apparatus 1 displays the conference list screen (FIG. 39A) for conference selection and then waits for the next instruction. When the user input or communication message is determined to be a agenda patient selection instruction, then in step S306, the conference client apparatus 1 displays the patient search image (FIG. 39C) for patient selection and then waits for the next instruction. When the user input or communication message is determined to be an agenda order change instruction, then in step S307, the conference client apparatus 1 changes the order of a patient specified in the agenda patient list screen (FIG. 39E) and then waits for the next instruction. When the user input or communication message is determined to be a agenda patient details instruction, then in step S308, the conference client apparatus 1 displays the agenda patient details screen (FIG. 40A) and then waits for the next instruction. When the user input or communication message is determined to be a conference status change instruction, then in step S309, the conference client apparatus 1 changes the conference status specified in the agenda patient list screen (FIGS. 39D, 47B, and 47C) and then waits for the next instruction. After completion of the processing in steps S305 to S309, the processing returns to step S302 to repeat the above-described processing.

Figure 38:
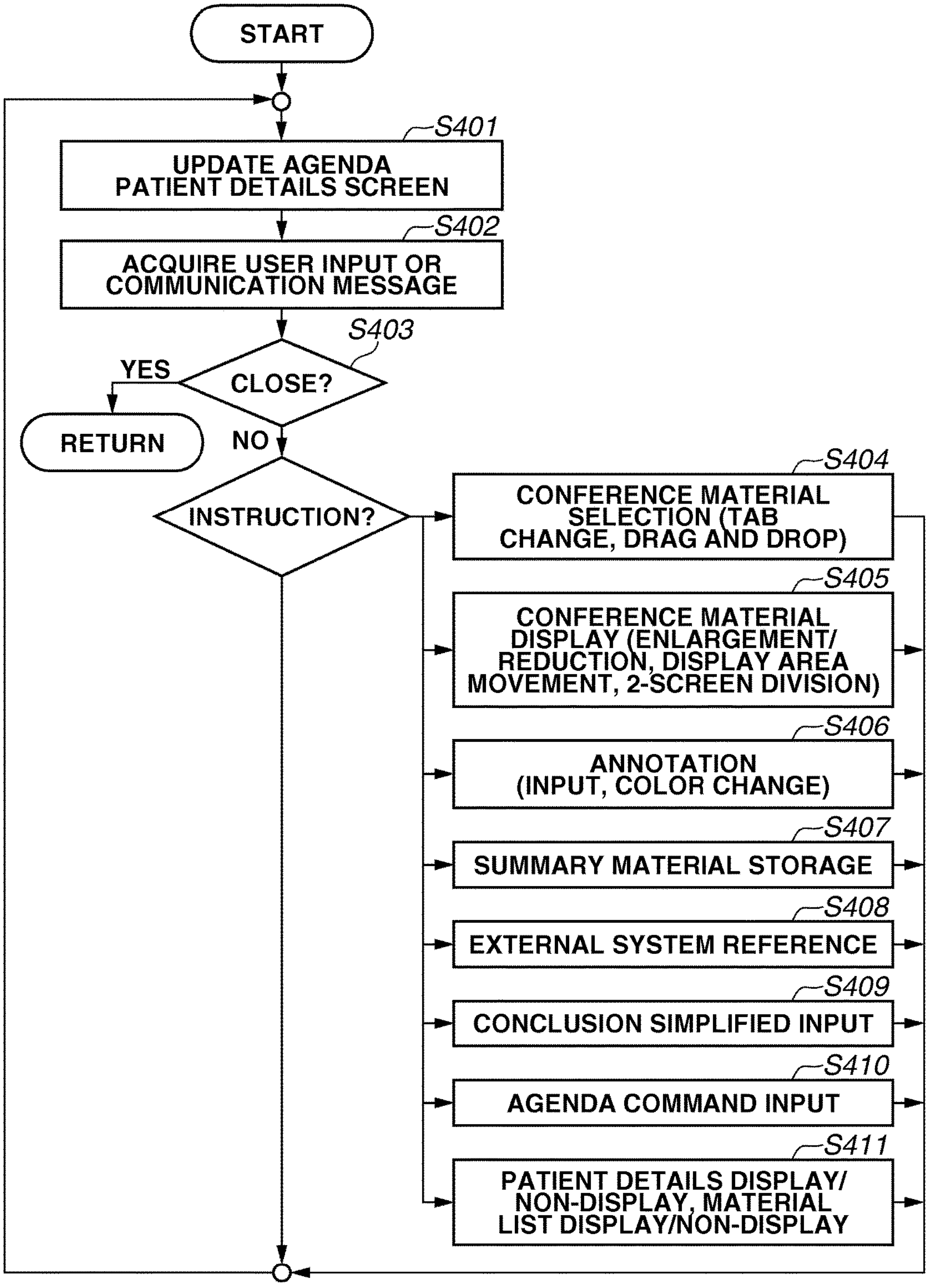
FIG. 38 is a flowchart illustrating the operation of an agenda patient details screen of the conference advancing unit of the conference client apparatus according to the third exemplary embodiment.

FIG. 38 is a flowchart illustrating the operation of the agenda patient details screen of the conference advancing unit of the conference client apparatus 1. In the agenda patient details screen, the conference advancing unit displays medical care information, examination image, various reports, and non-DICOM image of a select agenda patient, receives an operation from the user (doctor or other medical staff), and performs processing according to the operation.

Figure 43A:
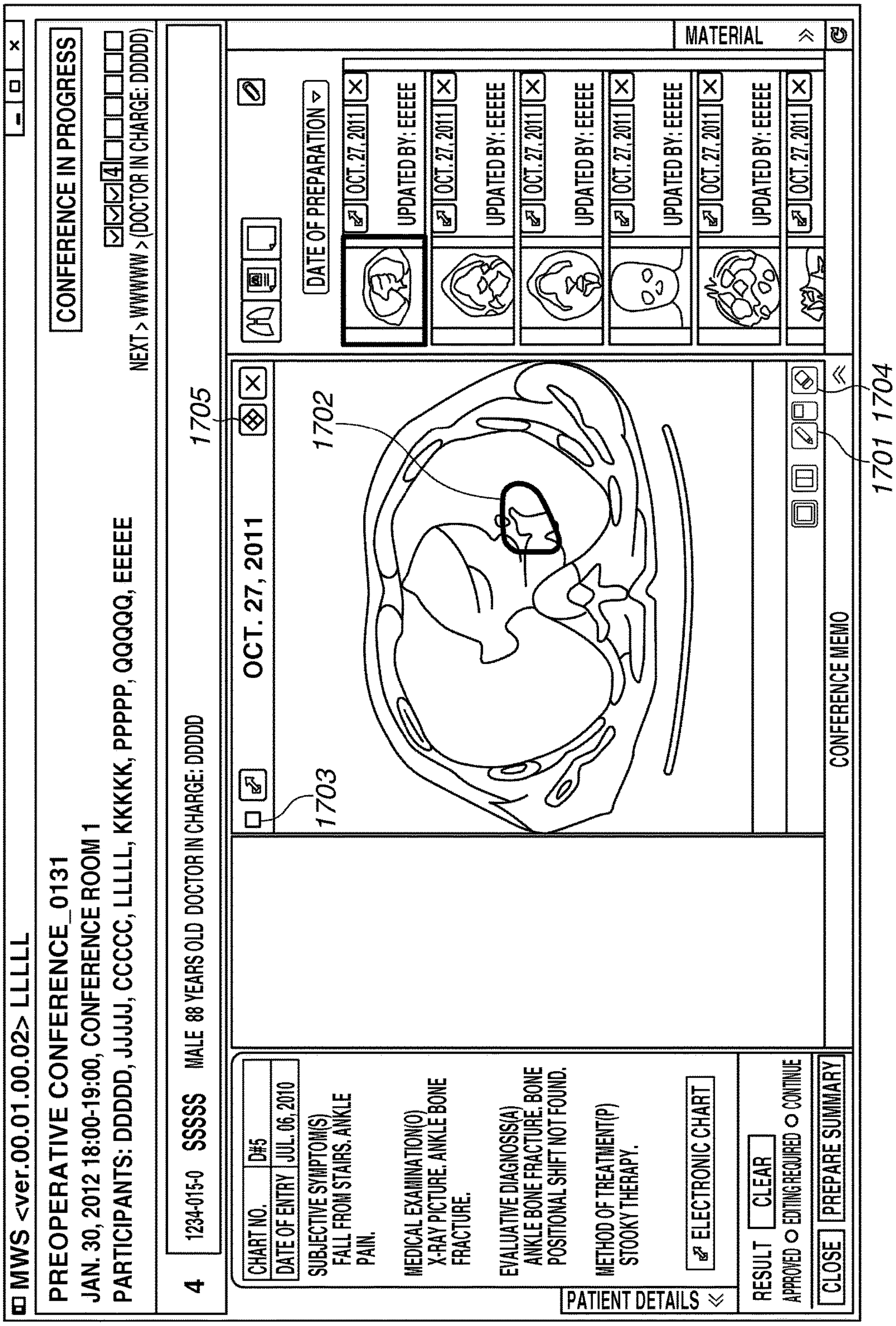
FIG. 43A illustrates annotation and automatic summary setting for a material on the conference client apparatus.
Figure 43B:
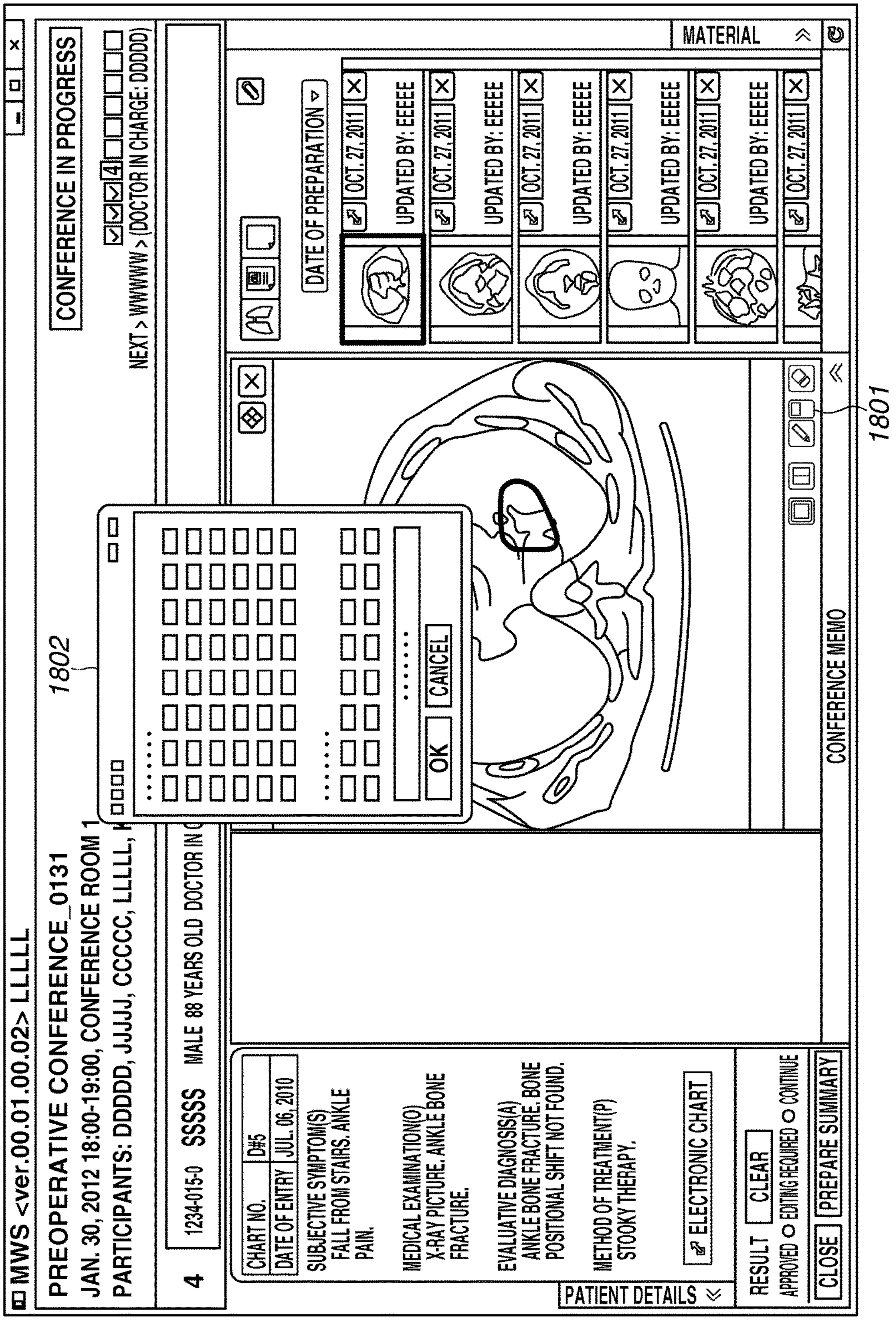
FIG. 43B illustrates annotation color selection on the conference client apparatus.
Figure 43C:
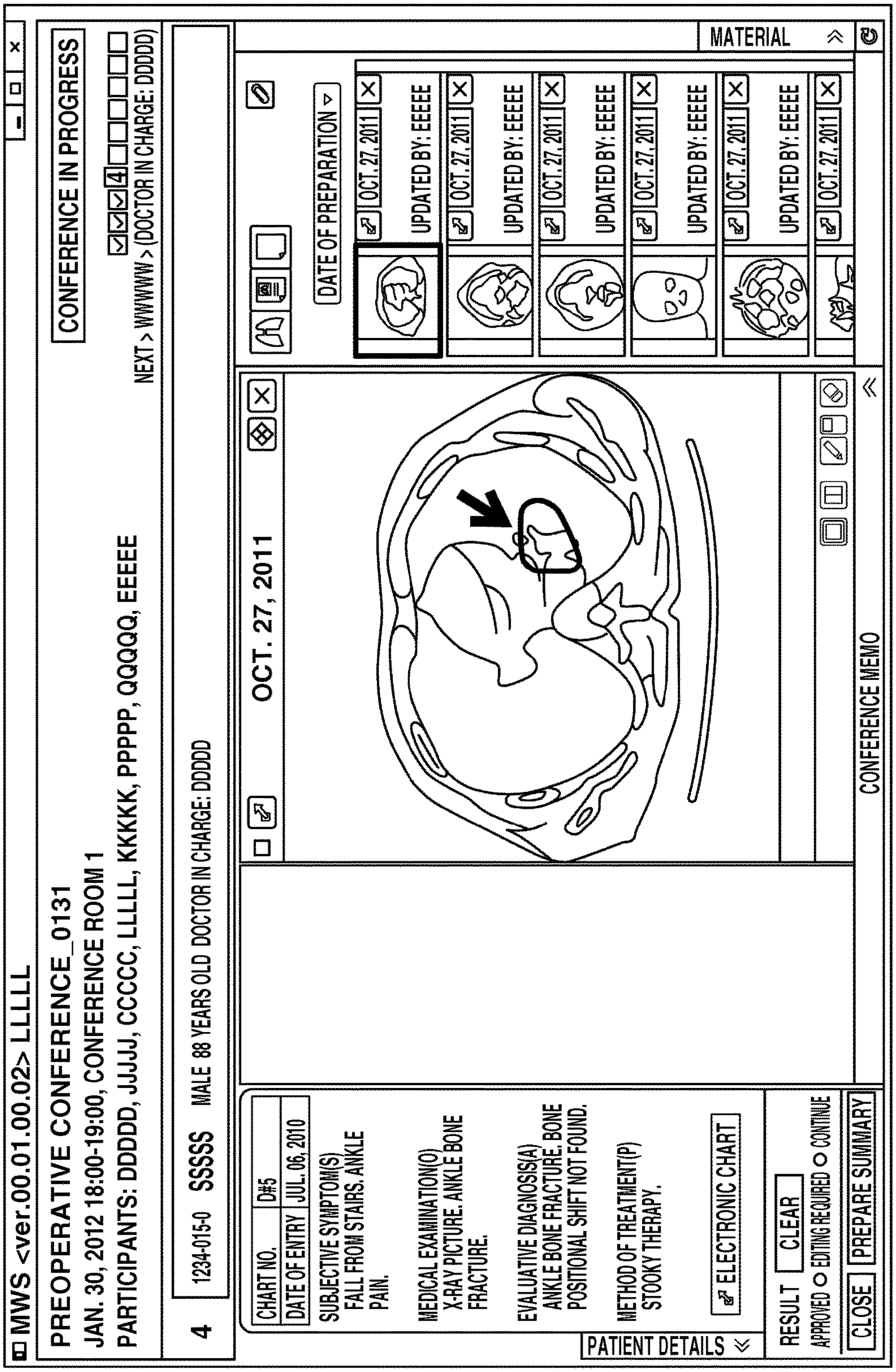
FIG. 43C illustrates annotation setting with a different color on the conference client apparatus.
Figure 43D:
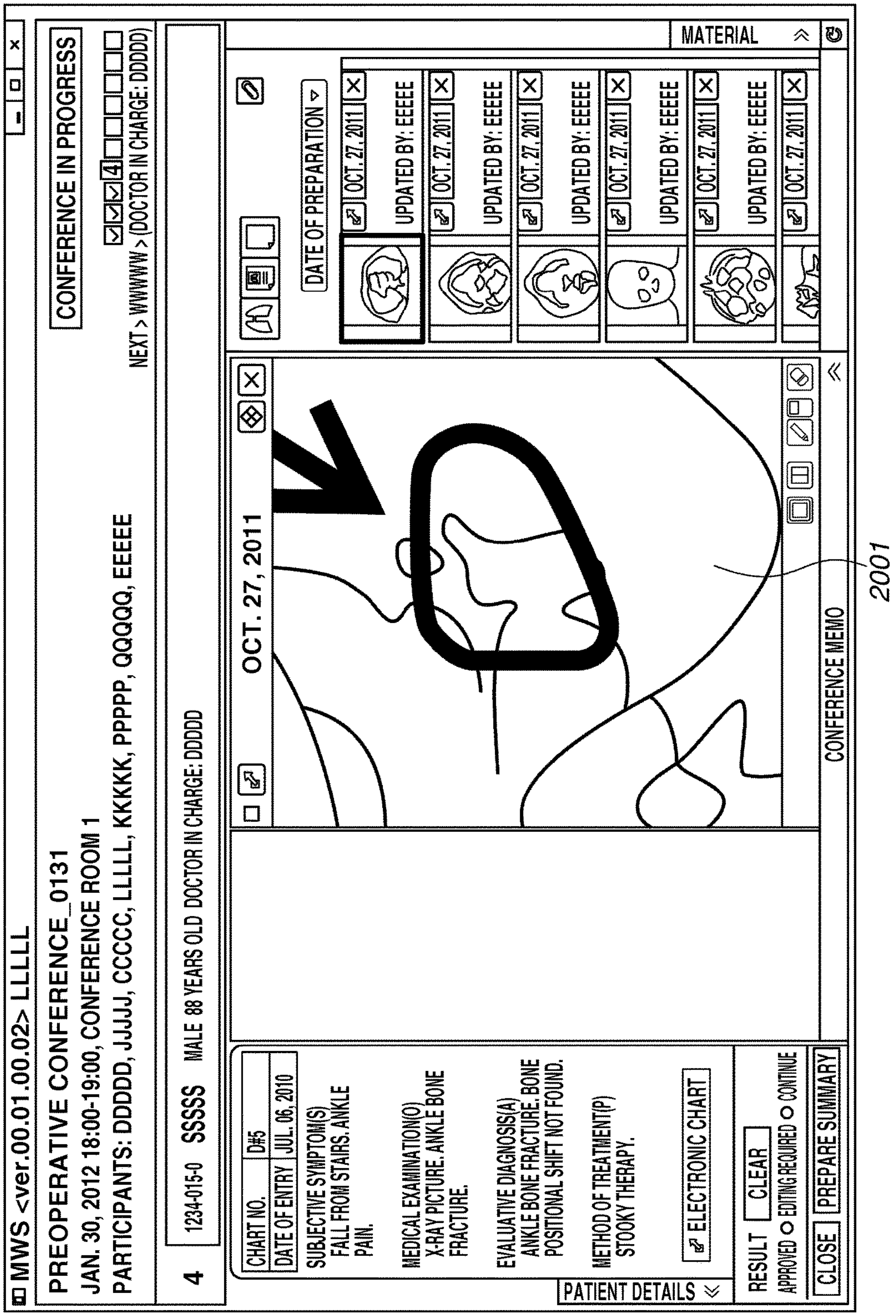
FIG. 43D illustrates scale display for an agenda material on the conference client apparatus.
Figure 44A:
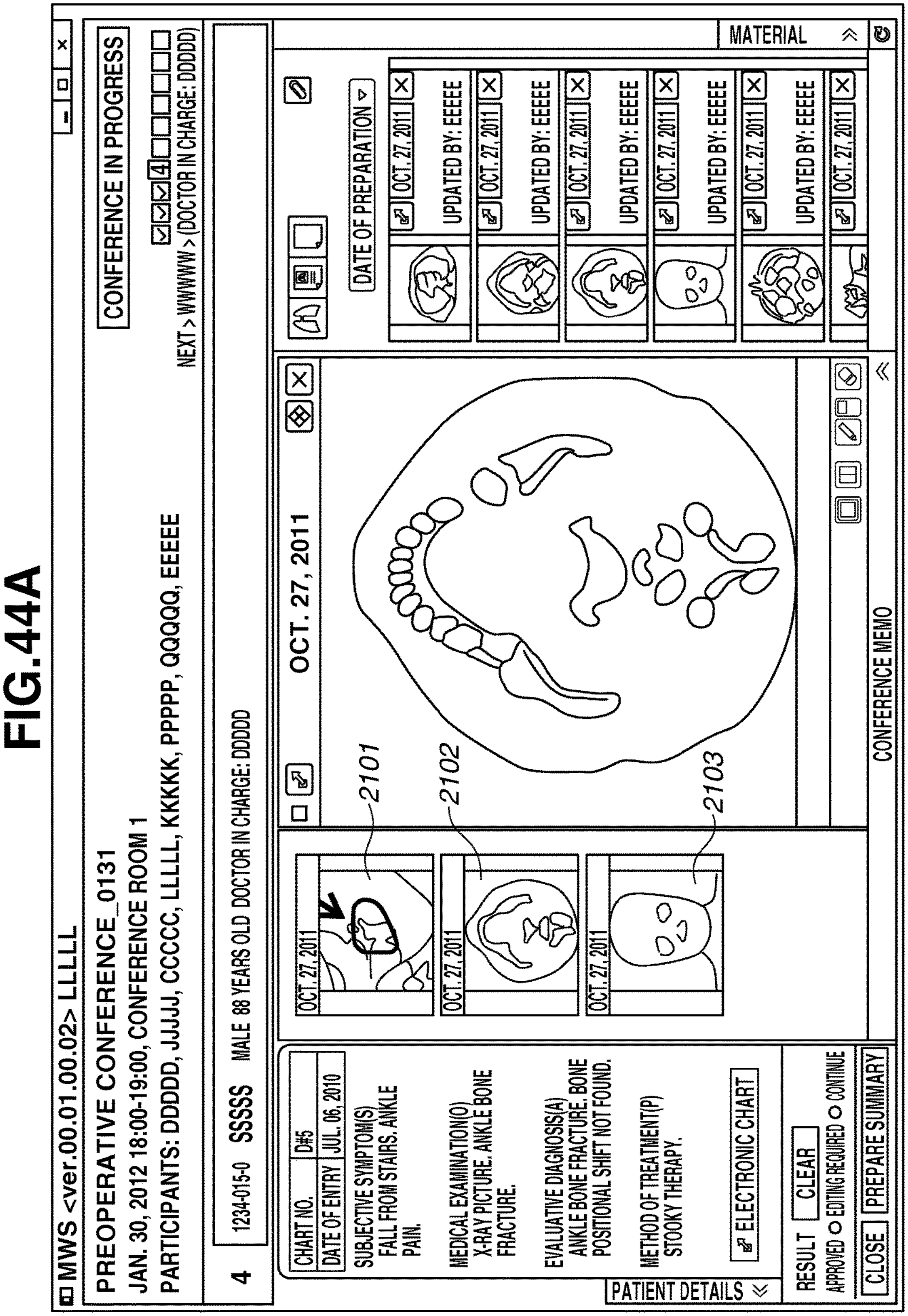
FIG. 44A illustrates materials set for summary on the conference client apparatus.
Figure 44B:
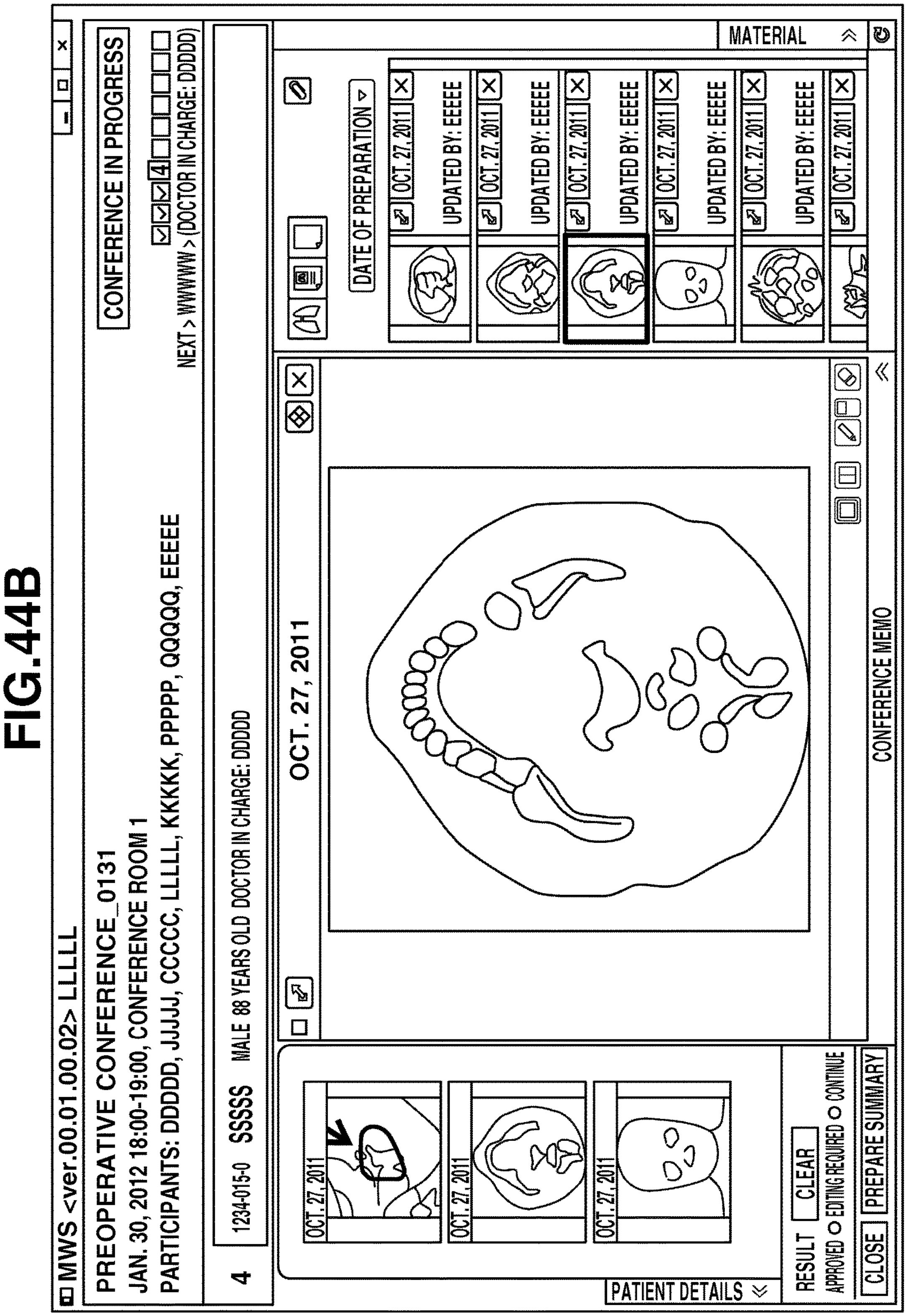
FIG. 44B illustrates a state where a medical care information display area is hidden on the conference client apparatus.
Figure 44C:
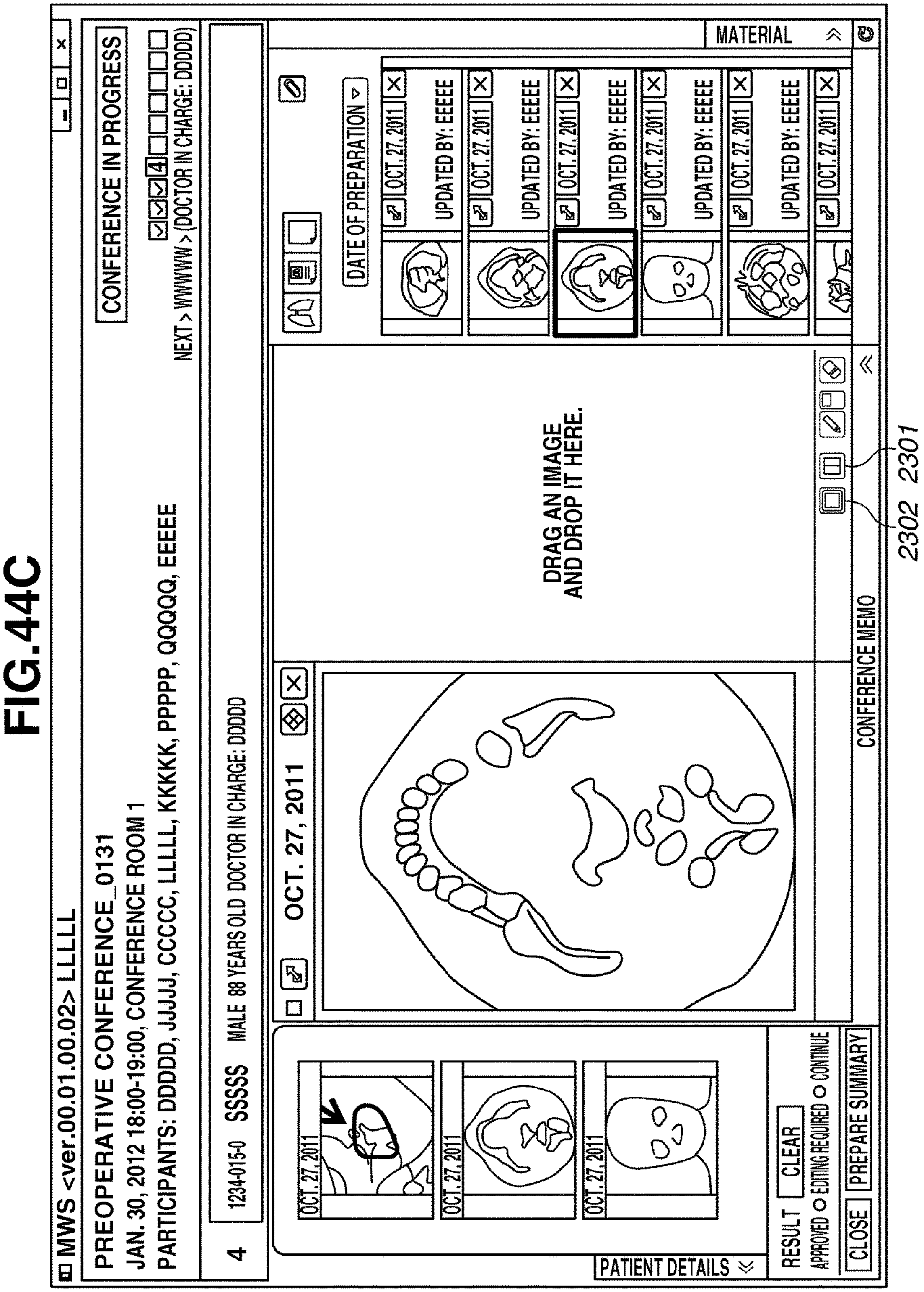
FIG. 44C illustrates a 2-division material screen on the conference client apparatus.
Figure 44D:
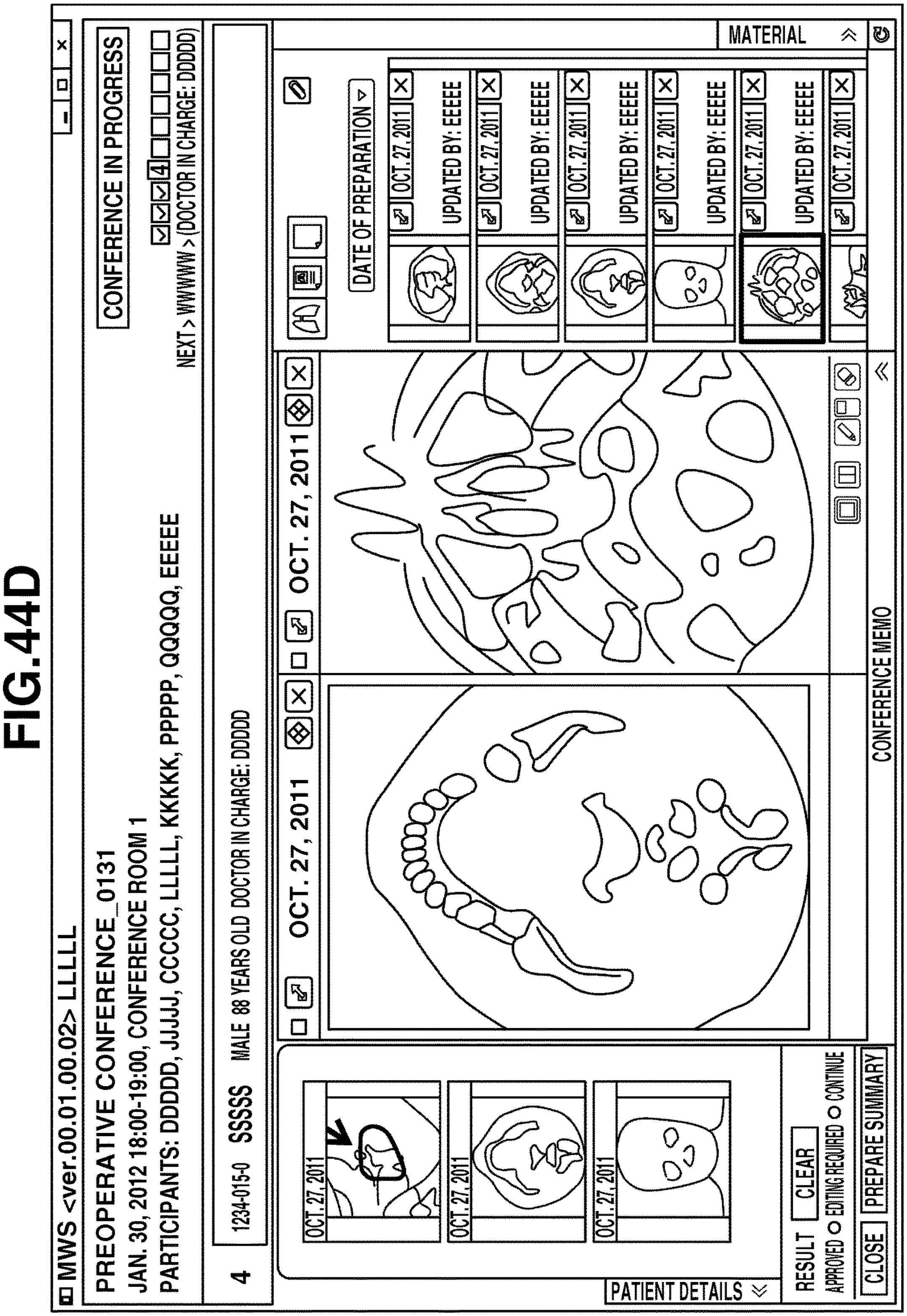
FIG. 44D illustrates a 2-division material screen on the conference client apparatus.

In step S401, the conference client apparatus 1 updates the agenda patient details screen. In step S402, the conference client apparatus 1 acquires a user input or communication message, and performs the following processing according to the contents of the user input or communication message. When the user input or communication message is determined to be a close instruction (YES in step S403), the processing returns to the agenda patient details screen. Otherwise (NO in step S403), the conference client apparatus 1 performs the following processing according to each instruction. When the user input or communication message is determined to be a conference material selection instruction, then in step S404, the conference client apparatus 1 selects a specified material and then waits for the next instruction. Processing in this step includes changing conference material tabs and an drag-and-drop operation for the workspace (FIGS. 40B, 41A, 41B, 42A, and 42B). When the user input or communication message is determined to be a conference material display instruction, then in step S405, the conference client apparatus 1 displays conference materials and then waits for the next instruction. Processing in this step includes enlargement/reduction, viewing area movement, and 2-division screen display (FIGS. 43D, 44C, and 44D). When the user input or communication message is determined to be an annotation instruction, then in step S406, the conference client apparatus 1 supplies an annotation (note) to the conference materials of the workspace and then waits for the next instruction. Processing in this step includes annotation input and color change (FIGS. 43A, 43B, and 43C). When the user input or communication message is determined to be a summary material storage instruction, then in step S407, the conference client apparatus 1 stores the conference material of the workspace for summary and then waits for the next instruction. Processing in this step includes automatic summary setting and summary material display (FIGS. 43A and 44A). When the user input or communication message is determined to be an external system reference instruction, then in step S408, the conference client apparatus 1 calls an external system, such as the electronic chart system 151 and the PACS viewer 160, and waits for the next instruction. When the user input or communication message is determined to be a conclusion simplified input instruction, then in step S409, the conference client apparatus 1 inputs a conclusion of discussions about diagnostic findings and treatment plan for the relevant agenda patient (FIG. 46B), and then waits for the next instruction. When the user input or communication message is determined to be a agenda comment input instruction, then in step S410, the conference client apparatus 1 inputs a comment about the relevant agenda patient (FIG. 46C) and then waits for the next instruction. When the user input or communication message is determined to be a patient details display/hide or material list display/hide instruction, then in step S411, the conference client apparatus 1 displays or hides the patient details or material display on the screen (FIGS. 44B and 44E) and waits for the next instruction. After completion of the processing in steps S404 to S411, the processing returns to step S401 to repeats the above-described processing.

The following describes screens displayed on the UI display 105 of the conference client apparatus 1 by the conference advancing unit of the conference client apparatus 1. These screens are displayed on the UI display (display controller) 105 of the conference client apparatus 1, and operated based on an input from UI device 101.

FIG. 39A illustrates a screen of the conference advancing unit of the conference client apparatus 1 before starting a conference. When the conference client apparatus 1 acquires required information from the conference server 2, the conference client apparatus 1 automatically presents the latest conference for which a user (doctor or other medical staff) using the conference client apparatus 1 is set as a participant. A conference status display area 501 includes preset name, date and time, place, and participants of the conference displayed on the left-hand side, and a conference status (CONFERENCE TO BE HELD in this example) and a CHANGE button displayed on the right-hand side. When the user presses the CHANGE button, the conference client apparatus 1 calls the conference preparation unit allowing the user to change the name, date and time, place, and participants of the conference. An agenda patient list display area 502 displays a list of patients preset as an agenda patient by the conference preparation unit. Patient information of each agenda patient includes the basic patient information (patient ID, name, sex, and age), name of the doctor in charge, material preparation status icons, an agenda display button, a conclusion display area, and a PREPARE SUMMARY button.

Figure 39B:
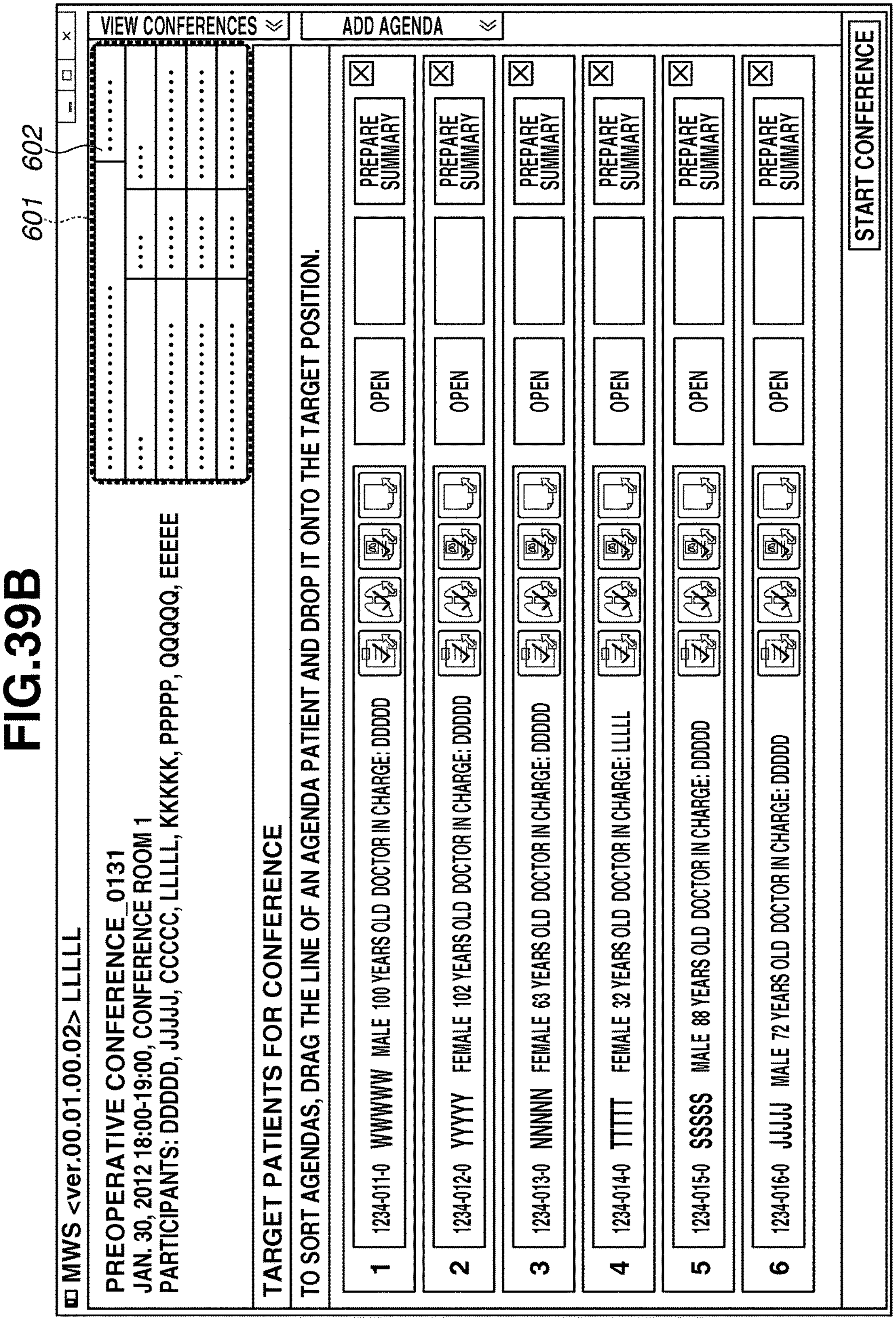
FIG. 39B illustrates a conference selection operation on the conference client apparatus before starting a conference.

When the user presses a VIEW CONFERENCES button 503, the screen illustrated in FIG. 39B appears. When the user presses a SELECT PATIENT button 504, the screen illustrated in FIG. 39C appears. When the user presses a START CONFERENCE button 505, the screen illustrated in FIG. 39D appears. Material preparation status icons 506 indicate material preparation statuses of each individual agenda patient included in the agenda patient list display area 502. In the present exemplary embodiment, the material preparation status icons 506 indicate chart information (diagnostic findings and treatment plan), examination image information (DICOM images), report information (radiographic image interpretation report and pathology diagnostic report), and other information (camera images and Schema diagram), from left to right. The material preparation status icons 506 indicate preparation statuses of respective types of conference materials for the relevant patient in easily viewable form.

The material preparation status icons 506 also serve as buttons for calling (activating) corresponding external systems which prepare respective types of conference materials. Specifically, a chart information icon activates the electronic chart system 151, an examination image information icon activates the PACS viewer 160, a report information icon activates a report viewer, and other information icon activates a file browser. An agenda display button 507 displays an agenda. When the user presses an OPEN button 507, the screen illustrated in FIG. 40A appears. A conclusion display area 508 displays a conclusion. When the user presses a PREPARE SUMMARY button 509, the conference client apparatus 1 calls the conference summary output unit.

FIG. 39B illustrates a conference selection operation on the conference client apparatus 1 before starting a conference. A conference selection panel 601 is used to select a conference. When the user presses the VIEW CONFERENCES button 503, the conference selection panel 601 appears from the right in a sliding way. The conference selection panel 601 displays a list of conferences to which the user is assigned as a participant. When the user selects a desired conference from the list, the conference status display and the agenda patient list change. A VIEW CONFERENCES button 602 is displayed at the top of the conference selection panel 601. When the user presses the VIEW CONFERENCES button 602, a conference list of the conference preparation unit is displayed to enable selecting a conference.

Figure 39C:
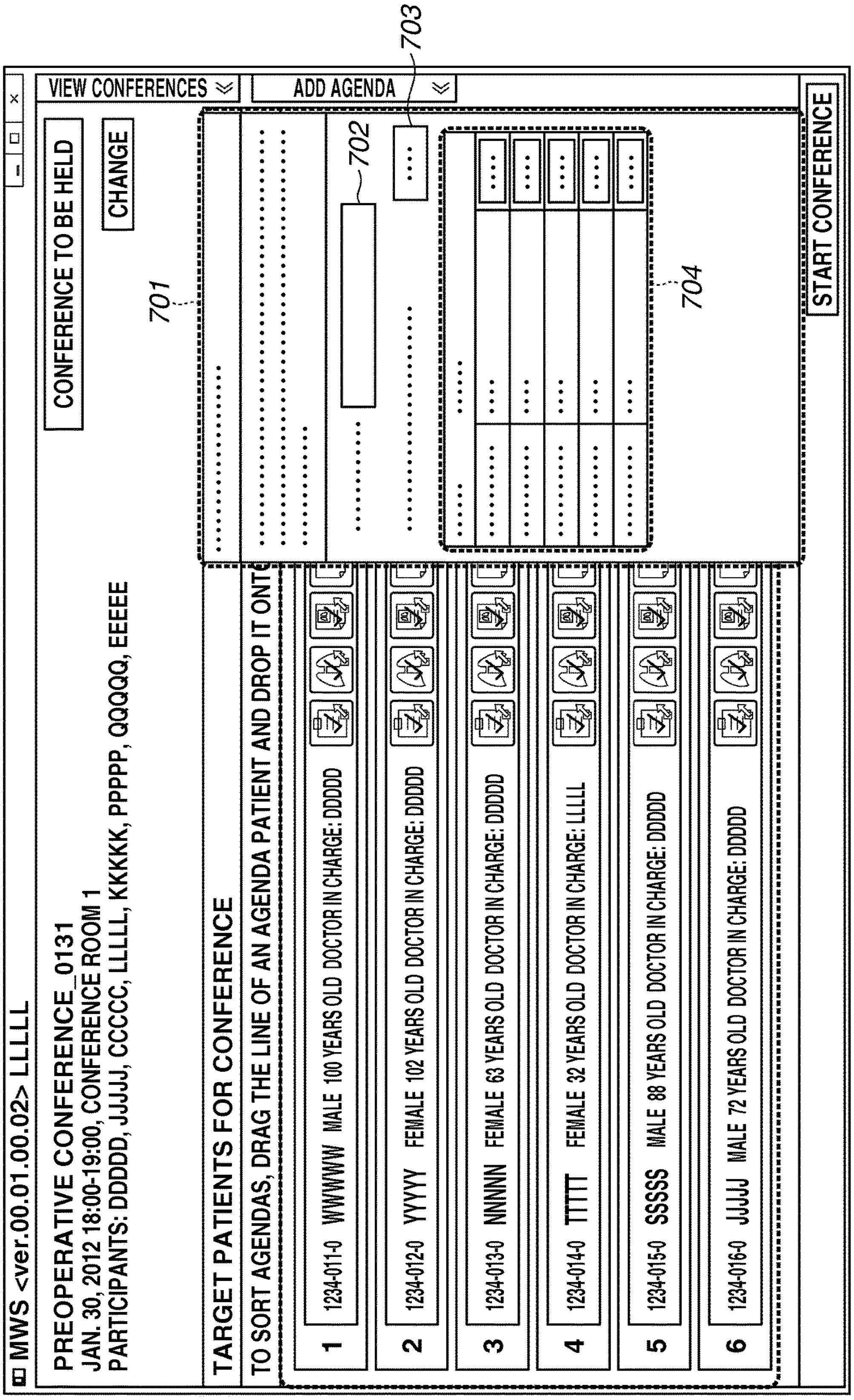
FIG. 39C illustrates a patient search operation on the conference client apparatus before starting a conference.

FIG. 39C illustrates a patient search operation on the conference client apparatus 1 before starting a conference. A patient selection panel 701 is used to select a patient. When the user presses the SELECT PATIENT button 504, the patient selection panel 701 is displayed from the right in a sliding way. The patient selection panel 701 enables searching for a desired patient and append the relevant patient to the agenda patient list display area 502. A patient ID and patient name input area 702 is used to specify a search condition when searching for a desired patient. The conference client apparatus 1 searches for a patient whose patient name and patient ID partially coincide with the character string input in this area. A check box below the patient ID and patient name input area 702 limits the search target to patients with whom materials have been prepared by the user. When the user presses a SEARCH button 703, patients satisfying the specified search condition are displayed in list form.

A search result list 704 displays here a list of patients satisfying the search condition. Each item in the search result list 704 is provided with an ADD button. Pressing the ADD button appends the relevant patient to the end of the agenda patient list display area 502. A patient in the search result list 704 can be appended to the agenda patient list display area 502 by dragging the relevant patient from the search result list 704 and dropping it at a target position in the agenda patient list display area 502.

Figure 39D:
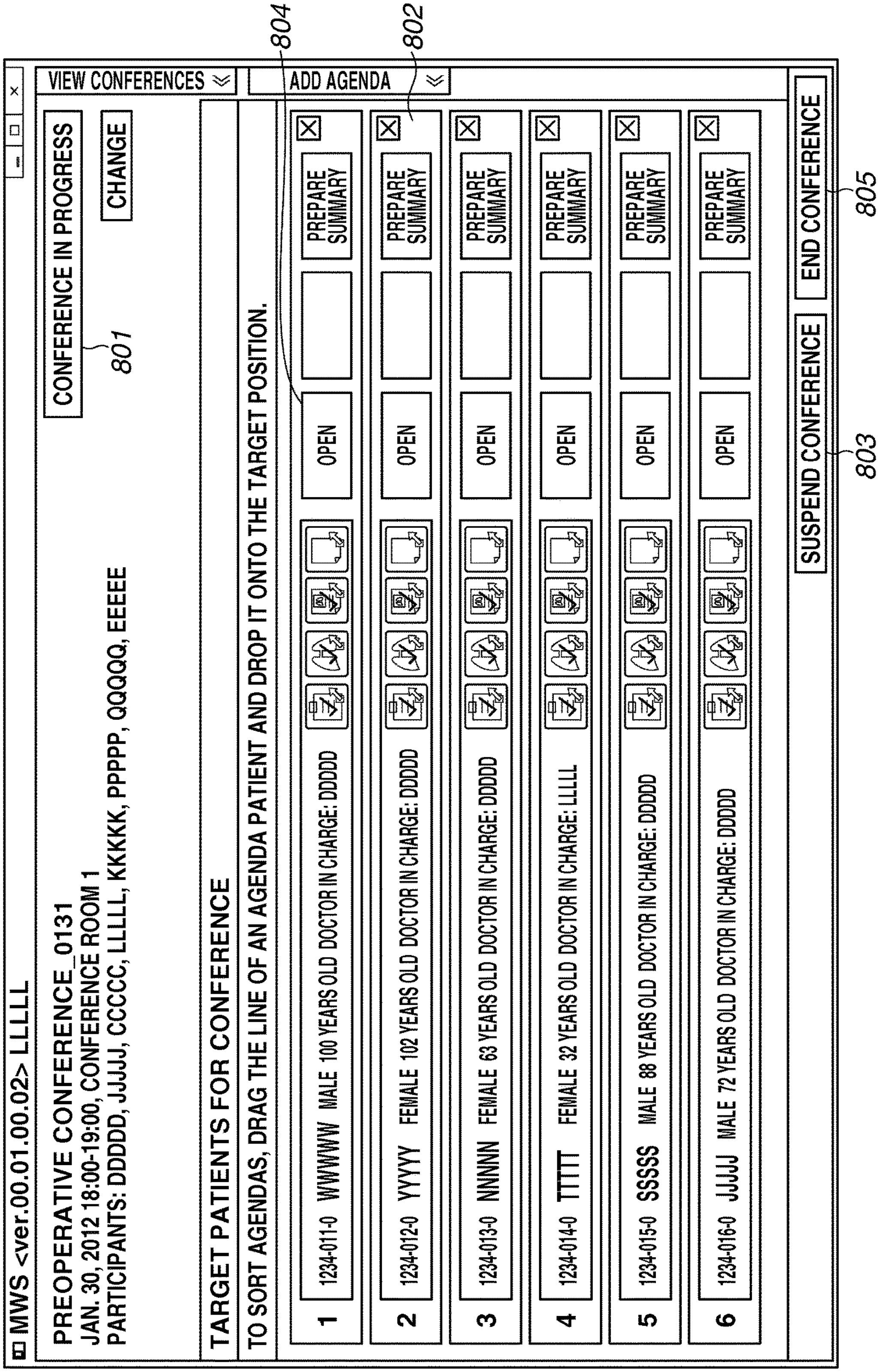
FIG. 39D illustrates a conference starting operation on the conference client apparatus.

FIG. 39D illustrates a conference starting operation on the conference client apparatus 1. When the user presses the START CONFERENCE button 505, a conference is started. A conference status 801 indicates the status of the relevant conference (CONFERENCE IN PROGRESS in this example). A selected patient 802 is a patient selected in the agenda patient list display area 502. Immediately after starting a conference, the first agenda patient is selected. The selected patient 802 is enclosed by a highlighted frame, and a relevant OPEN button 804 is highlighted. When the user presses a SUSPEND CONFERENCE button 803, the screen illustrated in FIG. 47B appears. When the user presses an END CONFERENCE button 805, the relevant conference ends.

FIG. 39E illustrates an operation for changing the order of agenda patients on the conference client apparatus 1. This operation changes the order of agenda patients (patients to be discussed in the conference) in the agenda patient list display area 502 by dragging the selected patient 802 and dropping it at a target position. A selected patient 901 is the selected patient 802 after the order is changed.

Figure 39F:
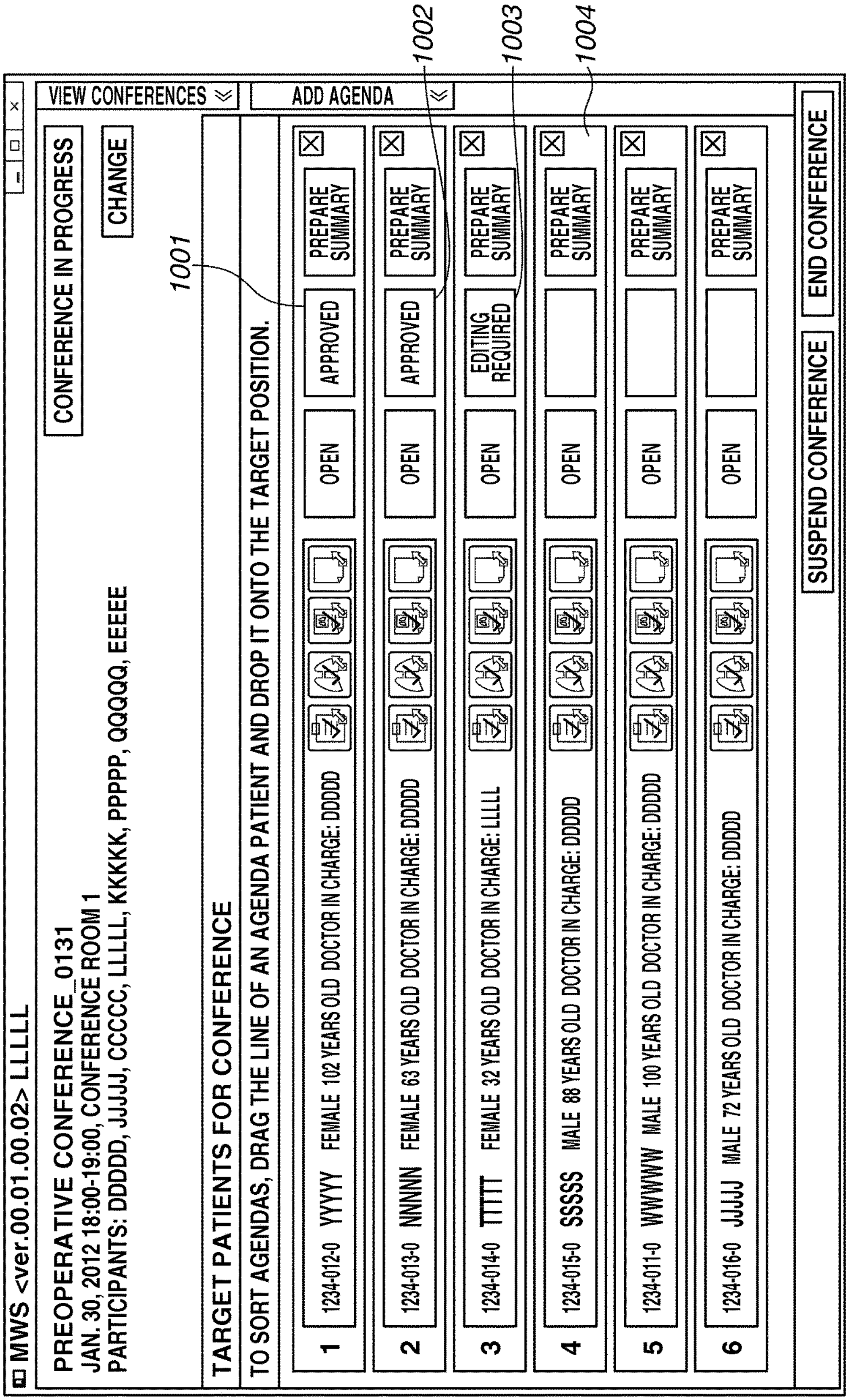
FIG. 39F illustrates a state before starting agenda No. 4 on the conference client apparatus.

FIG. 39F illustrates a state before starting agenda No. 4 on the conference client apparatus 1, i.e., a state where agenda Nos. 1 to 3 have been discussed in the conference. FIG. 39F illustrates conclusion statuses 1001, 1002, and 1003 of the agenda Nos. 1, 2, and 3 (APPROVED, APPROVED, and EDITING REQUIRED), respectively. Each of the conclusion statuses displays in easily viewable form the contents of the relevant agenda without opening it. A PREPARE SUMMARY button is provided (enabled) to the right of each conclusion status. For an unsolved agenda (with an empty conclusion status), the PREPARE SUMMARY button is disabled.

A patient 1004 is a patient to be discussed next. The patient 1004 is enclosed by a highlighted frame and the relevant OPEN button 804 is highlighted. When the user presses the OPEN button 804, the screen illustrated in FIG. 40A appears.

Figure 40A:
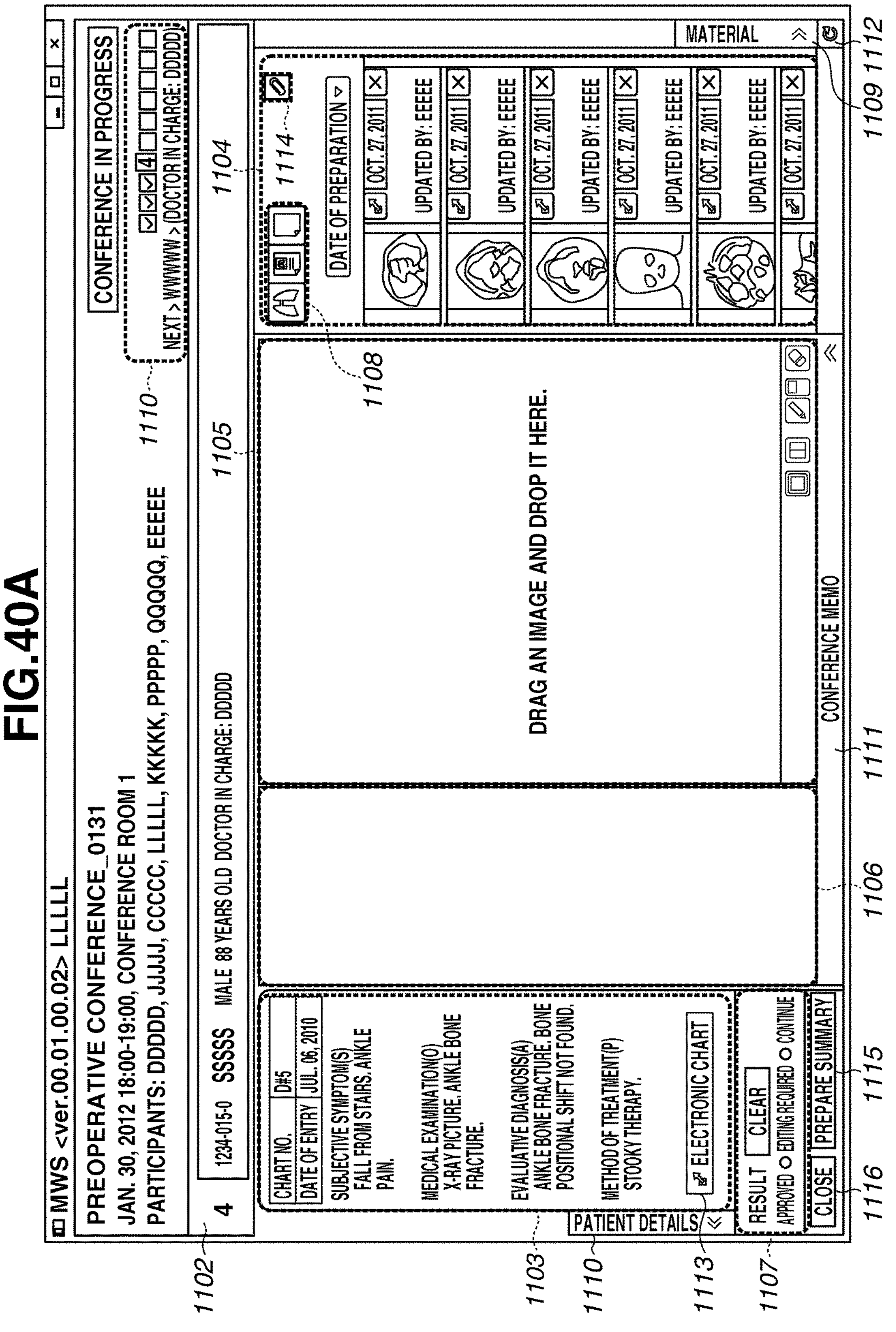
FIG. 40A illustrates a screen after starting agenda No. 4 on the conference client apparatus.

FIG. 40A illustrates a screen after starting agenda No. 4 on the conference client apparatus 1. When the user presses the OPEN button 804, detailed information of the relevant patient is displayed. Referring to the detailed information, the doctor in charge can sequentially confirm and describe the basic patient information, medical care information (diagnostic findings and the treatment plan of the chart information), and supporting examination information.

An agenda status indicator 1101 indicates the agenda status. The upper part of the agenda status indicator 1101 indicates the order of the relevant agenda in the conference. In the present exemplary embodiment, the relevant agenda is the fourth one out of 10 agendas of the conference. The first three agendas have been resolved and the remaining six are unresolved. The lower part of the agenda status indicator 1101 indicates the patient name and the name of the doctor in charge for the next agenda. Similar to the agenda patient list 502, basic patient information 1102 displays the patient ID, name, sex, and age of the patient, and the name of the doctor in charge. A medical care information display area 1103 displays SOAP information extracted from the electronic chart.

A conference material display area 1104 displays a list of conference materials prepared by the conference preparation unit of the conference client apparatus 1. The conference materials are listed for each type of information, i.e. examination image information, report information, and other information. Each material in the list is provided with a thumbnail image, the examination date, the name of person who prepared the material, and an external system call button. The external system call button enables activating an external system, such as the electronic chart system 151 and the PACS viewer 160, and referring to an original copy of the conference material.

A work area 1105 displays a conference material selected from the conference material display area 1104 with a drag-and-drop operation. Conference material display options are arranged at the bottom of the work area 1105, including a single material display change button, a 2-material comparative display change button, an annotation pen selection button, an annotation pen color change button, and an eraser button, from left to right. (These options will be described below with reference to FIGS. 43A, 43B, and 43C).

A summary material display area 1106 displays thumbnails of conference materials to be reflected to a summary. Conference materials in this area are retained with the annotation, and transferred to the summary generation unit. A conclusion input area 1107 is used to input a conclusion of discussions between doctors regarding findings and treatment method for the relevant patient, and supporting examination information. In the present exemplary embodiment, APPROVED, EDITING REQUIRED, or CONTINUE can be selected.

Figure 44E:
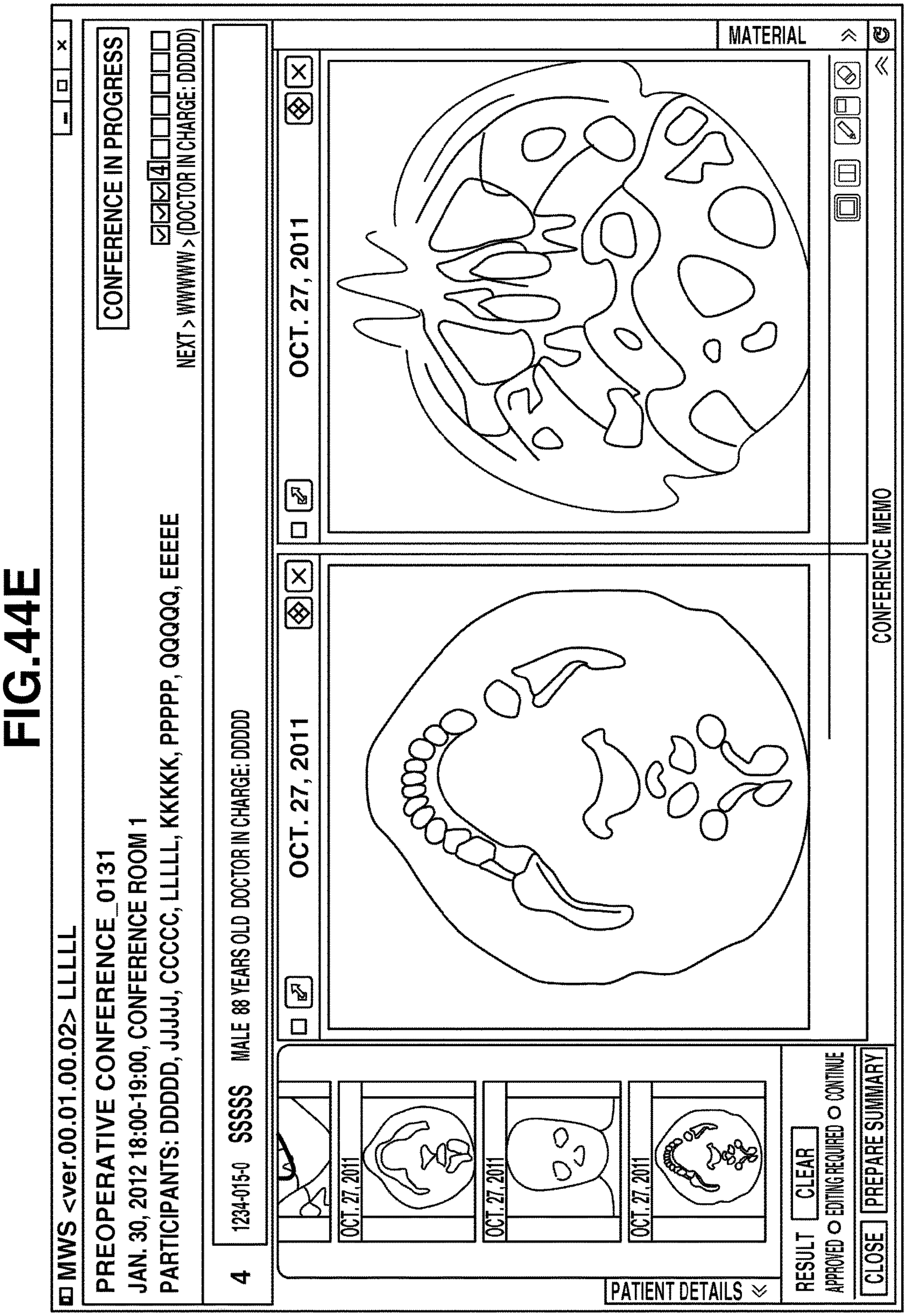
FIG. 44E illustrates a state where a material list is hidden in the 2-division material screen on the conference client apparatus.

Material change buttons 1108 are used to select a type of materials to be displayed in the conference material display area 1104, out of examination image information, report information, and other information. A conference material display toggle button 1109 shows or hides the conference material display area 1104 (FIG. 44E). A medical care information display toggle button 1110 shows or hides the medical care information display area 1103 (FIG. 44B). A conference memo display toggle button 1111 shows or hides a conference memo input area for the relevant patient. An update reflection button 1112 reflects information changed by an operation other than screen display (for example, aback ground job).

An electronic chart system activation button 1113 arranged in the medical care information display area 1103 activates the electronic chart system 151 to refer to the original information of the relevant patient on the electronic chart system 151. A material appending button 1114 arranged in the conference material display area 1104 activates a file selection dialog for appending a insufficient material. A PREPARE SUMMARY button 1115 calls the conference summary output unit to generate a summary for discussions about the relevant patient. A CLOSE button 1116 closes detailed information of the relevant agenda patient, and displays the agenda list described above with reference to FIG. 39A.

Figure 40B:
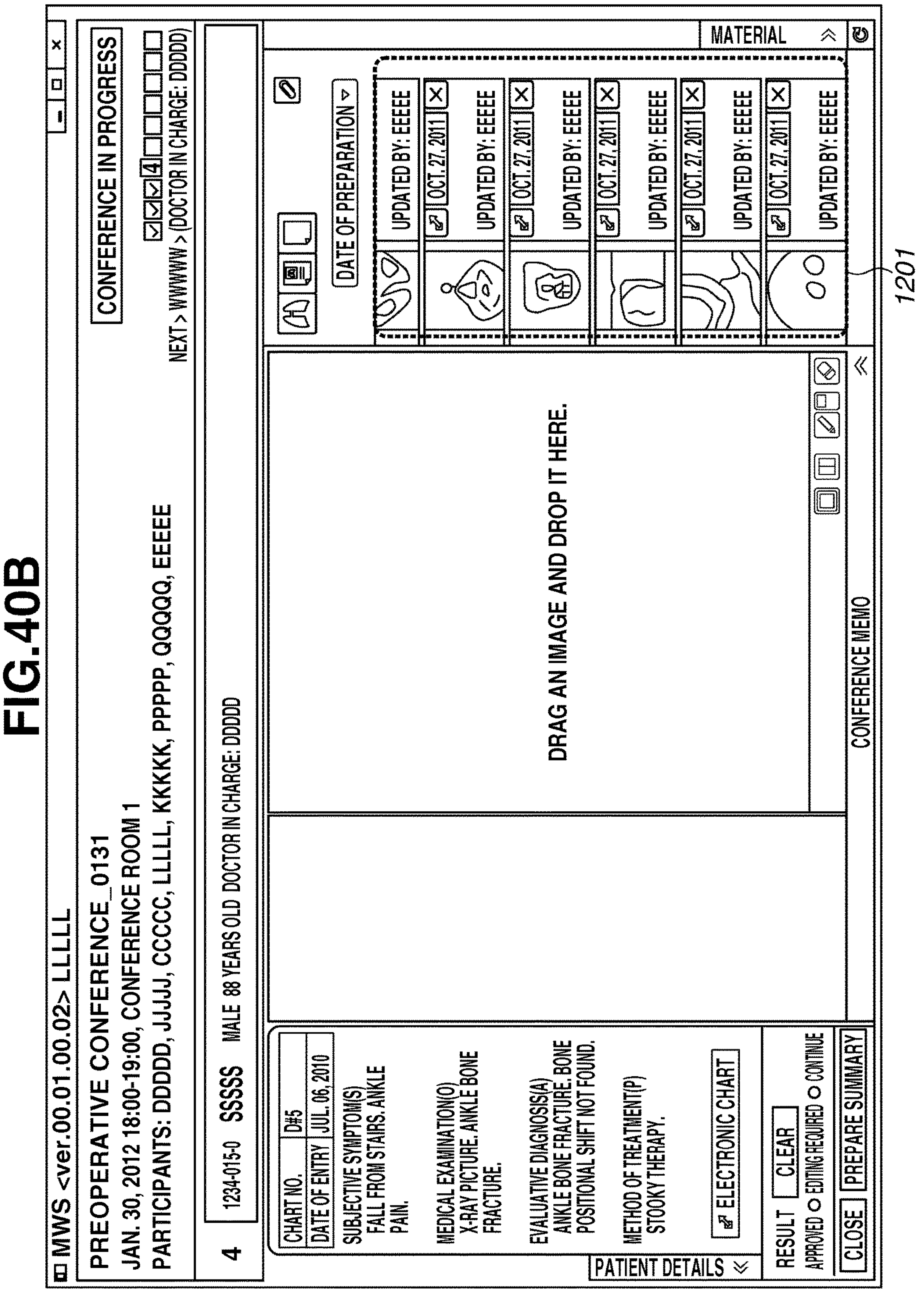
FIG. 40B illustrates scrolling of a material list (examination image tab) on the conference client apparatus.

FIG. 40B illustrates scrolling of a material list (examination image tab) on the conference client apparatus 1. Performing a dragging operation in the vertical direction in a conference material display area 1201 vertically scrolls list items. Further, performing a flick operation in the vertical direction inertia-scrolls list items in the vertical direction.

Figure 41A:
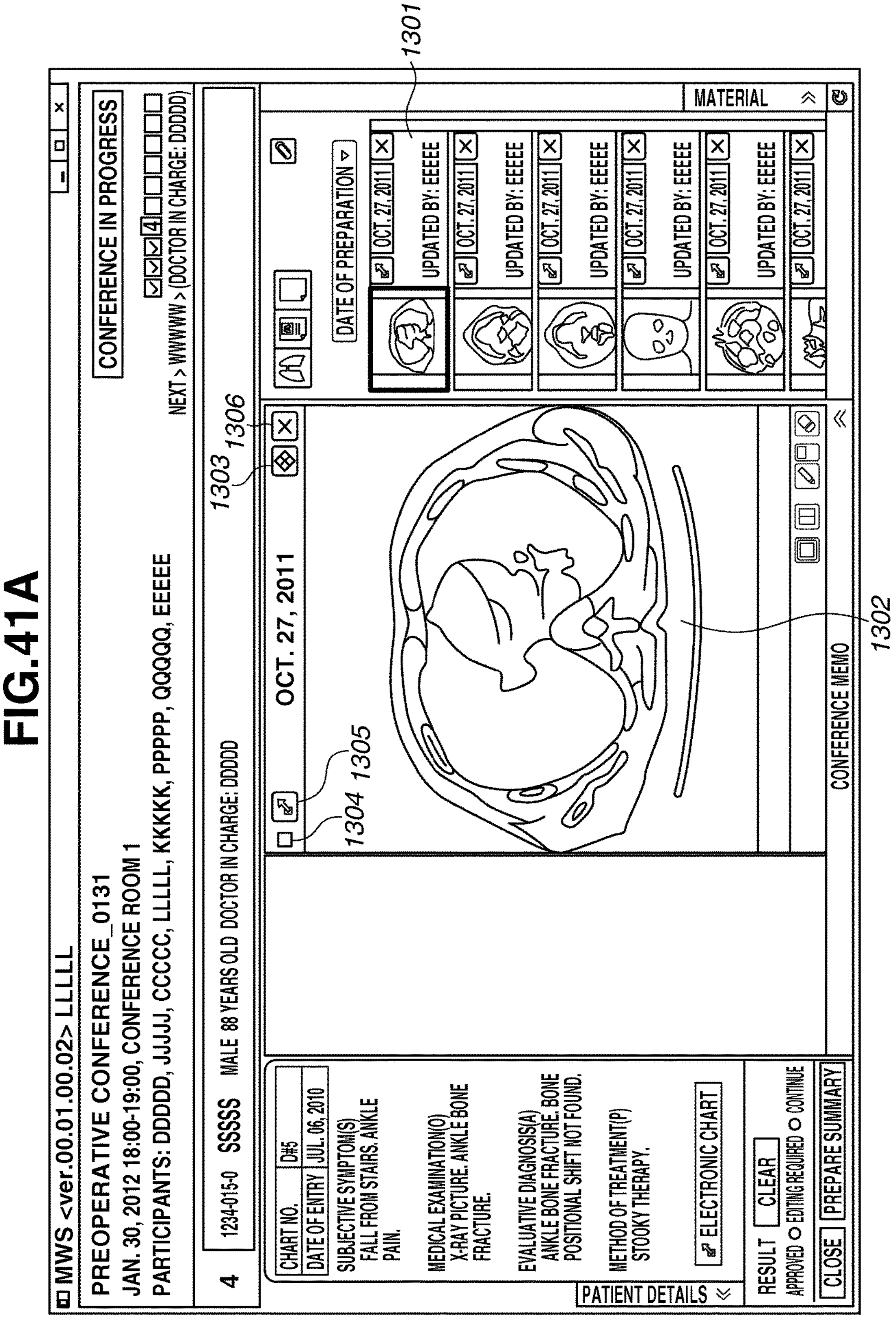
FIG. 41A illustrates a workspace for a selected material on the conference client apparatus.

FIG. 41A illustrates a workspace for a selected material on the conference client apparatus 1. A selected material 1301 is a material selected in the conference material display area 1201. A thumbnail of the selected material 1301 is enclosed by a highlighted frame. A selected material 1302 is displayed in the workspace. Processing for displaying the selected material 1301 in the workspace will be described below with reference to FIG. 41B. The workspace displays a reference image (having a larger amount of information than the thumbnail) of the selected material 1301. An all-annotations erase button 1303 erases all of annotations supplied to the relevant material while an eraser button at the bottom of the work area 1105 erases only a selected annotation.

A summary storage check box 1304 specifies whether the relevant material is to be reflected to a summary. When this check box is set, the relevant material is displayed in the summary material display area 1106 when the material is closed. An external reference button 1305 activates an external system (the electronic chart system 151, the PACS viewer 160, etc.) to refer to an original copy of the relevant material, A close button 1306 closes the material displayed in the workspace and erases it from the work area 1105.

Figure 41B:
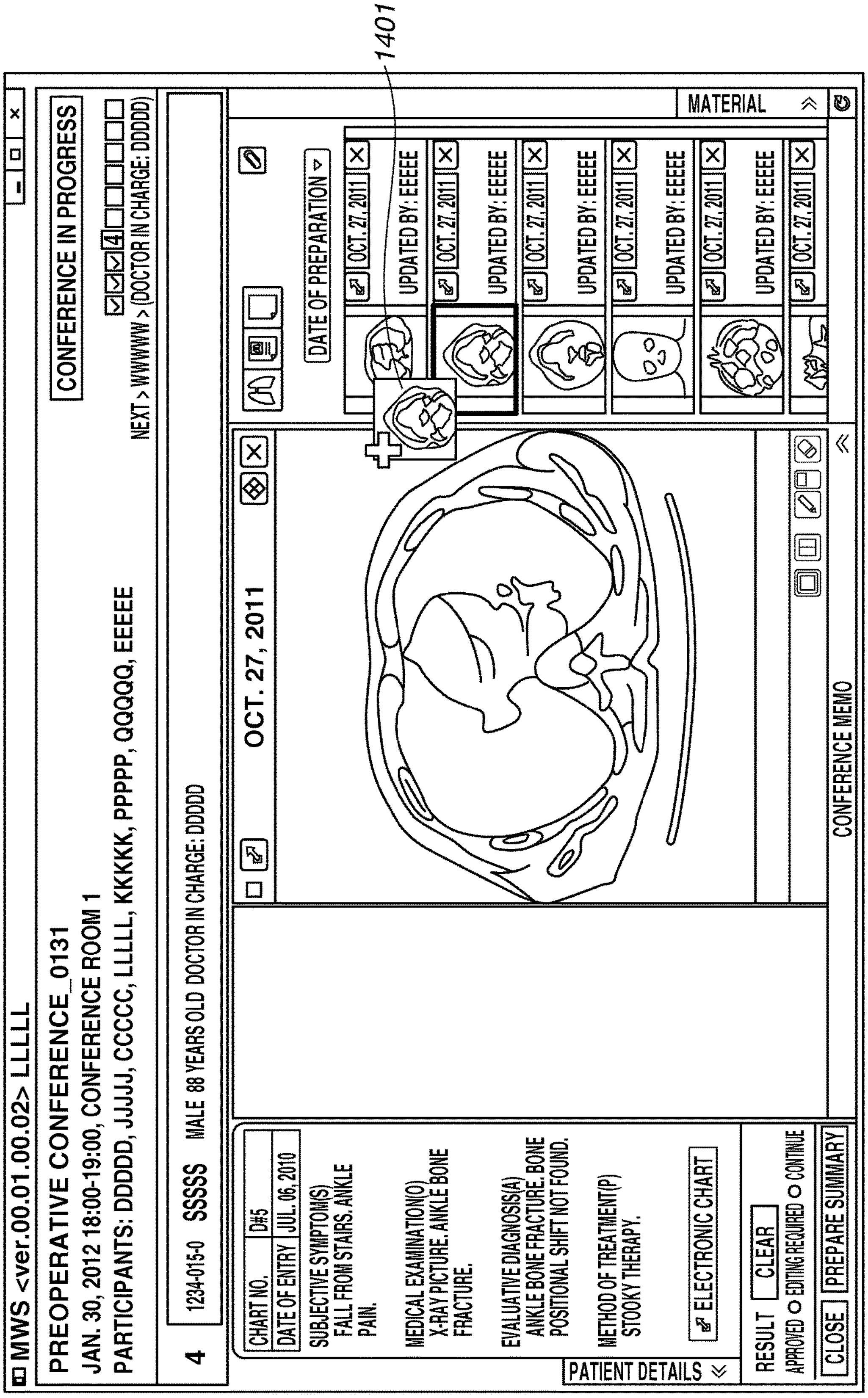
FIG. 41B illustrates a drag-and-drop operation from the material list on the conference client apparatus.

FIG. 41B illustrates a drag-and-drop operation from the material list on the conference client apparatus 1. An operation thumbnail 1401 of a material selected in the conference material display area 1201 is used to operate the material. Dragging the selected material and dropping it into the workspace displays the material in the workspace. The operation thumbnail 1401 is a semi-transparent thumbnail image with a "+" (positive mark) icon superimposed thereon indicating that the relevant material is currently being operated.

Figure 42A:
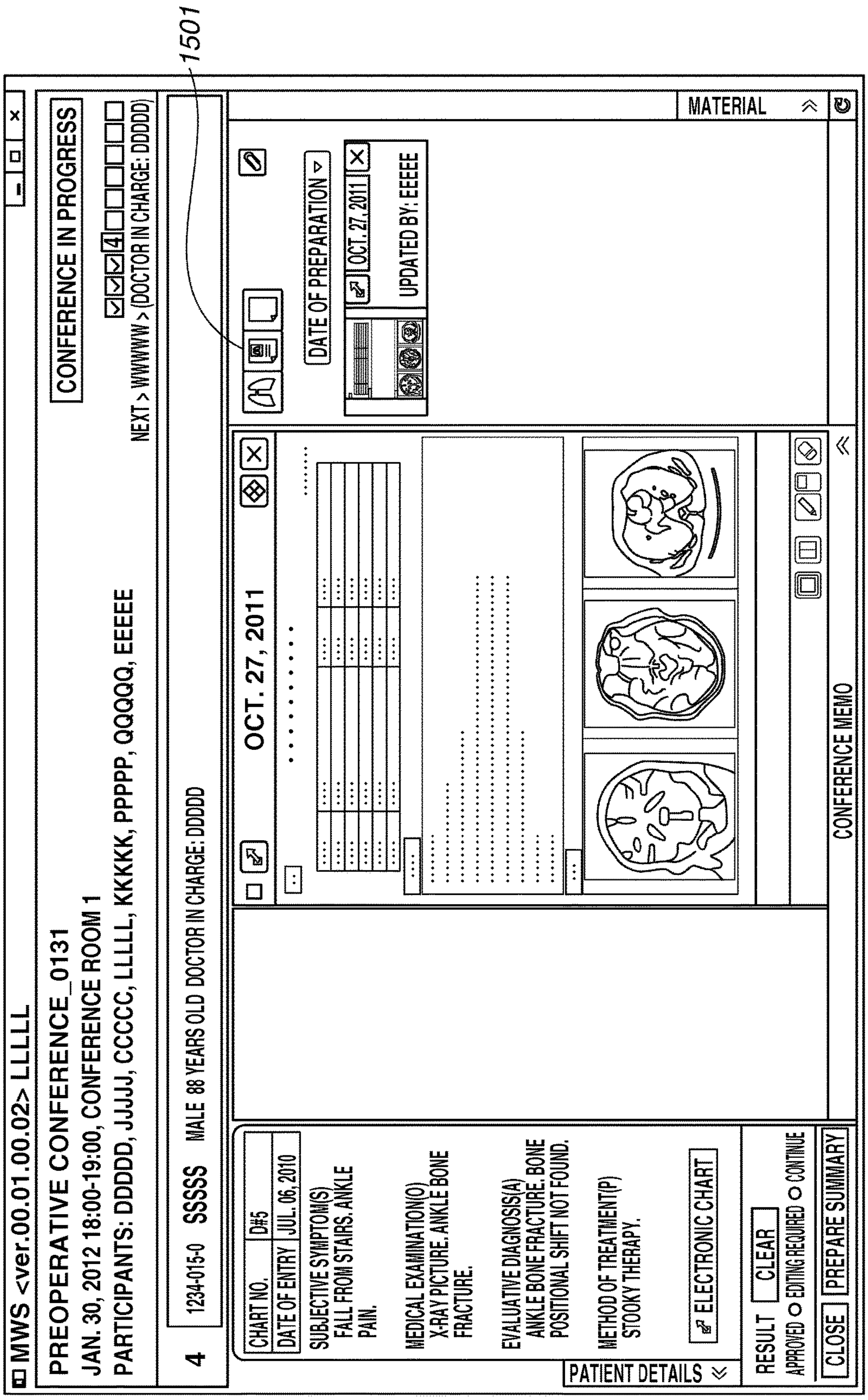
FIG. 42A illustrates a material list on the conference client apparatus.

FIG. 42A illustrates a material list (report tab) on the conference client apparatus 1. The material change buttons 1108 include a report tab 1501. When the user presses the report tab 1501, a list of materials classified as a report (examination report) out of materials prepared as a conference material is displayed in the conference material display area 1201. The conference preparation system according to the present exemplary embodiment handles reports in a similar way to examination images. A material in the conference material display area 1201 can be displayed in the workspace through a drag-and-drop operation.

Figure 42B:
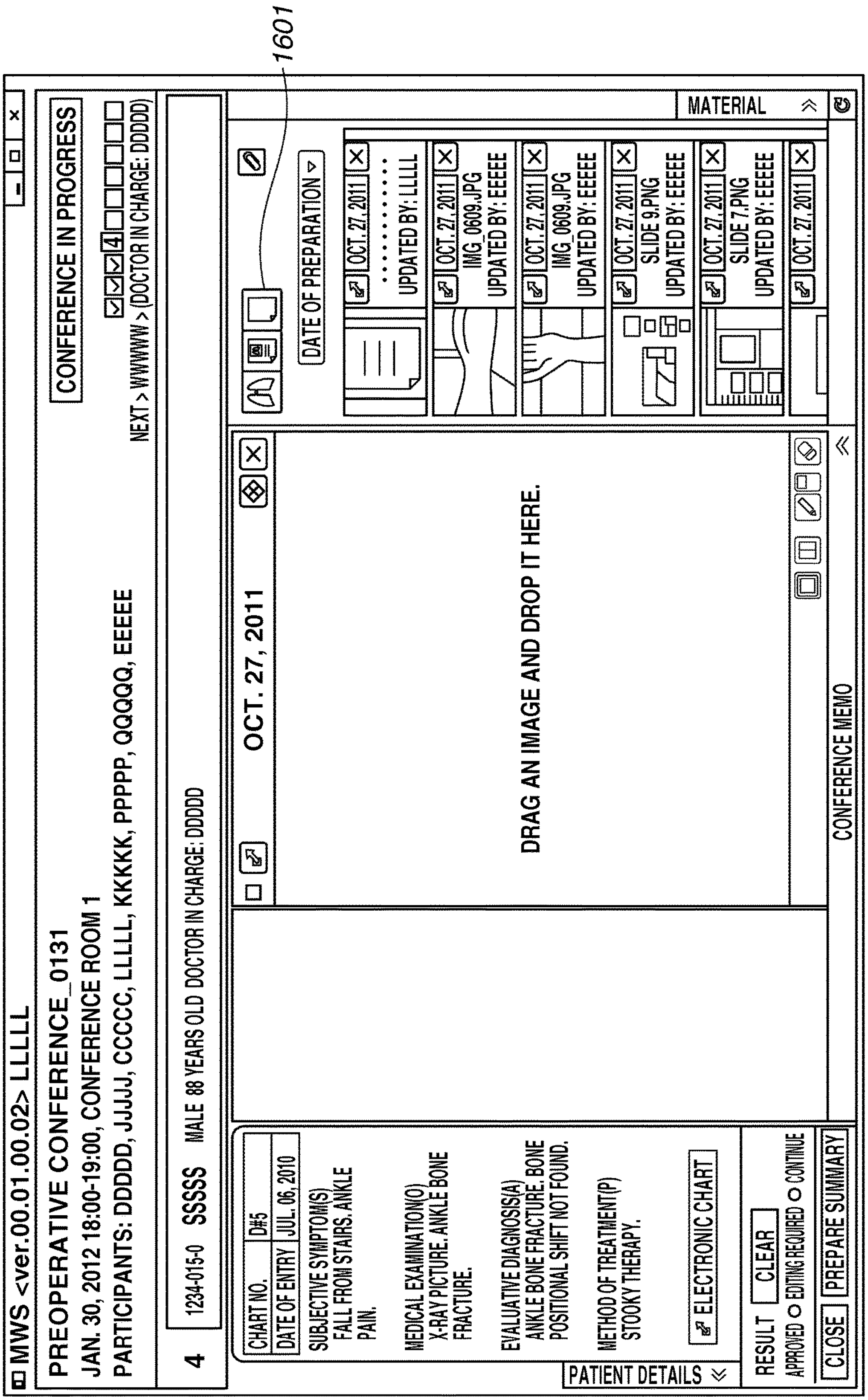
FIG. 42B illustrates a material list on the conference client apparatus.

FIG. 42B illustrates a material list (non-DICOM image tab) on the conference client apparatus 1. The material change buttons 1108 includes a non-DICOM image tab 1601. When the user presses the non-DICOM image tab 1601, a list of non-DICOM images (camera and PC images) and materials classified as a document (text or other office document) out of materials prepared as conference materials is displayed in the conference material display area 1201. The conference preparation system according to the present exemplary embodiment handles non-DICOM images and documents in a similar way to examination images. A material in the conference material display area 1201 is also displayed in the workspace through a drag-and-drop operation.

FIG. 43A illustrates annotation and automatic summary setting for a material on the conference client apparatus 1. An annotation setting button 1701 is used to switch between the annotation input mode and the pointing mode of the workspace. An example of an annotation input 1702 is a stroke input by using a mouse or touch device is superimposed onto the examination image data. When a summary storage check box 1703 is set, the relevant material is stored in the summary material display area 1106 to prepare a summary. For an annotated material, the summary storage check box 1703 is automatically set to reduce user's burden. If the user explicitly clears the automatically set summary storage check box 1703, the relevant material, even if it is annotated, is not stored in the summary material display area 1106. An eraser button 1704 erases a specified annotated portion. An all-annotations erase button 1705 erases all of annotation information.

FIG. 43B illustrates annotation color selection on the conference client apparatus 1.

A color selection button 1801 specifies an annotation input color. When the user presses the color selection button 1801, a color selection panel 1802 appears to enable the user to set an annotation input color. As a result, annotations can be input in different colors allowing the user to express the process of discussions in the conference in an easily viewable way (FIG. 43C).

FIG. 43D illustrates scale display for an agenda material on the conference client apparatus 1. A conference material 2001 is the vicinity of the annotation area of the conference material illustrated in FIG. 43C, enlarged through a user operation in the workspace. In the specified area, the conference material is reduced or enlarged upon detection of a pinch-in or pinch-out operation (with two fingers) or a mouse wheel operation by the user. Although not illustrated, a user operation (dragging operation) in the specified area in the workspace moves the viewing area.

FIG. 44A illustrates materials set for summary on the conference client apparatus 1.

Conference materials 2101, 2102, and 2103 are conference materials to be reflected to a summary held in the summary material display area 1106, displayed in list form. This list of materials annotated and materials explicitly specified for summary during the conference visualizes the conference progress status. Results of operations performed in the workspace during the conference, such as annotation input, enlargement/reduction, and viewing area movement, are displayed as thumbnails. Similar to thumbnails, the summary reflects results of operations performed during the conference.

FIG. 44B illustrates a state where the medical care information display area 1103 is hidden on the conference client apparatus 1, i.e., a screen in which the medical care information display area 1103 is hidden by operating the medical care information display toggle button 1110. In this case, the summary material display area 1106 is horizontally moved to the left to expand the workspace. This enables displaying the conference material in a larger space for discussion, making it easier to view the conference.

FIG. 44C illustrates a 2-division material screen on the conference client apparatus 1. A 2-division screen button 2301 divides the workspace area into two division spaces. In each of the division spaces of the workspace, a conference material is displayed and an annotation input and enlargement/reduction are possible (FIG. 44D), thus facilitating comparison of materials. A 1-screen button merges the two division screens into one. In the present exemplary embodiment, the right screen is erased and the left screen is not.

FIG. 44E illustrates a state where a material list is hidden in the 2-division material screen on the conference client apparatus 1, i.e., a screen in which the conference material display area 1104 is hidden by operating the conference material display toggle button 1109. In this case, the workspace is enlarged. This enables displaying a conference material in a larger space for discussion, making it easier to view the conference. Referring to FIG. 44E, although the medical care information display area 1103 is also hidden, the conference material display toggle button 1109 and the medical care information display toggle button 1110 can operate independently from each other. Specifically, it is also possible to hide only the conference material display area 1104 and display the medical care information display area 1103.

Figure 45:
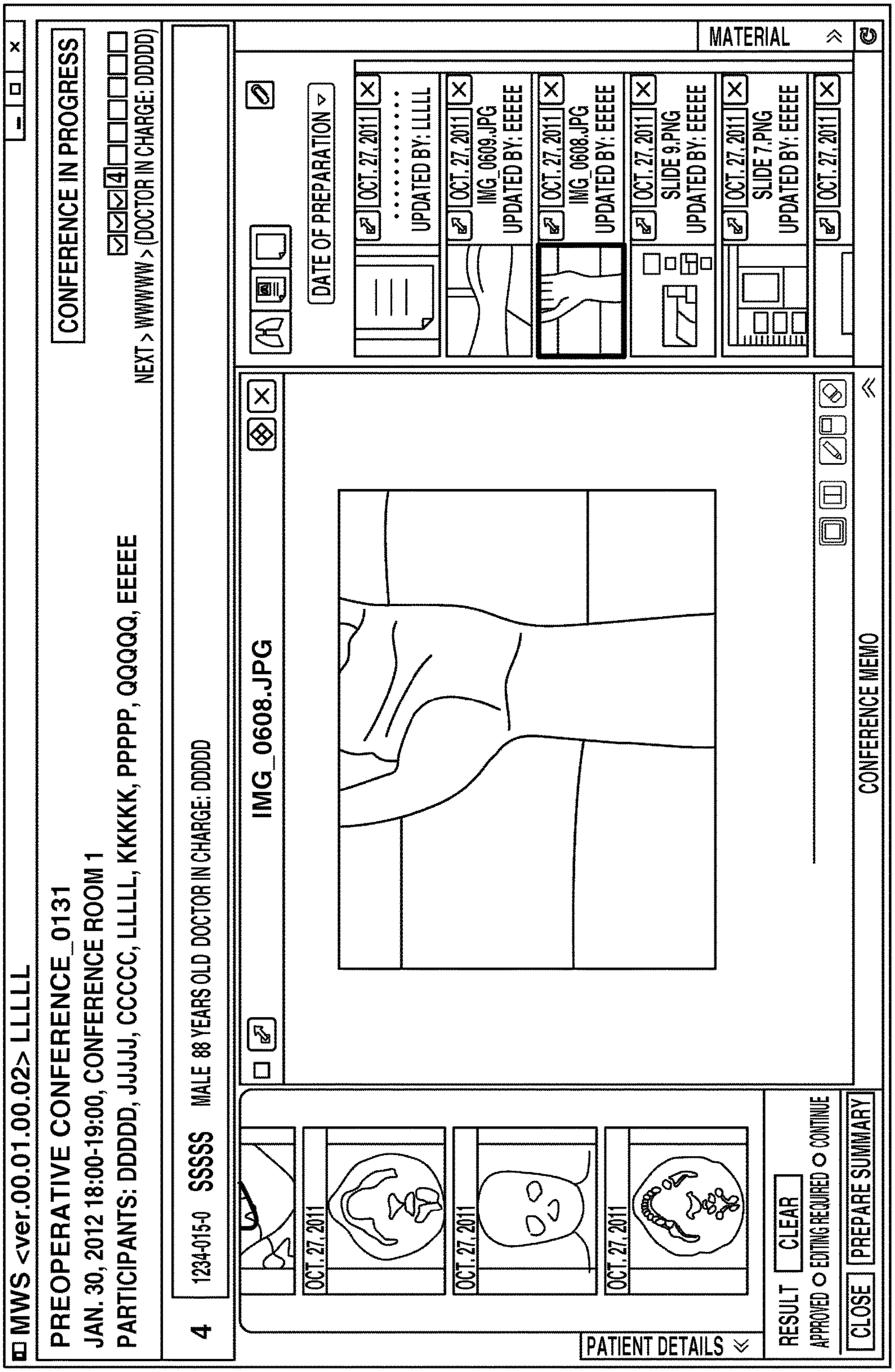
FIG. 45 illustrates non-DICOM image display on the conference client apparatus according to the third exemplary embodiment.

FIG. 45 illustrates non-DICOM image display on the conference client apparatus 1. Also when advancing discussions using a non-DICOM image, similar to the above-described operations for the examination image, the conference client apparatus 1 performs annotation input, enlargement/reduction, viewing area movement, and screen division (material comparison) by dragging the non-DICOM image and dropping it into the workspace.

Figure 46A:
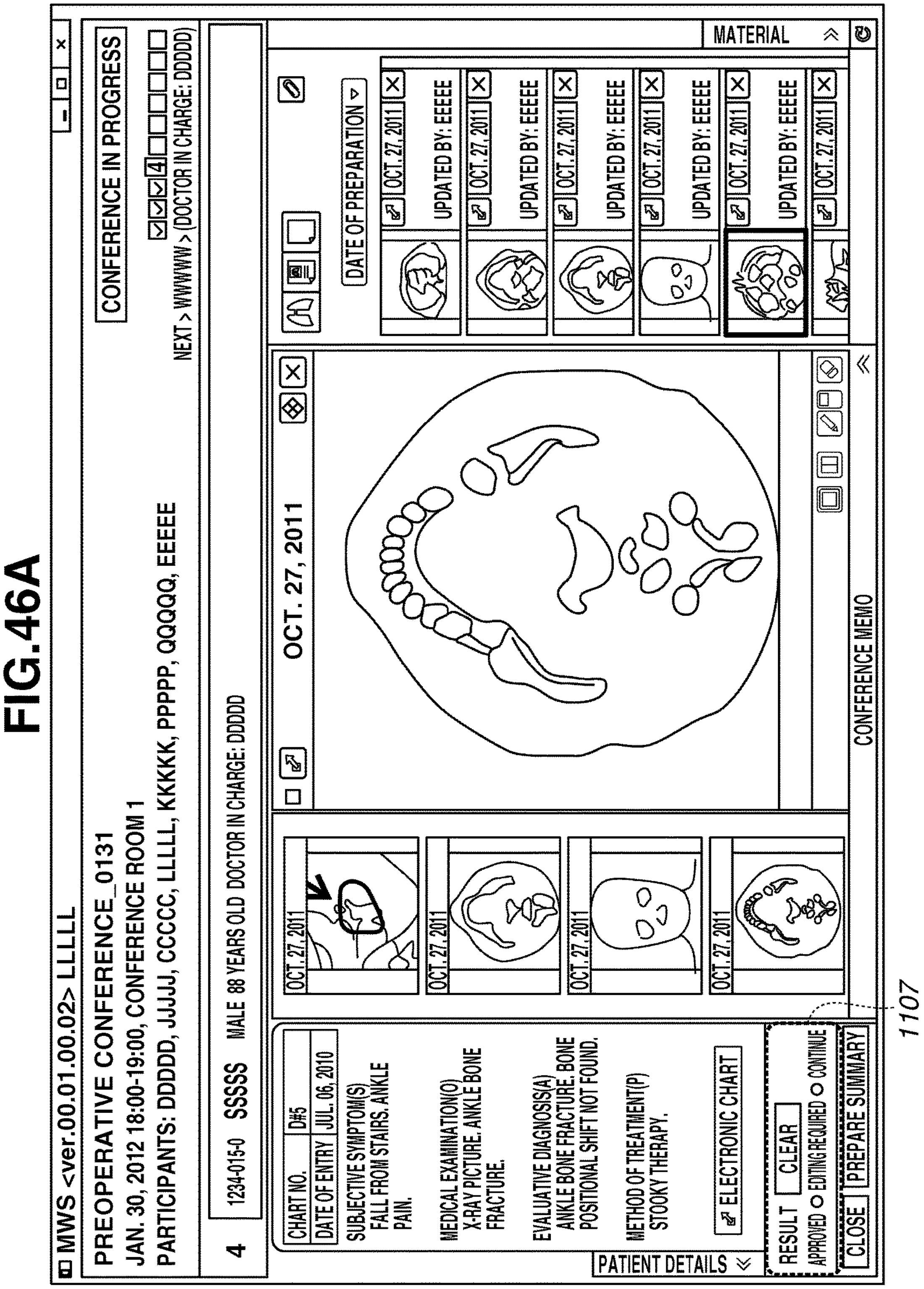
FIG. 46A illustrates a simplified conclusion input operation on the conference client apparatus.
Figure 46B:
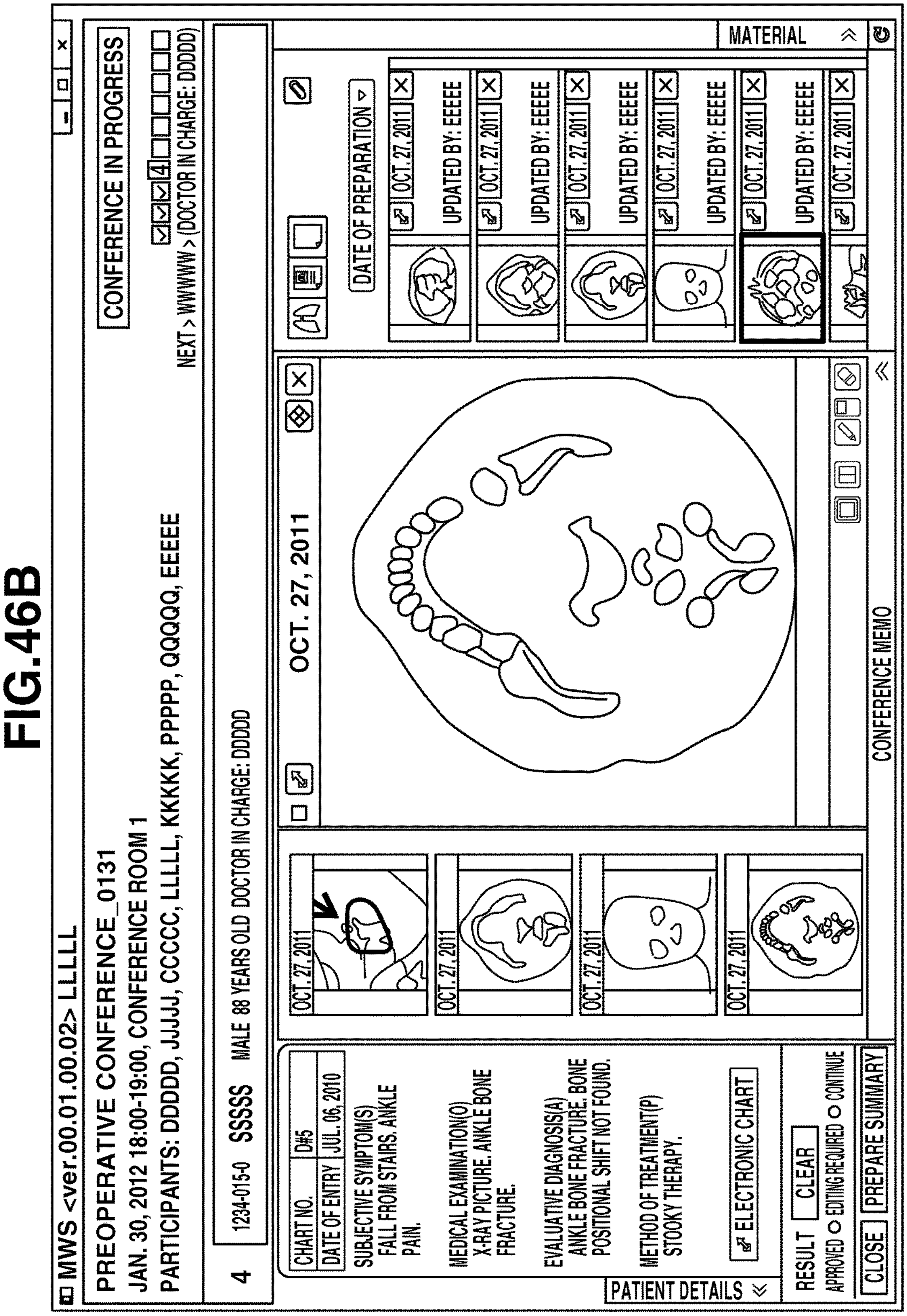
FIG. 46B illustrates a state where a simplified conclusion input operation has been made on the conference client apparatus.

FIG. 46A illustrates a simplified conclusion input operation on the conference client apparatus 1. As described above, the user inputs a conclusion of discussions between doctors regarding findings and treatment method for the relevant patient, and supporting examination information, by using the conclusion input area 1107. The user simply selects "APPROVED" to approve the conclusion (FIG. 46B), "EDITING REQUIRED" to specify the necessity of separately appending a comment, or "CONTINUE" to continue discussions. The conference summary output unit reflects the input conclusion to the summary.

Figure 46C:
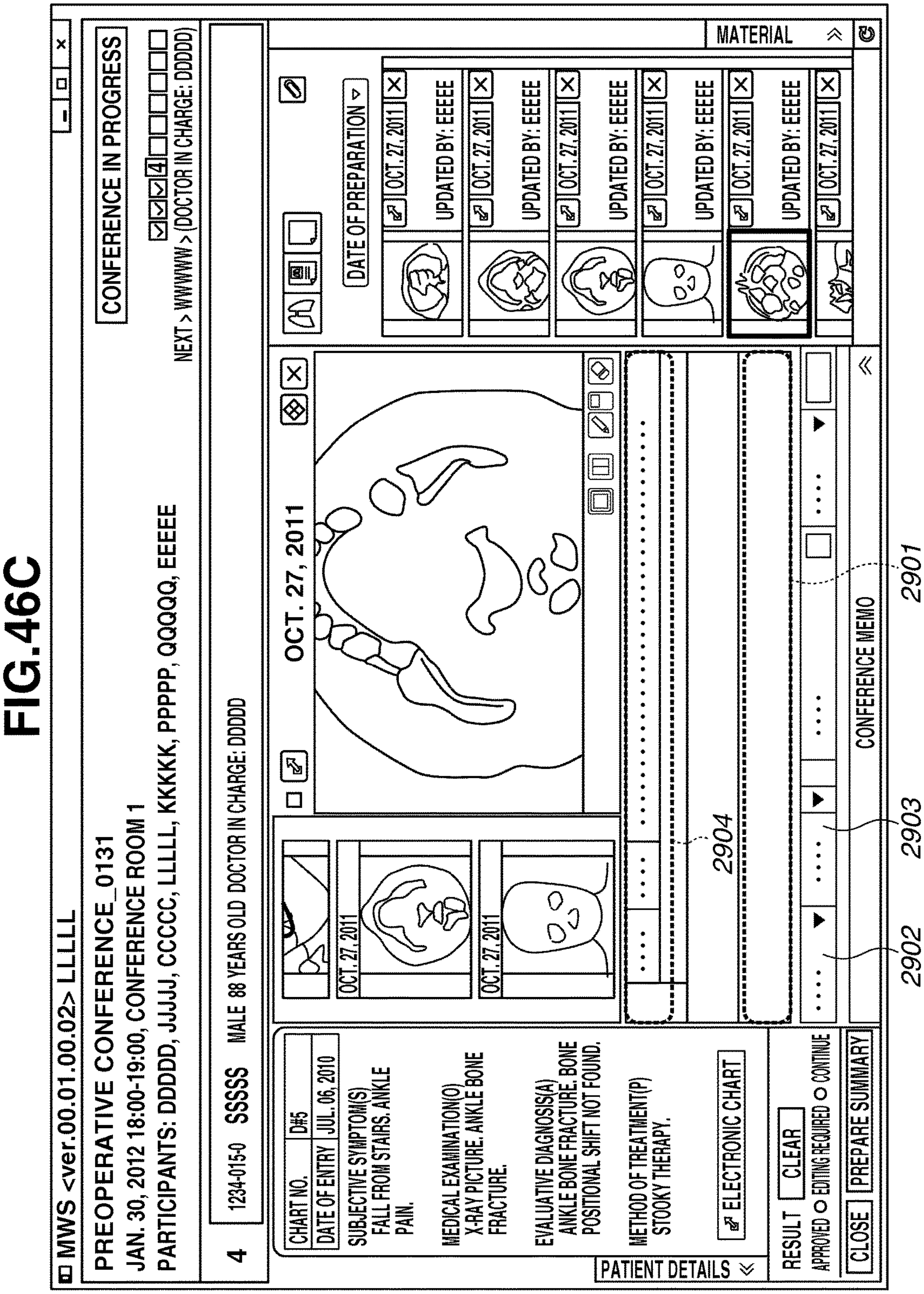
FIG. 46C illustrates a comment appending operation on the conference client apparatus.

FIG. 46C illustrates a comment appending operation on the conference client apparatus 1. The conference memo display toggle button 1111 shows or hides a conference memo input area 2901 for the relevant patient. Text information can be input to the conference memo input area 2901. An statement type selection box 2902 allows the user to simply specify a type of statement (question, reply, action item, comment, or conclusion). A speaker selection box 2903 allows the user to simply specify a speaker out of the participants of the conference. A conference memo area 2904 displays a list of input statements. Statement memos recorded in the conference memo area 2904 are transferred to the summary generation unit together with materials referred to during the conference retained in the summary material display area 1106.

Figure 47A:
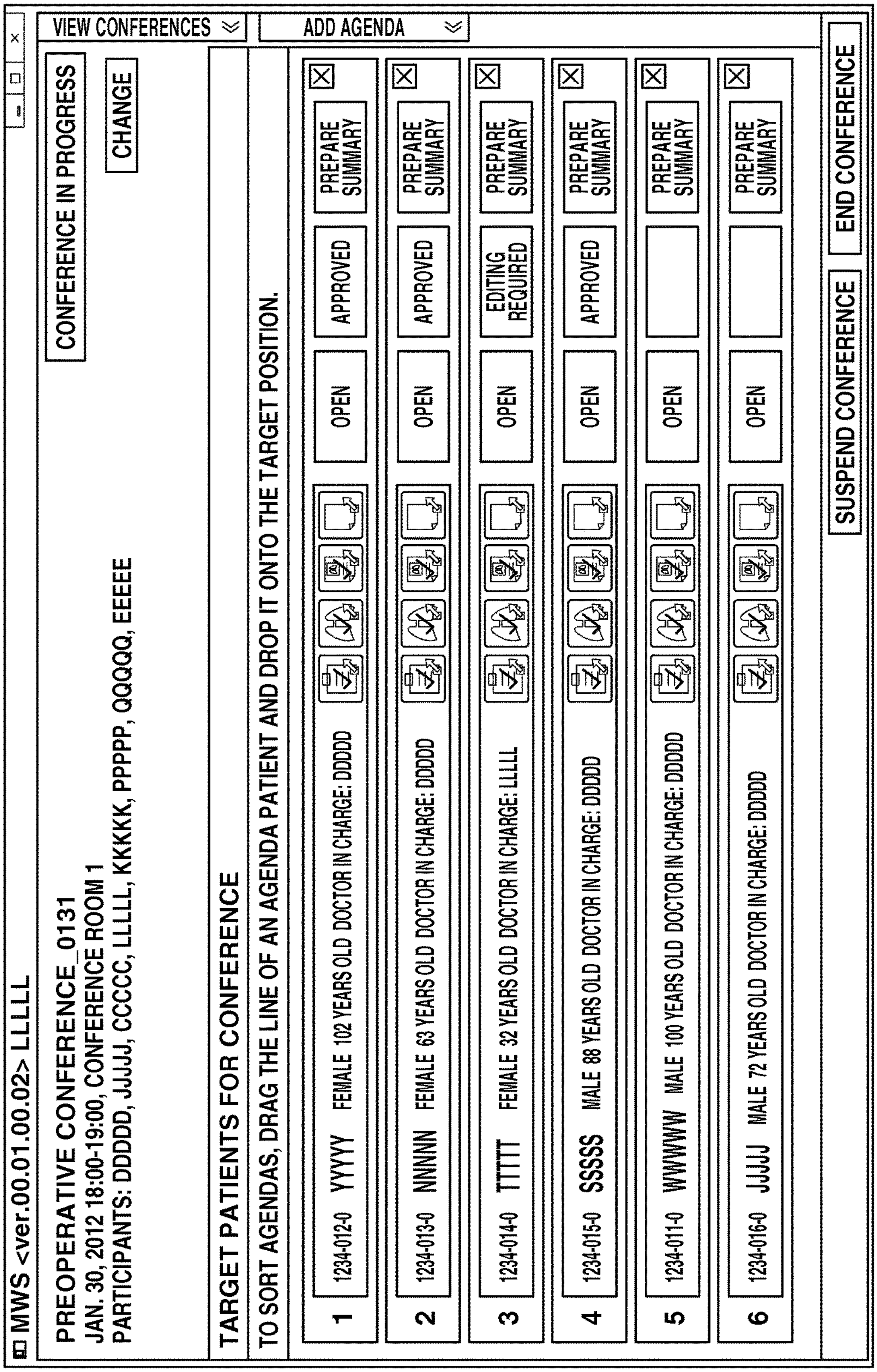
FIG. 47A illustrates a state where an agenda is completed and the next agenda is highlighted on the conference client apparatus.

FIG. 47A illustrates a state where an agenda is completed and the next agenda is highlighted on the conference client apparatus 1. After discussions using the above-described screen of agenda No. 4, the user inputs a conclusion from the conclusion input area 1107 and then presses the CLOSE button 1116. As a result, the conference client apparatus 1 returns from each individual agenda screen to the agenda patient list, as illustrated in FIG. 47A. In this case, the conference client apparatus 1 determines that discussions about agenda No. 4 are completed, and automatically selects agenda No. 5 as the next agenda. To prompt to start agenda No. 5, the conference client apparatus 1 highlights the relevant agenda and focuses the OPEN button 804.

FIG. 47B illustrates a state where a conference is suspended on the conference client apparatus 1. When the agenda patient list is displayed, pressing the SUSPEND CONFERENCE button 803 changes the status of the relevant conference to CONFERENCE SUSPENDED, as illustrated in FIG. 47B. A RESUME CONFERENCE button 3101 is displayed when the status of the relevant conference changes to CONFERENCE SUSPENDED. Pressing the RESUME CONFERENCE button 3101 resumes the conference (FIG. 47C).

The above-described configuration enables the medical conference support system according to the present invention to advance the conference in cooperation with the electronic chart system 151, the medical image management system, the examination reporting system, the image management system, and the file server 3 in the hospital. In particular, the present exemplary embodiment is characterized in material preparation status display, conclusion status display, conference progress status display, external system reference, non-DICOM image reference, summary material logging, and simplified conclusion input.

Although, in the present exemplary embodiment, enlargement/reduction and viewing area movement operations for the 2-division workspace are independently processed, the processing in the workspace is not limited thereto. For example, it can be easily assumed that enlargement/reduction and viewing area movement operations for one screen of the 2-division workspace are performed in cooperation with the other screen thereof.

Although, in the present exemplary embodiment, after completion of discussions by using the agenda patient details screen of one agenda patient, the processing once returns to the patient list and then the next agenda patient is selected, the screen transition is not limited thereto. For example, it can be easily assumed that the agenda patient details screen of a certain agenda patient changes directly to the agenda patient details screen of the next agenda patient.

Although, in the present exemplary embodiment, filter and sort functions are not described for the material list in the agenda patient details screen, it can be easily assumed that the material list is filtered or sorted.

Aspects of the present invention can also be realized by a computer of a system or apparatus (or devices such as a CPU or MPU) that reads out and executes a program recorded on a memory device to perform the functions of the above-described embodiment (s), and by a method, the steps of which are performed by a computer of a system or apparatus by, for example, reading out and executing a program recorded on a memory device to perform the functions of the above-described embodiment (s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Applications No. 2012-050685 filed Mar. 7, 2012, No. 2012-050686 filed Mar. 7, 2012, and No. 2012-050687 filed Mar. 7, 2012, which are hereby incorporated by reference herein in their entirety.

What is claimed is:

1. A conference preparation system comprising:

one or more processors; and one or more computer readable media coupled to the one or more processors, the one or more computer-readable media storing instructions that, when executed by the one or more processors, cause the one or more processors to perform operations comprising:

obtaining a window handle of a window displayed in a display screen;

determining, based on the obtained window handle, whether an application regarding the displayed window is a predetermined application or not;

acquiring a patient ID in a case where the application regarding the displayed window is the predetermined application;

determining whether a GUI (Graphical User Interface) component regarding the displayed window is a predetermined GUI component or not;

acquiring an area including the patient ID in the displayed window as an image in a case where the GUI component is not the predetermined GUI component;

acquiring character code strings as the patient ID by performing a character recognition on the image in a case where the GUI component is not the predetermined GUI component, acquiring the patient ID without performing the character recognition on the image in a case where the GUI component is the predetermined GUI component; and acquiring material information for the conference from a server based on the acquired patient ID.

2. The conference preparation system according to claim 1, wherein, in a case where the material information has been acquired, the acquired material information is displayed on the display screen at a size smaller than a size of the material information that has been previously displayed on the display screen.

3. The conference preparation system according to claim 2, wherein a button for canceling acquisition of the material information is displayed on the display screen with the material information being displayed at a size smaller than the size of the material information that has been previously displayed on the display screen.

4. The conference preparation system according to claim 1, wherein the patient ID is associated with a conference item based on patient information about an order acquired from an ordering system.

5. A computer-implemented method comprising:

obtaining a window handle of a window displayed in a display screen;

determining, based on the obtained window handle, whether an application regarding the displayed window is a predetermined application or not;

acquiring a patient ID in a case where the application regarding the displayed window is the predetermined application;

determining whether a GUI (Graphical User Interface) component regarding the displayed window is a predetermined GUI component or not;

acquiring an area including the patient ID in the displayed window as an image in a case where the GUI component is not the predetermined GUI component;

acquiring character code strings as the patient ID by performing a character recognition on the image in a case where the GUI component is not the predetermined GUI component, acquiring the patient ID without performing the character recognition on the image in a case where the GUI component is the predetermined GUI component; and acquiring material information for a conference from a server based on the acquired patient ID.

6. A non-transitory computer-readable medium storing executable instructions, which when executed by one or more processors, cause the one or more processors to perform operations comprising:

obtaining a window handle of a window displayed in a display screen;

determining, based on the obtained window handle, whether an application regarding the displayed window is a predetermined application or not;

acquiring a patient ID in a case where the application regarding the displayed window is the predetermined application;

determining whether a GUI (Graphical User Interface) component regarding the displayed window is a predetermined GUI component or not;

acquiring an area including the patient ID in the displayed window as an image in a case where the GUI component is not the predetermined GUI component;

acquiring character code strings as the patient ID by performing a character recognition on the image in a case where the GUI component is not the predetermined GUI component, acquiring the patient ID without performing the character recognition on the image in a case where the GUI component is the predetermined GUI component; and acquiring material information for a conference from a server based on the acquired patient ID.

* * * * *